(12) United States Patent
Ibrahim et al.

(10) Patent No.: US 8,865,735 B2
(45) Date of Patent: Oct. 21, 2014

(54) SOLID FORMS OF A PHARMACEUTICALLY ACTIVE SUBSTANCE

(75) Inventors: Prabha N. Ibrahim, Mountain View, CA (US); Gary Conard Visor, Castro Valley, CA (US); Shan-Ming Kuang, Florence, SC (US); Baoshu Zhao, Florence, SC (US); Ralph Diodone, Breisach (DE); Karsten Fähnrich, Grenzach-Wyhlen (DE); Urs Schwitter, Reinach (CH)

(73) Assignees: Hoffman-La Roche Inc., Nutley, NJ (US); Plexxikon Inc., Berkeley, CA (US)

( * ) Notice: Subject to any disclaimer, the term of this patent is extended or adjusted under 35 U.S.C. 154(b) by 0 days.

(21) Appl. No.: 13/817,124

(22) PCT Filed: Feb. 21, 2012

(86) PCT No.: PCT/US2012/025965
§ 371 (c)(1),
(2), (4) Date: Oct. 18, 2013

(87) PCT Pub. No.: WO2012/161776
PCT Pub. Date: Nov. 29, 2012

(65) Prior Publication Data
US 2014/0039002 A1 Feb. 6, 2014

Related U.S. Application Data

(60) Provisional application No. 61/444,866, filed on Feb. 21, 2011.

(51) Int. Cl.
| | | |
|---|---|---|
| A01N 43/42 | (2006.01) | |
| A61K 31/44 | (2006.01) | |
| C07D 471/02 | (2006.01) | |
| C07D 491/02 | (2006.01) | |
| C07D 498/02 | (2006.01) | |

(52) U.S. Cl.
USPC .................................. 514/300; 546/113

(58) Field of Classification Search
USPC .................................. 514/300; 546/113
See application file for complete search history.

(56) References Cited

U.S. PATENT DOCUMENTS

| | | |
|---|---|---|
| 2,234,705 A | 3/1941 | Normington, Et Al. |
| 2,413,258 A | 12/1946 | Soday, Et Al |
| 4,150,949 A | 4/1979 | Smith |
| 4,568,649 A | 2/1986 | Bertoglio-Matte |
| 4,626,513 A | 12/1986 | Burton et al. |
| 4,634,701 A | 1/1987 | De Vincentiis |
| 4,714,693 A | 12/1987 | Targos |
| 4,727,395 A | 2/1988 | Oda et al. |
| 4,863,945 A | 9/1989 | Friebe et al. |
| 5,120,782 A | 6/1992 | Hubsch et al. |
| 5,143,854 A | 9/1992 | Pirrung et al. |
| 5,338,849 A | 8/1994 | Festal et al. |
| 5,426,039 A | 6/1995 | Wallace et al. |
| 5,432,177 A | 7/1995 | Baker et al. |
| 5,434,049 A | 7/1995 | Okano et al. |
| 5,449,614 A | 9/1995 | Danos et al. |
| 5,474,935 A | 12/1995 | Chatterjee et al. |
| 5,486,525 A | 1/1996 | Summers, Jr. et al. |
| 5,556,752 A | 9/1996 | Lockhart et al. |
| 5,576,319 A | 11/1996 | Baker et al. |
| 5,580,859 A | 12/1996 | Felgner et al. |
| 5,631,236 A | 5/1997 | Woo et al. |
| 5,632,957 A | 5/1997 | Heller et al. |
| 5,658,775 A | 8/1997 | Gilboa |
| 5,681,959 A | 10/1997 | Bishop et al. |
| 5,700,637 A | 12/1997 | Southern |
| 5,700,809 A | 12/1997 | Leeson et al. |
| 5,712,285 A | 1/1998 | Curtis et al. |
| 5,721,118 A | 2/1998 | Scheffler |

(Continued)

FOREIGN PATENT DOCUMENTS

| | | |
|---|---|---|
| CA | 2550361 | 7/2005 |
| DE | 24 13 258 | 10/1975 |

(Continued)

OTHER PUBLICATIONS

Ahmad, K., "BRAF mutation common to 70% of thyroid carcinomas," The Lancet, Oncology, (2003), 4:330.
Alfthan, K., "Surface Plasmon Resonance Biosensors as a Tool in Antibody Engineering," Biosensors & Bioelectronics, (1998), 13:653-663.
Allegretti, et al., "Palladium-Catalysed Functionalisation at 4- and 6-Position of the 7-Azaindole System," Synlett, (2001), 5:609-612.
Al-Obeidi, et al., Peptide and Peptidomimetic Libraries, Mol Biotechnol., (1998), 9:205-223.
Alvarez, et al., "Synthesis of 3-Aryl- and 3-Heteroaryl-7-Azaindoles," Synthesis, (1999), 4:615-620.

(Continued)

Primary Examiner — Niloofar Rahmani
(74) Attorney, Agent, or Firm — Sheppard Mullin Richter & Hampton LLP

(57) ABSTRACT

The present invention provides solid forms of the compound of formula 1 and pharmaceutical uses thereof.

(1)

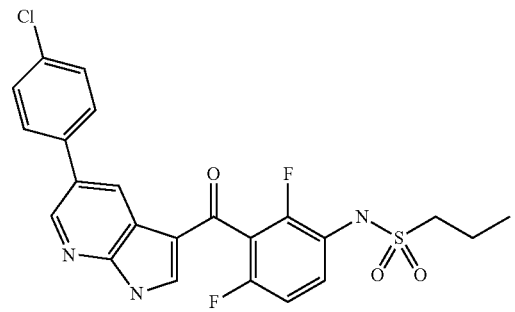

30 Claims, 29 Drawing Sheets

(56) References Cited

U.S. PATENT DOCUMENTS

| | | |
|---|---|---|
| 5,744,305 A | 4/1998 | Fodor et al. |
| 5,747,276 A | 5/1998 | Hoch et al. |
| 5,763,198 A | 6/1998 | Hirth et al. |
| 5,770,456 A | 6/1998 | Holmes |
| 5,800,992 A | 9/1998 | Fodor et al. |
| 5,807,522 A | 9/1998 | Brown et al. |
| 5,830,645 A | 11/1998 | Pinkel et al. |
| 5,840,485 A | 11/1998 | Lebl et al. |
| 5,856,174 A | 1/1999 | Lipshutz et al. |
| 5,858,995 A | 1/1999 | Kawai et al. |
| 5,877,007 A | 3/1999 | Housey |
| 5,952,362 A | 9/1999 | Cournoyer et al. |
| 5,959,098 A | 9/1999 | Goldberg et al. |
| 5,965,452 A | 10/1999 | Kovacs |
| 6,013,440 A | 1/2000 | Lipshutz et al. |
| 6,022,963 A | 2/2000 | McGall et al. |
| 6,025,155 A | 2/2000 | Hadlaczky et al. |
| 6,045,996 A | 4/2000 | Cronin et al. |
| 6,048,695 A | 4/2000 | Bradley et al. |
| 6,054,270 A | 4/2000 | Southern |
| 6,090,912 A | 7/2000 | Lebl et al. |
| 6,096,718 A | 8/2000 | Weitzman et al. |
| 6,107,478 A | 8/2000 | Pedersen et al. |
| 6,110,456 A | 8/2000 | During |
| 6,110,458 A | 8/2000 | Freeman et al. |
| 6,113,913 A | 9/2000 | Brough et al. |
| 6,117,681 A | 9/2000 | Salmons et al. |
| 6,161,776 A | 12/2000 | Byles |
| 6,178,384 B1 | 1/2001 | Kolossvary |
| 6,235,769 B1 | 5/2001 | Clary |
| 6,243,980 B1 | 6/2001 | Bronstein et al. |
| 6,258,606 B1 | 7/2001 | Kovacs |
| 6,261,776 B1 | 7/2001 | Pirrung et al. |
| 6,277,489 B1 | 8/2001 | Abbott et al. |
| 6,277,628 B1 | 8/2001 | Johann et al. |
| 6,288,234 B1 | 9/2001 | Griffin |
| 6,294,330 B1 | 9/2001 | Michnick et al. |
| 6,310,074 B1 | 10/2001 | Depreux et al. |
| 6,350,786 B1 | 2/2002 | Albano et al. |
| 6,545,014 B2 | 4/2003 | Verner |
| 6,653,309 B1 | 11/2003 | Saunders et al. |
| 6,858,860 B2 | 2/2005 | Hosono et al. |
| 6,897,207 B2 | 5/2005 | Cox et al. |
| 7,259,165 B2 | 8/2007 | Bernotas et al. |
| 7,361,763 B2 | 4/2008 | Arnold et al. |
| 7,361,764 B2 | 4/2008 | Arnold et al. |
| 7,452,993 B2 | 11/2008 | Arnold et al. |
| 7,498,342 B2 | 3/2009 | Ibrahim et al. |
| 7,504,509 B2 | 3/2009 | Ibrahim et al. |
| 7,582,637 B2 | 9/2009 | Arnold et al. |
| 7,601,839 B2 | 10/2009 | Arnold et al. |
| 7,626,021 B2 | 12/2009 | Arnold et al. |
| 7,846,941 B2 | 12/2010 | Zhang et al. |
| 7,863,288 B2 | 1/2011 | Ibrahim et al. |
| 7,863,289 B2 | 1/2011 | Spevak et al. |
| 7,893,075 B2 | 2/2011 | Zhang et al. |
| 7,994,185 B2 | 8/2011 | Rheault |
| 8,067,638 B2 | 11/2011 | Kai et al. |
| 8,404,700 B2 | 3/2013 | Ibrahim et al. |
| 2001/0001449 A1 | 5/2001 | Kiliany et al. |
| 2001/0008765 A1 | 7/2001 | Shinoki et al. |
| 2001/0012537 A1 | 8/2001 | Anderson et al. |
| 2001/0014448 A1 | 8/2001 | Chappa et al. |
| 2001/0014449 A1 | 8/2001 | Nerenberg et al. |
| 2001/0016322 A1 | 8/2001 | Caren et al. |
| 2001/0018642 A1 | 8/2001 | Balaban et al. |
| 2001/0019827 A1 | 9/2001 | Dawson et al. |
| 2003/0003004 A1 | 1/2003 | Stones et al. |
| 2003/0219489 A1 | 11/2003 | Curatolo et al. |
| 2004/0002534 A1 | 1/2004 | Lipson et al. |
| 2004/0022534 A1 | 2/2004 | Amano et al. |
| 2004/0067257 A1 | 4/2004 | Bateman et al. |
| 2004/0077595 A1 | 4/2004 | Cheng et al. |
| 2004/0142864 A1 | 7/2004 | Bremer et al. |
| 2004/0167030 A1 | 8/2004 | Bernotas et al. |
| 2005/0026792 A1 | 2/2005 | Cartwright |
| 2005/0031692 A1 | 2/2005 | Beyerinck et al. |
| 2005/0085463 A1 | 4/2005 | Weiner et al. |
| 2005/0154014 A1 | 7/2005 | Bloxham et al. |
| 2005/0164300 A1 | 7/2005 | Artis et al. |
| 2005/0170431 A1 | 8/2005 | Ibrahim et al. |
| 2005/0256151 A1 | 11/2005 | Salom et al. |
| 2006/0018726 A1 | 1/2006 | Hall |
| 2006/0024361 A1 | 2/2006 | Odidi et al. |
| 2006/0035898 A1 | 2/2006 | Arnold et al. |
| 2006/0058339 A1 | 3/2006 | Ibrahim et al. |
| 2006/0058340 A1 | 3/2006 | Ibrahim et al. |
| 2007/0032519 A1 | 2/2007 | Zhang et al. |
| 2007/0049615 A1 | 3/2007 | Ibrahim et al. |
| 2007/0054963 A1 | 3/2007 | Lifshitz-Liron et al. |
| 2007/0072862 A1 | 3/2007 | Dimauro et al. |
| 2007/0218138 A1 | 9/2007 | Bittorf et al. |
| 2007/0287711 A1 | 12/2007 | Arnold et al. |
| 2008/0079906 A1 | 4/2008 | Finn |
| 2008/0167338 A1 | 7/2008 | Spevak et al. |
| 2008/0188514 A1 | 8/2008 | Wu et al. |
| 2009/0005356 A1 | 1/2009 | Blaney et al. |
| 2009/0076046 A1 | 3/2009 | Zhang et al. |
| 2009/0143352 A1 | 6/2009 | Arnold et al. |
| 2009/0306056 A1 | 12/2009 | Arnold et al. |
| 2010/0310659 A1* | 12/2010 | Desai et al. .................. 424/486 |
| 2011/0112136 A1 | 5/2011 | Diodone et al. |
| 2013/0172375 A1 | 7/2013 | Albano et al. |

FOREIGN PATENT DOCUMENTS

| | | |
|---|---|---|
| EP | 0 344 603 | 5/1989 |
| EP | 0 154 734 | 8/1990 |
| EP | 0 465 970 | 1/1992 |
| EP | 0 580 860 | 4/1992 |
| EP | 0 148 725 | 5/1994 |
| EP | 0 596 406 | 5/1994 |
| EP | 0 901 786 | 7/1998 |
| EP | 0 988 863 | 3/2000 |
| EP | 1 057 826 | 12/2000 |
| EP | 1 368 001 | 2/2002 |
| EP | 0 870 768 | 5/2002 |
| EP | 1 267 111 | 12/2002 |
| EP | 1 749 829 | 2/2007 |
| FR | 2264804 | 10/1975 |
| GB | 1 198 301 A | 5/1973 |
| GB | 2 292 143 | 2/1996 |
| GB | 2 292 145 | 2/1996 |
| GB | 2 298 198 | 8/1996 |
| GB | 2 299 581 | 10/1996 |
| JP | 06-135946 | 5/1994 |
| JP | 10-087629 | 4/1998 |
| JP | 10-130269 | 5/1998 |
| JP | 2000-95708 | 4/2000 |
| JP | 2001-278886 | 10/2001 |
| JP | 15-073357 | 3/2003 |
| WO | WO-93/13099 | 7/1993 |
| WO | WO-94/14808 | 7/1994 |
| WO | WO-94/20459 | 9/1994 |
| WO | WO-94/20497 | 9/1994 |
| WO | WO-95/04742 | 2/1995 |
| WO | WO-95/07910 | 3/1995 |
| WO | WO-95/28387 | 10/1995 |
| WO | WO-96/00226 | 1/1996 |
| WO | WO-96/11929 | 2/1996 |
| WO | WO-96/05200 | 4/1996 |
| WO | WO-96/17958 | 6/1996 |
| WO | WO-96/18738 | 6/1996 |
| WO | WO-96/38131 | 12/1996 |
| WO | WO-97/03967 | 2/1997 |
| WO | WO-97/46313 | 12/1997 |
| WO | WO-97/46558 | 12/1997 |
| WO | WO-97/49703 | 12/1997 |
| WO | WO-98/06433 | 2/1998 |
| WO | WO-98/22457 | 5/1998 |
| WO | WO-98/47899 | 10/1998 |
| WO | WO-99/00386 | 1/1999 |
| WO | WO-99/09217 | 2/1999 |
| WO | WO-99/32433 | 7/1999 |

(56) References Cited

FOREIGN PATENT DOCUMENTS

| | | |
|---|---|---|
| WO | WO-99/51231 | 10/1999 |
| WO | WO-99/51232 | 10/1999 |
| WO | WO-99/51233 | 10/1999 |
| WO | WO-99/51234 | 10/1999 |
| WO | WO-99/51595 | 10/1999 |
| WO | WO-99/51596 | 10/1999 |
| WO | WO-99/51773 | 10/1999 |
| WO | WO-00/09162 | 2/2000 |
| WO | WO-00/12074 | 3/2000 |
| WO | WO-00/12514 | 3/2000 |
| WO | WO-00/17202 | 3/2000 |
| WO | WO-00/29411 | 5/2000 |
| WO | WO-00/53582 | 9/2000 |
| WO | WO-00/55153 | 9/2000 |
| WO | WO-00/64898 | 11/2000 |
| WO | WO-00/71506 | 11/2000 |
| WO | WO-00/71537 | 11/2000 |
| WO | WO-00/75139 | 12/2000 |
| WO | WO-01/09121 | 2/2001 |
| WO | WO-01/24236 | 4/2001 |
| WO | WO-01/29036 | 4/2001 |
| WO | WO-01/46196 | 6/2001 |
| WO | WO-01/60822 | 8/2001 |
| WO | WO-01/62255 | 8/2001 |
| WO | WO-01/74786 | 11/2001 |
| WO | WO-01/98299 | 12/2001 |
| WO | WO-02/00657 | 1/2002 |
| WO | WO-02/18346 | 3/2002 |
| WO | WO-02/083175 | 10/2002 |
| WO | WO-02/085896 | 10/2002 |
| WO | WO-02/102783 | 12/2002 |
| WO | WO-03/000258 | 1/2003 |
| WO | WO-03/000267 | 1/2003 |
| WO | WO-03/003004 | 1/2003 |
| WO | WO-03/004472 | 1/2003 |
| WO | WO-03/006459 | 1/2003 |
| WO | WO-03/008422 | 1/2003 |
| WO | WO-03/011868 | 2/2003 |
| WO | WO-03/020698 | 3/2003 |
| WO | WO-03/028724 | 4/2003 |
| WO | WO-03/037862 | 5/2003 |
| WO | WO-03/051838 | 6/2003 |
| WO | WO-03/064413 | 8/2003 |
| WO | WO-03/068221 | 8/2003 |
| WO | WO-03/082289 | 10/2003 |
| WO | WO-03/082868 | 10/2003 |
| WO | WO-03/082869 | 10/2003 |
| WO | WO-03/087087 | 10/2003 |
| WO | WO-03/101990 | 12/2003 |
| WO | WO-2004/005283 | 1/2004 |
| WO | WO-2004/009600 | 1/2004 |
| WO | WO-2004/009601 | 1/2004 |
| WO | WO-2004/014369 | 2/2004 |
| WO | WO-2004/016609 | 2/2004 |
| WO | WO-2004/016610 | 2/2004 |
| WO | WO-2004/024895 | 3/2004 |
| WO | WO-2004/052880 | 6/2004 |
| WO | WO-2004/054581 | 7/2004 |
| WO | WO-2004/056830 A | 7/2004 |
| WO | WO-2004/065393 | 8/2004 |
| WO | WO-2004/065394 | 8/2004 |
| WO | WO-2004/069138 | 8/2004 |
| WO | WO-2004/074286 | 9/2004 |
| WO | WO-2004/078756 | 9/2004 |
| WO | WO-2004/078923 | 9/2004 |
| WO | WO-2004/101565 | 11/2004 |
| WO | WO-2005/028475 | 3/2005 |
| WO | WO-2005/028624 | 3/2005 |
| WO | WO-2005/030128 | 4/2005 |
| WO | WO-2005/034869 | 4/2005 |
| WO | WO-2005/044181 | 5/2005 |
| WO | WO-2005/058891 | 6/2005 |
| WO | WO-2005/062795 | 7/2005 |
| WO | WO-2005/063746 | 7/2005 |
| WO | WO-2005/063747 | 7/2005 |
| WO | WO-2005/066347 | 7/2005 |
| WO | WO-2005/082367 | 9/2005 |
| WO | WO-2005/085244 | 9/2005 |
| WO | WO-2005/086904 | 9/2005 |
| WO | WO-2005/092896 | 10/2005 |
| WO | WO-2005/095400 | 10/2005 |
| WO | WO-2005/103050 | 11/2005 |
| WO | WO-2005/115363 | 12/2005 |
| WO | WO-2005/115374 | 12/2005 |
| WO | WO-2006/004984 | 1/2006 |
| WO | WO-2006/009755 | 1/2006 |
| WO | WO-2006/009797 | 1/2006 |
| WO | WO-2006/010637 | 2/2006 |
| WO | WO-2006/015123 | 2/2006 |
| WO | WO-2006/015124 | 2/2006 |
| WO | WO-2006/063167 | 6/2006 |
| WO | WO-2006/114180 | 11/2006 |
| WO | WO-2006/114520 | 11/2006 |
| WO | WO-2006/127587 | 11/2006 |
| WO | WO-2006/137376 | 12/2006 |
| WO | WO-2007/002325 | 1/2007 |
| WO | WO-2007/002433 | 1/2007 |
| WO | WO-2007/013896 | 2/2007 |
| WO | WO-2007/022380 | 2/2007 |
| WO | WO-2007/106236 | 9/2007 |
| WO | WO-2008/058341 | 5/2008 |
| WO | WO-2008/079903 | 7/2008 |
| WO | WO-2008/079906 | 7/2008 |
| WO | WO-2008/079909 | 7/2008 |
| WO | WO-2008/138755 | 11/2008 |
| WO | WO-2009/012791 | 1/2009 |
| WO | WO-2009/111277 | 9/2009 |
| WO | WO-2009/111278 | 9/2009 |
| WO | WO-2009/111279 | 9/2009 |
| WO | WO-2009/111280 | 9/2009 |
| WO | WO-2010/114928 | 10/2010 |
| WO | WO-2012/161776 | 11/2012 |

OTHER PUBLICATIONS

Amersdorfer, et al., "Phage Libraries for Generation of Anti-Botulinum scFv Antibodies," Methods in Molecular Biology, (2000), 145:219-240.

Amiel, et al., "Hirschsprung disease, associated syndromes and genetics: a review," J Med Genet., (2008), 45:1-14.

Anderson, et al., "Cooperative Catalyst Effects in Palladium-Mediated Cyanation Reactions of Aryl Halides and Triflates," J. Org. Chem., (1998), 63:8224-8228.

Antonini, et al., "Synthesis of 4-Amino-1-β-D-Ribofuranosyl-1H-pyrrolo[2,3-b]pyridine (1-Deazatubercidin) as a Potential Antitumor Agent," J. Med. Chem., (1982), 25:1258-1261.

Arthan et al., "Leukemia inhibitory factor can mediate Ras/Raf/MEK/ERK-induced growth inhibitory signaling in medullary thyroid cancer cells," Cancer Letters (2010) 297:31-41.

Ashman, et al., "The biology of stem cell factor and its receptor C-kit," The International Journal of Biochemistry & Cell Biology, (1999), 31:1037-1051.

Baghestanian, et al., "A Case of Malignant Mastocytosis with Circulating Mast Cell Precursors: Biologic and Phenotypic Characterization of the Malignant Clone," Leuk., (1996), 10:159-166.

Bagshaw et al., "Measurement of Ligand Binding to Proteins," Spectrophotometry and Spectrofluorimetry: A Practical Approach, (1987), 4:91-113.

Bagshawe, K., "Antibody-Directed Enzyme Prodrug Therapy: A Review," Drug Dev. Res., (1995), 34:220-230.

Balak, et. al., "Novel D761Y and Common Secondary T790M Mutations in Epidermal Growth Factor Receptor 13 Mutant Lung Adenocarcinomas with Acquired Resistance to Kinase Inhibitors," Clin Cancer Res., (2006), 12:6494-501.

Bancalari, et al., "Blood Markers of Early and Late Airway Responses to Allergen in Asthmatic Subjects. Relationship with Functional Findings," Allergy, (1997), 52:32-40.

Bartlett, et al., "CAVEAT: A Program to Facilitate the Structure-Derived Design of Biologically Active Molecules," Royal Society of Chemistry, (1989), 78:I80-I96.

Barton, et al., "The chemistry of pentavalent organobismuth reagents. Part X. Studies on the phenylation and oxidation of phenols," Tetrahedron, (1987), 43(2):323-332.

(56) References Cited

OTHER PUBLICATIONS

Basta, et al., "High-dose Intravenous Immunoglobulin Exerts Its Beneficial Effect in Patients with Dermatomyositis by Blocking Endomysial Deposition of Activated Complement Fragments," J Clin Invest., (1994), 94:1729-1735.
Basto, et al., "Mutation analysis of B-RAF gene in human gliomas," Acta Neuropathol., (2005), 109:207-210.
Bedi, et al., "BCR-ABL-Mediated Inhibition of Apoptosis With Delay of G2/M Transition After DNA Damage: A Mechanism of Resistance to Multiple Anticancer Agents," Blood, (1995), 86:1148-1158.
Bell, J.E., "Fluorescence: Solution Studies" Spectroscopy in Biochemistry I, (1981),(4):155-194.
Bellone, et al., "Growth Stimulation of Colorectal Carcinoma Cells Via the c-Kit Receptor is Inhibited by TGF-β1," J. Cell Physiol., (1997), 172:1-11.
Berdel, et al., "Recombinant Human Stem Cell Factor Stimulates Growth of a Human Glioblastoma Cell Line Expressing c-kit Protooncogene," Canc. Res., (1992), 52:3498-3502.
Bertolini, et al., "A New Rational Hypothesis for the Pharmacophore of the Active Metabolite of Leflunomide, a Potent Immunosuppressive Drug," J. Med. Chem., (1997), 40:2011-2016.
Bjorntrop, "Neuroendocrine Pertuirbations as a Cause of Insulin Resistance," Diabetes Metab. Res. Rev., (1999), 15:427-441.
Bloom, et al., "The Preparation of 2-Alkylaminobenzimidazoles," J. Org. Chem., (1939), 14-19.
Blundell, et al., "Knowledge-Based Protein Modelling and Design," Eur. J. Biochem., (1988), 172:513-520.
Bode, et al., "Mutations in the tyrosine kinase domain of the EGFR gene are rare in synovial sarcoma," Modern Pathology, (2006), 19:541-547.
Bohm, H-J., "On the Use of LUDI to Search the Fine Chemicals Directory for Ligands of Proteins of Known Three-Dimensional Structure," J. Comp. Aided Molec. Design, (1994), 8:623-632.
Bokenmeyer, et al., "Expression of Stem-Cell Factor and Its Receptor c-kit Protein in Normal Testicular Tissue and Malignant Germ-Cell Tumours," J. Cancer Res. Clin. Oncol., (1996), 122:301-306.
Bolger, et al., "Computer Modeling of Combining Site Structure of Anti-Hapten Monoclonal Antibodies," Methods Enz., (1991), 203:21-45.
Bongarzone, et al., "High Frequency of Activation of Tyrosine Kinase Oncogenes in Human Papillary Thyroid Carcinoma," Oncogene, (1989), 4(12):1457-1462.
Bothwell, M., "Keeping Track of Neurotrophin Receptors," Cell, (1991), 65:915-918.
Bouzakri, et al., "MAP4K4 Gene silencing in Human Skeletal Muscle Prevents Tumor Necrosis Factor-a-induced Insulin Resistance," J. Biol. Chem., (2007), 282:7783-7789.
Bowtell, D., "Options Available From Start to Finish for Obtaining Expression Data by Microarray," Nature Genetics Supp., (1999), 21:25-32.
Brenner, et al., "Encoded Combinatorial Chemistry," Proc. Natl. Acad. Sci. USA, (1992), 89:5381-5383.
Broudy, V., "Stem Cell Factor and Hematopoiesis," Blood, (1997), 90:1345-1364.
Brunger, A.T., "Free R Value: a Novel Statistical Quantity for Assessing the Accuracy of Crystal Structures," Nature, (1992), 355:472-475.
Buchschacher, et al., "Human Immunodeficiency Virus Vectors for Inducible Expression of Foreign Genes," J. Virol., (1992), 66:2731-2739.
Calabresi, et al., "Section IX: Chemotherapy of neoplastic diseases," Goodman & Gilman's the Pharmacological Basis of Therapeutics, Tenth Edition, McGraw-Hill Medical Publishing Division (2001), pp. 1381, 1383-1385 and 1388.
Capon, et al., "Designing CD4 Immunoadhesins for Aids Therapy," Nature, (1989), 337:525-531.
Carell, et al., "New Promise in Combinatorial Chemistry: Synthesis, Characterization, and Screening of Small-Molecule Libraries in Solution," Chem. Biol., (1995), 2:171-183.
Carpino, et al., "p62dok: a Constitutively Tyrosine-Phosphorylated, GAP-Associated Protein in Chronic Myelogenous Leukemia Progenitor Cells," Cell, (1997), 88:197-204.
Castelle, et al., "The Presence of Membrane-Bound Stem Cell Factor on Highly Immature Nonmetachromatic Mast Cells in the Peripheral Blood of a Patient with Aggressive Systemic Mastocytosis," J. Aller. Clin. Immunol., (1996), 98:831-840.
Castellone, et al., "A novel de novo germ-line V292M mutation in the extracellular region of RET in a patient with phaeochromocytoma and medullary thyroid carcinoma: functional characterization," Clinical Endocrinology, (2010), 73:529-534.
Castro, et al. "Utilizacion de dispersiones solidas como estrategia para aumentar la velocidad de disolucion de farmacos", Nuestra Farmcia, (2008), 25:24-29 (No English Translation Available).
Chabala, J., "Solid-Phase Combinatorial Chemistry and Novel Tagging Methods for Identifying Leads," Curr Opin Biotechnol., (1995), 6:632-639.
Chayer, et al., "Synthesis of Carboranylpyrroles," Tetrahedron Lett., (2001), 42(44):7759-7761.
Checovich, et al., "Fluorescence Polarization—a New Tool for Cell and Molecular Biology," Nature, (1995), 375:254-256.
Chou, et al., "Chemotherapeutic Synergism, Potentiation and Antagonism, Encyclopedia of Human Biology, Academic Press," (1991), 2:371-379.
Chou, et al., "Computerized Quantitation of Synergism and Antagonism of Taxol, Topotecan, and Cisplatin Against Human Teratocarcinoma Cell Growth: a Rational Approach to Clinical Protocol Design," J. Natl. Cancer Inst., (1994), 86:1517-1524.
Chou, et al., "Quantitative analysis of Dose-Effect Relationships: The Combined Effects of Multiple Drugs or Enzyme Inhibitors," Adv. Enzyme Regul., (1984), 22:27-55.
Chou, et al., "Synergism and Antagonism in Chemotherapy," Academic Press, (1991), Chapter 2, 61-102.
Clark, et al., "PRO_LIGAND: An Approach to De Novo Molecular Design. 1. Application to the Design of Organic Molecules," J. Comp. Aided Molec. Design, (1995), 9:13-32.
Clohisy, et al., "Review of Cellular Mechanisms of Tumor Osteolysis," Clin. Orthop., (2000), 373:104-114.
Coe, et al., "Solution-Phase Combinatorial Chemistry," Mol Divers., (1999), 4:31-38.
Coelho, et al., "Studies of RET gene expression and acetylcholinesterase activity in a series of sporadic Hirschsprung's disease," Pediatr Surg Int, (2008), 24:1017-1021.
Cohen, et al., "Expression of Stem Cell Factor and C-Kit in Human Neuroblastoma," Blood, (1994), 84:3465-3472.
Collins, et al., "A small interfereing RNA screen for modulators of tumor cell motility identifies MAP4K4 as a prommigratory kinase," Proc. Natl. Acad. Sci. USA, (2006), 103:3775-3780.
Collioud, et al., "Oriented and Covalent Immobilization of Target Molecules to Solid Supports: Synthesis and Application of a Light-Activatable and Thiol-Reactive Cross-Linking Reagent," Bioconjugate Chem., (1993), 4:528-536.
Colman, P.M., "Structure-Based Drug Design," Current Opinion in Struc. Biol., (1994), 4:868-874.
Columbo, et al., "The Human Recombinant c-kit Receptor Ligand, rhSCF, Induces Mediator Release From Human Cutaneous Mast Cells and Enhances IgE-Dependent Mediator Release From Both Skin Mast Cells and Peripheral Blood Basophils," J. Immunol., (1992), 149:599-608.
Communication Pursuant to Article 94(3) EPC for European Application No. 04814626.0 dated Jun. 6, 2011 (039363-1907).
Communication Pursuant to Article 94(3) EPC for European Application No. 04814626.0 dated Dec. 15, 2009 (039363-1907).
Communication Pursuant to Article 94(3) EPC for European Application No. 05789913.0 dated Feb. 15, 2010 (039363-2126).
Communication Pursuant to Article 94(3) EPC for European Application No. 06773861.7 dated Apr. 22, 2010 (039363-2869).
Communication Pursuant to Article 94(3) EPC for European Application No. 06773861.7 dated Jul. 9, 2009 (039363-2869).
Communication Pursuant to Article 94(3) EPC for European Application No. 06773861.7 dated Dec. 21, 2009 (039363-2869).
Communication Pursuant to Article 94(3) EPC for European Application No. 06813186.1 dated Sep. 15, 2009 (039363-4009).

(56) References Cited

OTHER PUBLICATIONS

Communication Pursuant to Article 94(3) EPC for European Application No. 07864681.7 dated Dec. 2, 2009 (039363-4141).
Communication Pursuant to Article 94(3) EPC for European Application No. 10722860.3 dated Mar. 27, 2013.
Costa, et al., "The Cells of the Allergic Response," JAMA, (1997), 278:1815-1822.
Coste, et al., "Coupling N-Methylated Amino Acids Using PyBroP1 and PyCloP Halogenophosphonium Salts: Mechanism and Fields of Application," Journal of Organic Chemistry, (1994), 59:2437-2446.
Coulie, et al., "Recombinant Human Neurotropic Factors Accelerate Colonic Transit and Relieve Constipation in Humans," Gastroenterology, (2000), 119:41-50.
Creighton, T., "An Empirical Approach to Protein Conformation Stability and Flexibility," Biopolymers, (1983), 22(1):49-58.
Crouch, et al., "The use of ATP bioluminescence as a measure of cell proliferation and cytotoxicity," Journal of Immunological Methods, (1993), 160:81-88.
Crump, M., "Inhibition of Raf Kinase in the Treatment of Acute Myeloid Leukemia," Curr. Pharm. Design, (2002), 8(25):2243-2248.
Curtin, et al., "Discovery and Evaluation of a Series of 3-Acylindole Imidazopyridine Platelet-Activating Factor Antagonists," J. Med. Chem., (1998), 41:74-95.
Cwirla, et al., "Peptides on Phage: A Vast Library of Peptides for Identifying Ligands," Biochemistry, (1990), 87:6378-6382.
Dai, et al., "Targeted disruption of the mouse colony-stimulating factor 1 receptor gene results in osteopetrosis, mononuclear phagocyte deficiency, increased primitive progenitor cell frequencies, and reproductive defects," Blood, (2002), 99: 111-120.
Dandliker, et al., "Equilibrium and Kinetic Inhibition Assays Based Upon Fluorescence Polarization," Methods in Enzymology, (1981), 74:3-28.
Das-Gupta et al., "Acridine Derivatives, Part VI," J. Indian Chem. Society, (1941), 18:25-28.
Dastych, et al., "Stem Cell Factor Induces Mast Cell Adhesion to Fibronectin," J. Immunol., (1994), 152:213-219.
Davies, et al., "Mutations of the BRAF gene in human cancer," Nature, (2002), 417:949-954.
Demetri, G.D., "Targeting c-kit mutations in solid tumors: Scientific rationale and novel therapeutic options," Seminars in Oncology, (2001), 28(5), Supp. 17, 19-26.
Dewar, et al., "Inhibition of c-fms by Imatinib Expanding the Spectrum of Treatment," Cell Cycle, (2005), 4(7):851-853.
Dobeli, et al., "Recombinant Fusion Proteins for the Industrial Production of Disulfide Bridge containing Peptides: Purification, Oxidation without Cancatamer Formation, and Selective Cleavage," Protein Expr. Purif., (1998), 12:404-414.
Dolle, et al., "Comprehensive Survey of Combinatorial Library Synthesis: 1998," J Comb Chem., (1999), 1:235-282.
Dong, et al., "BRAF Oncogenic Mutations Correlate with Progression rather than Initiation of Human Melanoma," Cancer Research, (2003), 63:3883-3885.
Donis-Keller, et al., "Mutations in the RET Proto-Oncogene are Associated with MEN 2A and FMTC," Hum Mol Genet., (1993), 2(7):851-856.
Douma, et al., "Suppression of anoikis and induction of metastasis by the neurotropic receptor TrkB," Nature, (2004), 430:1034-1039.
Doyle, et al., "Alkyl Nitrite-metal halide Deamination Reactions. 6. Direct Synthesis of Arenediazonium Tetrafluoroborate Salts from Aromatic Amines, tert-Butyl Nitrite, and Boron Trifluoride Etherate in Anhydrous Media," J. Org. Chem., (1979), 44:1572.
Dube, et al., "Reductive N-Alkylation of Amides, Carbamates and Ureas," Tetrahedron Lett., (1999), 40:2295-2298.
Durbec, et al., "GDNF Signalling Through the Ret Receptor Tyrosine Kinase," Nature, (1996), 381:789-793.
Dutcher et al., "Studies of the C11H8N2OS Degradation Product of Gliotoxin," J. Am. Chem. Soc., (1951), 73:4139-4141.
Dyson, et al., "The Human Papilloma Virus 13 16 E7 Oncoprotein is Able to Bind to the Retinoblastoma Gene Product," Science, (1989), 243:934-937.
Eklund, et al., "Treatment of rheumatoid arthritis with imatinib mesylate: clinical improvements in three refractory cases, Annals of Medicine," (2003), 35:362-367.
Eliseev, et al., "Dynamic Combinatorial Chemistry: Evolutionary Formation and Screening of Molecular Libraries," Current Topics in Microbiology & Immunology, (1999), 243:159-172.
Enjalbal, et al., "Mass Spectrometry in Combinatorial Chemistry," Mass Spectrometry Reviews, (2000), 19:139-161.
Escribano, et al., "Expression of the c-kit (CD117) Molecule in Normal and Malignant Hematopoiesis," Leuk. Lymph., (1998), 30:459-466.
Felder, E.R., "The Challenge of Preparing and Testing Combinatorial Compound Libraries in the Fast Lane, at the Front End of Drug Development," Chimia., (1994), 48:531-541.
Feng, et al., "Stable in Vivo Gene Transduction Via a Novel Adenoviral/Retroviral Chimeric Vector," Nature Biotechnology, (1997), 15:866-870.
Feng, et al., "Tyrosines 559 and 807 in the Cytoplasmic Tail of the Macrophage colony-Stimulating Factor Receptor Play Distinct Roles in Osteoclast Differentiation and Function," Endocrinology, (2002), 143: 4868-4874.
Finotto, et al., "Glucocorticoids Disease Tissue Mast Cell No. By Reducing the Production of the c-kit Ligand, Stem Cell Factor, by Resident Cells," J. Clin. Invest., (1997), 99:1721-1728.
Fivash, et al., "BIAcore for macromolecular interaction," Current Opinion in Biotechnology, (1998), 9:97-101.
Flanagan, et al., "Update on the biologic effects of macrophage colony-stimulating factor," Curr Opin Hematol., (1998), 5:181-185.
Franz, et al., "Sulfuranes. X. A Reagent for the Facile Cleavage of Secondary Amides," JACS, (1973), 95(6):2017-2019.
Friesen et al., "Hydroxypropyl Methylcellulose Acetate Succinate-Based Spray-Dried Dispersions: An Overview," Molecular Pharmaceutics, 5(6):1003-1019 (2008).
Furitsu, et al., "Identification of Mutations in the Coding Sequence of the Proto-oncogene c-kit in a Human Mast Cell Leukemia Cell Line Causing Ligand-independent Activation of the c-kit Product," J. Clin. Invest., (1993), 92:1736-1744.
Furuta, et al., "Stem Cell Factor Influences Mast Cell Mediator Release in Response to Eosinophil-Derived Granule Major Basic Protein," Blood, (1998), 92:1055-1061.
Gallop, et al., "Applications of Combinatorial Technologies to Drug Discovery. 1. Background and Peptide Combinatorial Libraries," J. Med. Chem. (1994), 37:1233-1251.
Galofre, et al., "Evaluation and Treatment of Thyroid Nodules: A Clinical Guide," Mt Sinai J Med., (2008), 75:299-311.
Gassman, et al., "Specific Ortho Substitution of Aromatic Heterocyclic Amines," J Am Chem Society, (1973), 95(13):4453-4455.
Ghebre-Sellassie, Isaac; Martin, Charles., Pharmaceuticast Extrusion Technology. Mercer Dekker, Inc., New York. Basel. CRC Press, 2003 p. 238.
Gimbel, et al., "Braf mutations are associated with increased mortality in colorectal cancer," Journal of the American College of Surgeons, (2004), 199:S91-S92.
Girgis, et.al., "The Synthesis of 5-Azaindoles by Substitution-Rearrangement of 7-Azaindoles upon Treatment with Certain Primary Amines," J. Heterocyclic. Chem., (1989), 26:317-325.
Golkar, et al., "Mastocytosis," Lancet, (1997), 349:1379-1385.
Golub, et al., "Molecular Classifcation of Cancer: Class Discovery and Class Prediction by Gene Expression Monitoring," Science, (1999), 286:531-537.
Goodford, P.J., "A Computational Procedure for Determining Energetically Favorable Binding Sites on Biologically Important Macromolecules," J. Med. Chem., (1985), 28:849-857.
Goodsell, et al., "Automated Docking of Substrates to Proteins by Simulated Annealing," Proteins: Structure, Function, and Genetics, (1990), 8:195-202.
Gordon et al., "Detection of Peroxides and Their Removal," The Chemist's Companion: A Handbook of Practical Data, Techniques, and References, (1972), p. 437.
Gordon, et al., "Applications of Combinatorial Technologies to Drug Discovery. 2. Combinatorial Organic Synthesis, Library Screening Strategies, and Future Directions," J. Med. Chem., (1994), 37:1385-1401.

(56) References Cited

OTHER PUBLICATIONS

Gram, H., "Phage Display in Proteolysis and Signal Transduction," Combinatorial Chemistry & High Throughput Screening, (1999), 2:19-28.
Gravert, et al., "Synthesis on Soluble Polymers: New Reactions and the Construction of Small Molecules," Curr Opin Chem Biol., (1997), 1:107-113.
Greer, J., "Model Structure for the Inflammatory Protein C5a," Science, (1985), 228:1055-1060.
Grieco, et al., "PTC is a Novel Rearranged Form of the ret Proto-Oncogene and is Frequently Detected in Vivo in Human Thyroid Papillary Carcinomas," Cell, (1990), 60(4):557-563.
Guida, W., "Software for Structure-Based Drug Design," Current Opinion in Struc. Biol., (1994), 4:777-781.
Hafner, et al., "Isothermal Amplification and Multimerization of DNA by Bst DNA Polymerase," Biotechniques, (2001), 30(4):852-867.
Hallek, et al., "Interaction of the Receptor Tyrosine Kinase p145c-kit with the p210bcr/abl Kinase in Myeloid Cells," Brit. J Haem., (1996), 94:5-16.
Halvorson, et al., "A Blocking Antibody to Nerve Growth Factor Attenuates Skeletal Pain Induced by Prostate Tumor Cells Growing in Bone," Cancer Res., (2005), 65:9426-9435.
Hamel, et al., "The Road Less Traveled: c-kit and Stem Cell Factor," J. Neuro-Onc., (1997), 35:327-333.
Hancock et al., "Characteristics and Significance of the Amorphous State in Pharmaceutical Systems," Journal of Pharmaceutical Sciences 86(1):1-12 (1997).
Hands, et al., "A convenient Method for the Preparation of 5-, 6- and 7-Azaindoles and Their Derivatives," Synthesis, (1996), 877-882.
Hanselman, et al., "A cDNA-Dependant Scintillation Proximity Assay for Quantifying Apolipoprotein A1," J. Lipid Res., (1997), 38:2365-2373.
Hassan, et al., "Expression of Protooncogene c-kit and Its Ligand Stem Cell Factor (SCF) in Gastric Carcinoma Cell Lines," Digest. Dis. Science, (1998), 43:8-14.
Hassan, et al., "Stem Cell Factor as a Survival and Growth Factor in Human Normal and Malignant Hematopoiesis," Acta. Hem., (1996), 95:257-262.
Hayashi, et al., "Dichloro[1,1 19-bis(diphenylophosphino)ferrocene]palladium-(II), an Effective Catalyst for Cross-Coupling of Secondary and Primary Alkyl Grignard and Alkylzinc Reagents with Organic Halides," J. Am. Chem. Soc., (1984), 106:158-163.
Haydock et al., "Analogues of clofibrate and clobuzarit containing fluorine in the side chains," Eur. J. Med. Chem., (1984), 19(3):205-214.
He, et al., "Gamma-secretase activating protein, a therapeutic target for Alzheimer's disease," Nature (2010) 467(7311):95-98.
Heacock, et al., "Orientation and Relative Reaction rate Factors in aromatic Substitution by the Benzensulfonimido Radical," J. Am. Chem. Soc., (1960), 82:3460-3463.
Heim, et al., "Engineering Green Fluorescent Protein for Improved Brightness, Longer Wavelengths and Fluorescence Resonance Energy Transfer," Curr. Biol., (1996), 6:178-182.
Heinrich, et al., "PDGFRA Activating Mutations in Gastrointestinal Stromal Tumors," Science, (2003), 299:708-710.
Heinrich, M. C. et al., "Inhibition of KIT Tyrosine Kinase Activity: A Novel Molecular Approach to the Treatment of KIT-Positive Malignancies," J. Clin. Oncol., vol. 20, No. 6, pp. 1692-1703, Mar. 15, 2002.
Herbst, et al., "Differential Effects of W Mutations on p145c-kit Tyrosine Kinase Activity and Substrate Interaction," J. Biol. Chem., (1992), 267:13210-13216.
Hibi, et al., "Coexpression of the stem cell factor and the c-kit genes in small-cell lung cancer," Oncogene, (1991), 6:2291-2296.
Hirota, et al., "Gain-of-function Mutations of c-kit in Human Gastrointestinal Stromal Tumors," Science, (1998), 279:577-580.
Hoffmann, "m-Trifluoromethylbenzenesulfonyl Chloride," Organic Syntheses, (1981), 60:121-126.
Hogaboam, et al., "Novel Role of Transmembrane SCF for Mast Cell Activation and Eotaxin Production in Mast Cell-Fibroblast Interactions," J. Immunol., (1998), 160:6166-6171.
Holmes, et al., "Long-term effects of Aβ42 immunisation in Alzheimer's disease: follow-up of a randomised, placebo-controlled phase I trail," Lancet (2008) 372:216-233.
Hood, et al., "Tumor Regression by Targeted Gene Delivery to the Neovasculature," Science, (2002), 296: 2404-2407.
Houghten, et al., "Generation and Use of Synthetic Peptide Combinatorial Libraries for Basic Research and Drug Discovery," Nature, (1991), 354:84-86.
Houghten, R., "Parallel Array and Mixture-Based Synthetic Combinatorial Chemistry: Tools for the Next Millennium," Annu Rev Pharmacol Toxicol., (2000), 40:273-282.
Houghten, R., "Peptide Libraries: Criteria and Trends," Trends Genet., (1993), 9:235-239.
Hudson, et al., "A Simple Method for the Determination of Serum Acid Phosphatase," J. Urology, (1947), 58:89-92.
Hughes-Jones, et al., "Synthesis of Rh Fv Phage-Antibodies Using VH and VL Germline Genes," British Journal of Haematology, (1999), 105:811-816.
Iemura, et al., "The c-kit Ligand, Stem Cell Factor, Promotes Mast Cell Survival by Suppressing Apoptosis," Amer. J. Pathol., (1994), 144:321-328.
Inoue, et al., "Coexpression of the c-kit Receptor and the Stem Cell Factor in Gynecological Tumors," Cancer Res., (1994), 54:3049-3053.
International Search Report and Written Opinion of International Application No. PCT/US2004/042470 dated Nov. 25, 2005 (039363-1904).
International Search Report and Written Opinion of International Application No. PCT/US2005/021231 dated Apr. 20, 2006 (039363-2122).
International Search Report and Written Opinion of International Application No. PCT/US2006/018726 dated Apr. 4, 2007 (039363-2193).
International Search Report and Written Opinion of International Application No. PCT/US2006/024361 dated Oct. 24, 2006 (039363-2850).
International Search Report and Written Opinion of International Application No. PCT/US2006/024524 dated Oct. 24, 2006 (039363-2804).
International Search Report and Written Opinion of International Application No. PCT/US2007/083910 dated Jun. 5, 2008 (039363-4101).
International Search Report and Written Opinion of International Application No. PCT/US2007/085289 dated Jun. 5, 2008 (039363-4101A).
International Search Report and Written Opinion of International Application No. PCT/US2007/085299 dated Jul. 28, 2008 (036393-4150).
International Search Report and Written Opinion of International Application No. PCT/US2007/088231 dated Jun. 4, 2008 (039363-3503).
International Search Report and Written Opinion of International Application No. PCT/US2007/088237 dated Jun. 4, 2008 (039363-3550).
International Search Report and Written Opinion of International Application No. PCT/US2007/088243 dated Jun. 5, 2008 (039363-3403).
International Search Report and Written Opinion of International Application No. PCT/US2007/088412 dated Nov. 17, 2008 (039363-3350).
International Search Report and Written Opinion of International Application No. PCT/US2007/088443 dated Jul. 25, 2008 (039363-3303).
International Search Report and Written Opinion of International Application No. PCT/US2010/029489 dated Oct. 5, 2010 (039363-6904).
International Search Report and Written Opinion of International Application No. PCT/US2012/025965 dated May 31, 2012 (039363-7506).

(56) References Cited

OTHER PUBLICATIONS

Isbel, et al., "Local macrophage proliferation correlates with increased renal M-CSF expression in human glomerulonephritis," Nephrol Dial Transplant, (2001), 16:1638-1647.
Ishizaka, et al., "Human ret Proto-Oncogene Mapped to Chromsome 10q11.2," Oncogene, (1989), 4(12):1519-1521.
Isozaki, et al., "Deficiency of c-kit cells in patients with a myopathic form of chronic idiopathic intestinal pseudo-obstruction," Amer. J. of Gast., (1997), 9:332-334.
Ivanisevic et al., "Uses of X-Ray Powder Diffraction in the Pharmaceutical Industry," Pharm Sci Encyc:DDDM, (2010), 1-42.
Iwane, et al., "Myosin Subfragment-1 is Fully Equipped with Factors Essential for Motor Function," Biochem. and Biophys. Res. Comm., (1997), 230:76-80.
Izquierdo, et al., "Differential Expression of the c-kit Proto-Oncogene in Germ Cel Tumours," J. Pathol., (1995), 177:253-258.
Jarugula, et al., "Nonlinear Pharmacokinetics of 5-Fluorouracil in Rats," J Pharm Sci., (1997), 86(6):756-757.
Jensen, et al., "Pharmacological targeting of the KIT growth factor receptor: a therapeutic consideration for mast cell disorders," Brit J Pharmacology, (2008), 154:1572-1582.
Jing, et al., "GDNF-Induced Activation of the Ret Protein Tyrosine Kinase is Mediated by GDNFR-a, a Novel Receptor for Gdnf," Cell, (1996), 85:1113-1124.
Johann, et al., "GLVR1, a Receptor for gibbon Ape Leukemia Virus, Is Homologous to a Phosphate Permease of Neurospora crassa and is Expressed at High Levels in the Brain and Thymus," J. Virol., (1992), 66:1635-1640.
Johnston, M., "Gene Chips: Array of hope for understanding gene regulation," Curr. Biol., (1998), 8:R171-R174.
Jones, et al., "Antiestrogens. 2. Structure-Activity Studies in a Series of 3-Aroyl-2-arylbenzo[b]thiophene Derivatives Leading to [6-Hydroxy-2-(4-hydroxyphenyl)benzo(b)thien-3-yl](4-[2-(1-piperidinyl)ethoxy]-phenyl]methanone Hydrochloride (LY156758), a Remarkably Effective Estrogen Antagonist with Only Minimal Intrinsic Estrogenicity," J. Med. Chem. (1984), 27(8):1057-1066.
Jones, R., "Biology and Treatment of Chronic Myeloid Leukemia," Curr. Opin. Onc., (1997), 9:3-7.
Jones, T., "Interactive Computer Graphics: FRODO," Methods in Enzymology, (1985), 115:157-171.
Jose, et al., "Blockade or Macrophage colony-Stimulating Factor Reduces Macrophage Proliferation and Accumulation in Renal Allograft Rejection," Am J Transplant, (2003), 3(3):294-300.
Joseph-McCarthy, D., "Computational Approaches to Structure-Based Ligand Design," Pharmacology & Therapeutics, (1999), 84:179-191.
Kahl, et al., "A Multiple-Approach Scintillation Proximity Assay to Measure the Association Between Ras and Raf," Anal. Biochem., (1996), 243:282-283.
Kassel, et al., "Local increase in the Number of mast cells and expression of nerve growth factor in the bronchus of asthmatic patients after repeated inhalation of allergen at low-dose," Clin. Exp. Allergy, (2001), 31:1432-1440.
Katritzky, et al., "Regiospecific C-Acylation of Pyrroles and Indoles Using N-Acylbenzotriazoles," J. Org. Chem., (2003), 68:5720-5723.
Kay, et al., "Eosinophils and Eosinophil-Associated Cytokines in Allergic Inflammation," Int. Arch. Aller. Immunol., (1997), 113:196-199.
Kern, et al., "Direct Hybridization of Large-Insert Genomic Clones on High-Density Gridded cDNA Filter Arrays," Biotechniques, (1997), 23:120-124.
Kim, et al., "A Merger of Rational Drug Design and Combinatorial Chemistry: Development and Application of Peptide Secondary Structure Mimetics," Combinatorial Chemistry & High Throughput Screening, (2000), 3:167-183.
Kim, et al., Database CAS on STN (Columbus, OH, USA) No. 138:55974, Preparation of 2-anilino-4-indolyl pyrimidines as tyrosine kinase inhibitors, abstract, 2002) see whole article.
Kinashi, et al., "Steel Factor and c-kit Cell-Matrix Adhesion," Blood, (1994), 83:1033-1038.

Kirkpatrick, et al., "Structure-Based Drug Design: Combinatorial Chemistry and Molecular Modeling," Combinatorial Chemistry & High Throughput Screening, (1999), 2:211-221.
Kitamura, et al., "Synthesis of Quinolines and 2H-Dihydropyrroles by Nucleophilic Substitution at the Nitrogen Atom of Oxime Derivatives," Synthesis, (2003), 15:2415-2426.
Kline, et al., "Studies by 1H Nuclear Magnetic Resonance and Distance Geometry of the Solution Conformation of the x-Amylase Inhibitor Tendamistat," J. Mol. Biol., (1986), 189:377-382.
Knighton, et al., "Structural Basis of the Intrasteric Regulation of Myosin Light Chain Kinases," Science, (1992), 258:130-135.
Kodama, et al., "Congenital Osteoclast Deficiency in Osteopetrotic (op/op) Mice Is Cured by Injections of Macrophage colony-stimulating Factor," J. Exp,. Med.,(1991), 173:269-272.
Kolaskar, et al., "A Semi-Empirical Method for Prediction of Antigenic Determinants on Protein Antigens," FEBS Lett., (1990), 276:172-174.
Komoyira, et al., "Design, synthesis and biological activity of amidinobicyclic compounds (derivatives of DX-9065a) as a factor Xa inhibitors: SAR study of S1 and aryl binding sites," Bioorg. Med. Chem., (2004), 12: 2099-2114.
Kondoh, et al., "An in vivo model for receptor tyrosine kinase autocrine/paracrine activation: auto-stimulated Kit receptor acts as a tumor promoting factor in papillomavirus-induced tumorigenesis," Oncogene, (1995), 10:341-347.
Kondoh, et al., "Establishment and Further Characterization of a Line of Transgenic Mice Showing Testicular Tumorigenesis at 100% Incidence," J. Urol., (1994), 152:2151-2154.
Kondoh, et al., "Very High Incidence of Germ Cell tumorigenesis (Seminomagenesis) in Human Papillomavirus Type 16 Transgenic Mice," J. Virol., (1991), 65:3335-3339.
Konishi, et al., "Overexpression of leucocyte common antigen (LAR) P-subunit in thyroid carcinomas," Brit J Cancer, (2003), 88:1223-1228.
Konno et al., "Influence of Different Polymers on the Crystallization Tendency of Molecularly Dispersed Amorphous Felodipine," Journal of Pharmaceutical Sciences 95(12):2692-2705 (2006).
Kroll, et al., "A Malfunctional Prokaryotic Protein Expression System: Overproduction, Affinity Purification, and Selective Detection," DNA Cell. Biol., (1993), 12:441-453.
Kundu, et al., "Combinatorial Chemistry: Polymer Supported Synthesis of Peptide and Non-Peptide Libraries," Progress in Drug Research, (1999), 53:89-156.
Kunisada, et al., "Murine Cutaneous Mastocytosis and Epidermal Melanocytosis Induced by Keratinocyte Expression of Transgenic Stem Cell Factor," J. Exp. Med., (1998), 187:1565-1573.
Kunkel, T., "Rapid and Efficient Site-Specific Mutagenesis Without Phenotypic Selection," Methods in Enzymology, (1987), 154:367-382.
Kunnimalaiyaan, et al., "The Raf-1 pathway: a molecular target for treatment of select neuroendocrine tumors?" Anticancer Drugs, (2006), 17(2):139-42.
Kuntz, et al., "A Geometric Approach to Macromolecule-Ligand Interactions," J. Mol. Biol., (1982), 161:269-288.
Kuntz, et al., "Structure-Based Molecular Design," Acc. Chem. Res., (1994), 27:117-123.
Lahm, et al., "Interleukin 4 Down-Regulates Expression of c-kit and Autocrine Stem Cell Factor in Human Colorectal Carcinoma Cells," Cell Growth & Differ., (1995), 6:1111-1118.
Lala, et al., "Role of nitric oxide in tumor progression: Lessons from experimental tumors," Cancer and Metastasis Reviews, (1998), 17:91-106.
Lam, et al., "A new type of synthetic peptide library for identifying ligand-binding activity," Nature, (1991), 354: 82-84.
Langham et al., "Metalation and Halogen-Metal Interconversion Reactions of Some Halogenated Phenyl Ethers," J. of the Am. Chem. Society, (1941), 63:545-549.
Lawicki, et al., "The pretreratment plasma level and disgnostic utility of M-CSF in benign breast tumor and breast cancer patients," Clinica Chimica Acta., (2006), 371:112-116.
Le Meur, et al., "Macrophage accumulation at a site of renal inflammation is dependent on the M-CSF/c-fms pathway," J Leukocyte Biology, (2002), 72:530-537.

(56) References Cited

OTHER PUBLICATIONS

Lebl, et al., "One-Bead-One-Structure Combinatorial Libraries," Biopolymers, (1995), 37:177-198.

Lee, et al., "HLA-DR-Triggered Inhibition of Hemopoiesis Involves Fas/Fas Ligand Interactions and is Prevented by c-kit Ligand," J. Immunol., (1997), 159:3211-3219.

Lee, et al., "Mast Cells: A Cellular Link Between Autoantibodies and Inflammatory Arthritis," Science, (2002), 297:1689-1692.

Leuner, et al., "Improving drug solubility for oral delivery using solid dispersions," European Journal of Pharma. And Biopharma., (2000), 50(1):47-60.

Levin, et al., "Neoplasms of the Central Nervous System," Cancer Principles & Practice of Oncology, (1997), 2:2022-2082.

Li, et al., "Abrogation of c-kit/Steel Factor-Dependent Tumorigenesis by Kinase Defective Mutants of the c-kit Receptor: c-kit Kinase Defective Mutants as Candidate Tools for Cancer Gene Therapy," Canc. Res., (1996), 56:4343-4346.

Libby, P., "Inflammation in atherosclerosis," Nature, (2002), 420:868-874.

Liparoto, et al., "Biosensor Analysis of the Interleukin-2 Receptor Complex," Journal of Molecular Recognition, (1999), 12:316-321.

Lipinski, et al., "Experimental and Computational Approaches to Estimate Solubility and Permeability in Drug Discovery and Development Settings," Advanced Drug Delivery Reviews, (1997), 23:3-25.

Lipschultz, et al., "Experimental design for analysis of complex kinetics using surface plasmon resonance," Methods, (2000), 20(3):310-318.

Liu, et al., "Sorafenib Blocks the RAF/MEK/ERK Pathway, Inhibits Tumor Angiogenesis, and Induces Tumor Cell Apoptosis in Hepatocellular Carcinoma Model PLC/PRF/5," Cancer Res., (2006), 66:11852-11858.

London, et al., "Expression of Stem Cell Factor Receptor (c-kit) by the Malignant Mast Cells from Spontaneous Canine Mast Cell Tumors," J. Compar. Pathol., (1996), 115:399-414.

Longley, et al., "Altered Metabolism of Mast-cell Growth Factor (c-kit Ligand) in Cutaneous Mastocytosis," New Engl. J. Med., (1993), 328:1302-1307.

Longley, et al., "Chymase Cleavage of Stem Cell Factor Yields a Bioactive Soluble Product," Proc. Natl. Acad. Sci., (1997), 94:9017-9021.

Longley, et al., "Somatic c-Kit Activating Mutation in Urticaria Pigmentosa and Aggressive Mastocytosis: Establishment of Clonality in a Human Mast Cell Neoplasm," Nat. Gen., (1996), 12:312-314.

Loveland, et al., "Stem Cell Factor and c-kit in the Mammalian Testis: Lessons Originating from Mother Nature 19s Gene Knockouts," J. Endocrinol., (1997), 153:337-344.

Lu, et al., "Oriented Immobilization of Fab 19 Fragments on Silica Surfaces," Anal. Chem., (1995), 67:83-87.

Lukacs, et al., "Stem Cell Factor (c-kit Ligand) Influences Eosinophil Recruitment and Histamine Levels in Allergic Airway Inflammation," J. Immunol., (1996), 156:3945-3951.

Luo, et al., "Close Linkage with the RET Proto-Oncogene and Boundaries of Deletion Mutations in Autosomal Dominant Hirschsprung Disease," Hum Mol Genet., (1993), 2(11):1803-1808.

Lyman, et al., "c-kit Ligand and Flt3 Ligand: Stem/Progenitor Cell Factors With Overlapping Yet Distinct Activities," Blood, (1998), 91:1101-1134.

Ma, et al., "Indolinone Derivatives Inhibit Constitutively Activated KIT Mutants and Kill Neoplastic Mast Cells," J Invest Dermatol., (2000), 114:392-394.

Ma, et al., "The c-Kit Mutation Causing Human Mastocytosis is Resistant to ST1571 and Other KIT Kinase Inhibitors; Kinases with Enzymatic Site Mutations Show Different Inhibitor Sensitivity Profiles Than Wild-type Kinases and Those With Regulatory-Type Mutations," Blood, (2002), 99:1741-1744.

Machens, et al., "Modification of multiple endocrine neoplasia 2A phenotype by cell membrane proximity of RET mutations in exon 10," Endocrine-Related Cancer, (2009), 16:171-177.

Machida, et al., "Mitogen-activated Protein Kinase Kinase Kinase Kinase 4 as a Putative Effector of Rap2 to Activate the c-Jun N-terminal Kinase," J. Biol. Chem., (2004), 279:15711-15714.

Mack, et al., "Functional identification of kinases essential for T-cell activation through a genetic suppression screen," Immunol. Lett., (2005), 96:129-145.

Madden, et al., "Synthetic Combinatorial Libraries: Views on Techniques and Their Application," Perspectives in Drug Discovery and Design, (1994), 2:269-285.

Malmborg, et al., "BIAcore As a Tool in Antibody Engineering," Journal of Immunological Methods, (1995), 183:7-13.

Malmqvist, et al., "Biomolecular Interaction Analysis: Affinity Biosensor Technologies for Functional Analysis of Proteins," Current Opinion in Chemical Biology, (1997), 1:378-383.

Malmqvist, M., "BIACORE: An Affinity Biosensor System for Characterization of Biomolecular Interactions," Biochemical Society Transactions, (1999), 27:335-340.

Markiewicz, et al., "Synthetic Oligonucleotide Combinatorial Libraries and Their Applications," II Farmaco, (2000), 55:174-177.

Martin, Y., "Computer-Assisted Rational Drug Design," Methods Enz., (1991), 203:587-613.

Matayoshi, et al., "Actions of brain-derived neurotrophic factor on spinal nociceptive transmission during inflammation in the rat," J Physiol., (2005), 569:685-95.

Matsumoto, et al., "Physical properties of solid molecular dispersions of indomethacin with poly(vinylpyrrolindone) and poly(vinylpyrrolidone-co-vinyl-acetate) in relation to indomethacin crystallization," Pharmaceutical Research, (1999), 16(11):1722-1728.

Mazeas, et. al., "Synthesis of new melatoninergic ligands including azaindole moiety," Heterocycles, (1999), 50:1065-1080.

McCall, et al., "Characterization of Anti-Mouse FcγRII Single-Chain Fv Fragments Derived from Human Phage Display Libraries," Immunotechnology, (1998), 4:71-87.

McPherson, A., "Current Approaches to Macromolecule Crystallization," Eur. J. Biochem., (1990), 189:1-23.

Mekori, et al., "The Role of c-Kit and Its Ligand, Stem Cell Factor, in Mast Cell Apoptosis," Int. Arch. Allergy Immunol., (1995), 107:136-138.

Mekori, et al., "Transforming Growth Factor-βPrevents Stem Cell Factor-Mediated Rescue of Mast Cells from Apoptosis After IL-3 Deprivation," J. Immunol., (1994), 153:2194-2203.

Meltzer, E. O., "The pharmacological basis for the treatment of perennial allergic rhinitis and non-allergic rhinitis with topical corticosteroids," Aller., (1997), 52:33-40.

Meng, et al., "Automated Docking with Grid-Based Energy Evaluation," J. Compt. Chem., (1992), 13:505-524.

Merour, et al., "Synthesis and Reactivity of 7-Azaidoles (1H-Pyrrolo[2,3-b]pyridine)," Curr. Org. Chem., (2001), 5:471-506.

Merritt, A., "Solution Phase Combinatorial Chemistry," Comb Chem High Throughput Screen, (1998), 1:57-72.

Metcalf, D., "Lineage Commitment in the Progeny of Murine Hematopoietic Prepogenitor Cells: Influence of Thrombopoietin and Interleukin 5," Proc. Natl. Acad. Sci., (1998), 95:6408-6412.

Metcalfe, D. "Classification and Diagnosis of Mastocytosis: Current Status," J. Invest. Derm., (1991), 93:2S-4S.

Metcalfe, et al., "Mast Cells," Physiol. Rev., (1997), 77:1033-1079.

Meula Pomeda, et al., "Efecto De Codisolventes Y Dispersiones Solida De Polivinilpirrolidona K-30 En La Solubilidad Tel Tiabendazol," Departamento de Farmacia y Tecnologia Farmaceutica. Facultad de Farmacia. Universidad de Alcala, pp. 85-87 (2002) (No English Translation Available).

Miller et al., "FLOG: A System to Select Quasi-Flexible Ligands Complementary to a Receptor of Known Three-Dimensional Structure," J. Comp. Aided Molec. Design, (1994), 8:153-174.

Minakata, et al., "Functionalization of 1H-Pyrrolo[2,3-b]pyridine," Bulletin of the Chemical Society of Japan, (1992), 65(11):2992-2997.

Minakata, et al., "Regioselective Funtionalization of 1H-Pyrrolo[2,3-b]pyridine Via its N-Oxide," Synthesis, (1992), 661-663.

Miranker, at al., "Functionality Maps of Binding Sites: A Multiple Copy Simultaneous Search Method," Proteins: Structure, Function, and Genetics, (1991), 11:29-34.

(56) References Cited

OTHER PUBLICATIONS

Mitra, et al., "Fluorescence Resonance Energy Transfer Between Blue-Emitting and Red-Shifted Excitation Derivatives of the Green Fluorescent Protein," Gene, (1996), 173:13-17.
Miyaura, et al., "Palladium-Catalyzed Cross-Coupling Reactions of Organoboron Compounds," Chem. Rev., (1995), 95:2457-2483.
Mokhtari, et al., "Potential utility of small tyrosine kinase inhibitors in the treatment of diabetes," Clinical Science, (2010), 118(4):241-247.
Mol, et al., "Structural Basis for the Autoinhibition and STI-571 Inhibition of c-Kit Tyrosine Kinase," J. Biol. Chem., (2004), 279:31655-31663.
Mol, et al., "Structure of a c-Kit Product Complex Reveals the Basis for Kinase Transactivation," J. Biol. Chem., (2003), 278:31461-31464.
Morgan, et al., "Isolation and Characterization of a Cloned Growth Factor Dependent Macrophage Cell Line, BAC1.2F5," J. Of Cell. Physiology, (1987), 130:420-427.
Motoyoshi, K., "Biological activities and clinical application of M-CSF," Int J Hematol. (1998), 67:109-122.
Murty, et al., "A Genetic Perspective of Male Germ Cell Tumors," Sem. Oncol., (1998), 25:133-144.
Naclerio, et al., "Rhinitis and Inhalant Allergens," JAMA, (1997), 278:1842-1848.
Nagafuji, et al., "A General Synthesis of Pyrroles and Fused Pyrrole Systems from Ketones and Amino Acids," J. Org. Chem., (1996), 61:4999-5003.
Nagata, et al., "Elevated Expression of the Proto-Oncogene c-kit in Patients with Mastocytosis," Leukemia, (1998), 12:175-181.
Nahm et al., "N-Methoxy-N-Methylamides as Effective Acylating Agents," Tetrahedron Lett., (1981), 22(39):3815-3818.
Nakagawara, et al., "Expression and Function of TRK-B an BDNF in Human Neuroblastomas," Mol. Cell Biol., (1994), 14:759-767.
Nakai et al., "New Potent Antagonists of Leukotrienes C4 and D4. 01. Synthesis and Structure-Activity Relationships," J. Med. Chem., (1988), 31:(1):84-91.
Nassentein, et al., "The Neurotrophins Nerve Growth Factor, Brain-derived Neurotrophic Factor, Neurotrophin-3, and Neurotrophin-4 Are Survival and Activation Factors for Eosinophils in Patients with Allergic Bronchial Asthma," J. Exp. Med., (2003), 198:455-467.
Natal!, et al., "Breast cancer is associated with loss of the c-kit oncogene product," Int. J. Cancer (1992) 52:713-717.
Navaza, J., "AMoRe: an Automated Package for Molecular Replacement," Acta Cryst., (1994), A50:157-163.
Neidle, et al., "Molecular Modeling to Study DNA Intercalation by Anti-Tumor Drugs," Methods Enz., (1991), 203:433-458.
Ng, et al., "Engineering Protein-Lipid Interactions: Targeting of Histidine-Tagged Proteins to Metal-Chelating Lipid Monolayers," Langmuir, (1995), 11:4048-4055.
Nicholls, et al., "Protein Folding and Association: Insights From the Interfacial and Thermodynamic Properties of Hydrocarbons," Proteins, (1991), 11:281-296.
Nichols, et al., "Development of a Scintillation Proximity Assay for Peroxisome Proliferator-Activated Receptor y Ligand Binding Domain," Anal. Biochem., (1998), 257:112-119.
Niihori, et al., "Germline KRAS and BRAF mutations in cardio-facio-cutaneous syndrome," Nature Genet., (2006), 38(3):294-296.
Ochs, et al., "A phase I/II trial of recombinant methionyl human brain derived neurotrophic factor administered by intrathecal infusion to patients with amyotrophic lateral sclerosis," Amyotroph Lateral Scler Other Motor Neuron Disord., (2000), 1:201-206.
Okada, et al., "Gene Therapy Against an Experimental Glioma Using Adeno-Associated Virus Vectors," Gene Ther., (1996), 3:957-964.
Okayama, et al., "Activation of Eosinophils with Cytokines Produced by Lung Mast Cells," Int. Arch. Aller. Immunol., (1997), 114(suppl. 1):75-77.
Okayama, et al., "Human Lung Mast Cells are Enriched in the Capacity to Produce Granulocyte-Macrophage Colony-Stimulating Factor in Response to IgE-Dependent Stimulation," Eur. J. Immunol., (1998), 28:708-715.

Olah, et al., "Synthetic Methods and Reactions: Part 209. Improved Preparation of Aldehydes and Ketones from N,N-Dimethylamides and Grignard Reagents," Synthesis, (1984), 228-230.
O'Shannessy, D., "Determination of Kinetic Rate and Equilibrium Binding Constants for Macromolecular Interactions: a Critique of the Surface Plasmon Resonance Literature," Current Opinions in Biotechnology, (1994), 5:65-71.
O'Shannessy, et al., "Interpretation of Deviations From Pseudo-First-Order Kinetic Behavior in the Characterization of Ligand Binding by Biosensor Technology," Analytical Biochemistry, (1996), 236:275-283.
Ottoni, et al., "Efficient and Simple Methods for the Introduction of the Sulfonyl, Acyl and Alkyl Protecting Groups on the Nitrogen of Indole and its Derivatives," Tetrahedron, (1998), 54:13915-13928.
Otwinowski, Z., "Maximum Likelihood Refinement of Heavy Atom Parameters," Dept. of Molecular Biophysics and Biochemistry, (1991), 80-86.
Owicki, et al., Application of Fluorescence Polarization Assays in High-Throughput Screening, Genetic Engineering News, (1997), 17:27.
Parker, et al., "Development of High Throughput Screening Assays Using Fluorescence Polarization: Nuclear Receptor-Ligand-Binding and Kinase/Phosphatase Assays," J Biomol Screen, (2000), 5:77-88.
Patani et al, "Bioisosterism: a rational approach in drug design," Chem Rev, (1996), 96:3147-3176.
Perrin, D., "Nucleic Acids for Recognition and Catalysis: Landmarks, Limitations, and Looking to the Future," Combinatorial Chemistry & High Throughput Screening, (2000), 3:243-269.
Petty, et al., "The effect of systemically administered recombinant human nerve growth factor in healthy human subjects," Ann Neurol., (1994), 36:244-246.
Pflugrath, et al., "Crystal Structure Determination, Refinement and the Molecular Model of the x-Amylase Inhibitor Hoe-467A," J. Mol. Biol., (1986), 189:383-386.
Pierce, et al., "Local anesthetics. I. beta-Monoaklylaminoethyl Esters of Alkoxybenzoic Acids," J. Am. Chem. Soc., (1942), 64:1691-1694.
Pignon, J.M., "C-kit mutations and mast cell disorders a model of activating mutations of growth factor receptors," Hermatol Cell Ther., (1997), 39:114-116.
Plunkett, et al., "A Silicon-Based Linker for Traceless Solid-Phase Synthesis," J. Org. Chem., (1995), 60:6006-6007.
Poul, et al., "Selection of Tumor-Specific Internalizing Human Antibodies from Phage Libraries," J. Mol. Biol., (2000), 301:1149-1161.
Price, et al., "Summary report on the ISOBM TD-4 Workshop: analysis of 56 monoclonal antibodies against the MUC1 mucin," Tumour Biology, (1998), 19:1-20.
Qiao, et. al., "Role of Macrophage Colony-Stimulating Factor in Atherosclerosis," Am. J. Path., (1997), 150:1687-1699.
Rajavashisth, et. al., "Heterozygous Osteopetrotic (op) Mutation Reduces Atherosclerosis in LDL Receptor-deficient Mice," J. Clin. Invest., (1998), 101:2702-2710.
Rajpert-De Meyts, et al., "Expression of the c-kit Protein Product in Carcinoma-in-situ and Invasive Testicular Germ Cell Tumours," Int. J. Androl., (1994), 17:85-92.
Rapp, et al., "Raf kinases in lung tumor development," Advan. Enzyme Regul. (2003) 43:183-195.
Remington: The Science and Practice of Pharmacy, vol. II, pp. 1454-1460 (1995).
Ricotti, et al., "c-kit Is Expressed in Soft Tissue Sarcoma of Neuroectodermic Origin and Its Ligand Prevents Apoptosis of Neoplastic Cells," Blood, (1998), 91:2397-2405.
Ridge, et al., "FMS mutations in myelodysplastic, leukemic, and normal subjects," Proc. Nat. Acad. Sci., (1990), 87:1377-1380.
Roberts et al., "Targeting the Raf-MEK-ERK mitogen-activated protein kinase cascade for the treatment of cancer," Oncogene (2007) 26:3291-3310.
Roberts, et al., "Generation of an antibody with enhanced affinity and specificity for its antigen by protein engineering," Nature, (1987), 328:731-734.
Robinson, et al., "Stimulation of Bone Marrow Colony Growth in Vitro by Human Urine," Blood, (1969), 33:396-399.

(56) References Cited

OTHER PUBLICATIONS

Robison, et al., "7-Azaindole. I. Synthesis and Conversion to 7-Azatryptophan and Other Derivatives," J. Am. Chem. Soc., (1955), 77:457-460.
Rodan, et al., "Therapeutic Approaches to Bone Diseases," Science, (2000), 289:1508-1514.
Rodriguez-Viciana, et al., "Germline Mutations in Genes Within the MAPK Pathway Cause Cardio-facio-cutaneous Syndrome," Science, (2006), 311:1287-1290.
Rosenfeld, M.A., "Human artificial chromosomes get real," Nat. Genet., (1997), 15:333-335.
Ryan, et al., "Role for the Stem Cell Factor/KIT Complex in Schwann Cell Neoplasia and Mast Cell Proliferation Associated with Neurofibromatosis," J. Neuro. Res. (1994), 37:415-432.
Saify, et al., "Database CAS on STN (Columbus, OH, USA) No. 124:170379, Synthesis of some 2-azaindole derivatives: their cyctotoxicity and antibacterial activity," abstract, (1996), See RN 271-63-6.
Saify, et al., "Synthesis of some 7-azaindole derivatives: Their cytotoxicity and antibacterial activity," Pakistan Journal of Scientific and Industrial Research, (1994), 37(10):439-441.
Saiki, R.K., "Amplification of Genomic DNA," Pcr Protocols, a Guide to Methods and Applications, (1990), 13-20.
Sambrook, et al., "Introduction of Recombinant Vectors into Mammalian Cells," Molecular Cloning: A Laboratory Manual, (1989), 2:16.30-16.37.
Sandlow, et al., "Expression of c-Kit and its Ligand, Stem Cell Factor, in Normal and Subfertile Human Testicular Tissue," J. Androl., (1996), 17:403-408.
Santoro, et al., "The ret Proto-Oncogene is Consistently Expressed in Human Pheochromocytomas and Thyroid Medullary Carcinomas," Oncogene, (1990), 5(10):1595-1598.
Sathornsumetee, et al., "AAL881, a Novel Small Molecule Inhibitor of RAF and Vascular Endothelial Growth Factor Receptor Activities, Blocks the Growth of Malignant Glioma," Cancer Res., (2006), 66:8722-8730.
Sawada, et al., "4-(Benzoylindolizinyl)butyric acids; Novel nonsteroidal inhibitors of steroid 5;1-reductase. III," Chemical and Pharmaceutical Bulletin, (2001), 49(7):799-813.
Sawada, et al., "Role of Cytokines in Leukemic type Growth of Myelodysplastic CD34+ Cells," Blood, (1996), 88:319-327.
Sawai, et al., "Aberrant growth of granulocyte-macrophage progenitors in juvenile chronic myelogenous leukemia in serum-free culture," Exp. Hem., (1996), 2:116-122.
Scheffner, et al., "The E6 Oncoprotein Encoded by Human Papillomavirus Types 16 and 18 Promotes the Degredation of p53," Cell, (1990), 63:1129-1136.
Schiemann, et al., "p-Fluorobenzoic Acid," Org. Syn. Coll., (1943), 2:299-301.
Schneider, et al., "Functional Purification of a Bacterial ATP-Binding Cassette Transporter Protein (MaIK) from the Cytoplasmic Fraction of an Overproducing Strain," Protein Expr. Purif., (1995), 6:10-14.
Schneller, et. al., "Synthesis of 4-Amino-1 H-pyrrolo[2,3-b]pyridine {1,7-Dideazaadenine) and 1H-Pyrrolo[2,3-b]pyridine-4-ol (1,7-Dideazahypoxanthine)," J. Org. Chem., (1980), 45:4045-4048.
Schuhmann, et al., "Immobilization of Enzymes on Langmuir-Blodgett Films via a Membrane-Bound Receptor. Possible Applications for Amperometric Biosensors," Adv. Mater., (1991), 3:388-391.
Schummer, et al., "Inexpensive Handheld Device for the Construction of High-Density Nucleic Acid Arrays," Biotechniques, (1997), 23:1087-1092.
Schweizer, et al., "Combinatorial Synthesis of Carbohydrates," Curr Opin Chem Biol, (1999), 3(3):291-298.
Sclabas, et al., "Overexpression of Tropomyosin-Related Kinase B in Metastatic Human Pancreatic Cancer Cells," Clin. Cancer. Res., (2005), 11:440-449.
Search Report for European Application No. 04814626.0 dated Aug. 4, 2009 (039363-1907).
Search Report for European Application No. 11173701.1 dated Mar. 6, 2012 (039363-2894).
Search Report for European Application No. 11173701.1 dated Oct. 26, 2011 (039363-2894).
Secor, et al., "Mast cells are essential for early onset and severe disease in a murine model of multiple sclerosis," J. Exp. Med., (2000), 5:813-821.
Selvin, P., "Fluorescence Resonance Energy Transfer," Meth. Enzymol., (1995), 246:300-345.
Shah et al., "Improved Human Bioavailability of Vemurafenib, a Practically Insoluble Drug, Using an Amorphous Polymer-Stabilized Solid Dispersion Prepared by a Solvent-Controlled Coprecipitation Process", Journal of Pharmceutical Sciences, 2012, pp. 1-15.
Shah et al., "Development of Novel Microprecipitated Bulk Power(MBP) Technology for Manufacturing Stable Amorphous Formulations of Poorly Soluble Drugs", International Journal of Pharmaceutics, vol. 438, 2012, pp. 53-60.
Shan, et al., "Prodrug strategies based on intramolecular cyclization reactions," Journal of Pharmaceutical Sciences, (1997), 86(7):765-767.
Sheets, et al., "Efficient Construction of a Large Nonimmune Phage Antibody Library: The Production of High-Affinity Human Single-Chain Antibodies to Protein Antigens," Proc Natl Acad Sci USA., (1998), 95:6157-6162.
Shibata, et al., "Alveolar macrophage deficiency in osteopetrotic mice deficient in macrophage colony-stimulating factor is spontaneously corrected with age and associated with matrix metalloproteinase expression and emphysema," Blood, (2001), 98:2845-2852.
Siegel, et al., "Mass Spectral Analysis of a Protein Complex Using Single-Chain Antibodies Selected on a Peptide Target: Applications to Functional Genomics," Journal of Molecular Biology, (2000), 302:285-293.
Sigal, et al., "A Self-Assembled Monolayer for the Binding and Study of histidine-Tagged Proteins by Surface Plasmon Resonance," Anal. Chem., (1996), 68:490-497.
Smalley, et al., "c-Kit signaling as the driving oncogenic event in sub-groups of melanomas," Histol Histopathol, (2009), 24:643-650.
Solinas-Toldo, et al., "Matrix-Based Comparative Genomic Hybridization Biochips to Screen for Genomic Imbalances," Genes, Chromosomes & Cancer, (1997), 20:399-407.
Song, et al., "Isomerism of Bis(7-azaindolyl)methane," Organic Letters (2002), 4(23):4049-4052, Table of content p. 1-16 and Supporting information p. 1-15.
Sperling, et al., "Expression of the Stem Cell Factor Receptor C-Kit (CD117) in Acute Leukemias," Haemat., (1997), 82:617-621.
Stanulla, et al., "Coexpression of Stem Cell Factor and Its Receptor c-Kit in Human Malignant Glioma Cell Lines," Act Neuropath., (1995), 89:158-165.
Steinman, L., "Multiple sclerosis: A coordinated immunological attack against myelin in the central nervous system," Cell, (1996), 85:299-302.
Strohmeyer, et al., "Expression of the C-kit Proto-Oncogene and its Ligand Stem Cell Factor (SCF) in Normal and Malignant Human Testicular Tissue," J. Urol., (2005), 153:511-515.
Strohmeyer, et al., "Expression of the hst-1 and c-kit Protooncogenes in Human Testicular Germ Cell Tumors," Canc. Res., (1991), 51:1811-1816.
Su, et al., "Synthesis of bromo-substituted Idoxyl Esters for Cytochemical Demonstration of Enzyme Activity," J. Am. Chem. Soc., (1960), 82:1187-1189.
Sun, C., "Recent Advances in Liquid-Phase Combinatorial Chemistry," Comb. Chem. & High Throughput Screening, (1999), 2:299-318.
Sun, et al., "Design, Synthesis, and Evaluations of Substituted 3-[(3- or 4-Carboxyethylpyrrol-2-yl) Methylidenyl]indolin-2-Ones as Inhibitors of VEGF, PGF, and PDGF Receptor Tyrosine Kinases," J. Med. Chem., (1999), 42:5120-5130.
Tada, et al., "Analysis of Cytokine Receptor Messenger RNA Expression in Human Glioblastoma Cells and Normal Astrocytes by Reverse-Transcription Polymerase Chain Reaction," J. Neuro., (1994), 80:1063-1073.
Takahashi, et al., "Activation of a Novel Human Transforming Gene, ret, by DNA Rearrangement," Cell, (1985), 42(2):581-588.

(56) References Cited

OTHER PUBLICATIONS

Takahashi, et al., "Cloning and Expression of the ret Proto-Oncogene Encoding a Tyrosine Kinase with Two Potential Transmembrane Domains," Oncogene, (1988), 3(5):571-578.
Takahashi, et al., "ret Transforming Gene Encodes a Fusion Protein Homologous to Tyrosine Kinases," Mol Cell Biol., (1987), 7:1378-1385.
Tang, et al., "An RNA interference-based screen identifies MAP4K4/NIK as a negative regulator of PPARy, adipogenesis, and insulin-responsive hexose transport," Proc. Natl. Acad. Sci., (2006), 103:2087-2092.
Tanno et al., "Evaluation of Hypromellose Acetate Succinate (HPMCAS) as a Carrier in Solid Dispersions," Drug Development and Industrial Pharmacy 30(1):9-17 (2004).
Taylor, et al., "The Rapid Generation of Oligonucleotide-directed Mutations at High Frequency Using Phosphorothioate-Modified DNA," Nucl. Acids Res., (1985), 13:8764-8785.
Teitelbaum, S.L., "Bone Resorption by Osteoclasts," Science, (2000), 289:1504-1508.
Thibault, et. al., "Concise and Efficient Synthesis of 4-fluoro-1H-pyrrolo[2,3-b] pyridine," Org. Lett., (2003), 5:5023-5025.
Thomas, et al., "The Eosinophil and its Role in Asthma," Gen. Pharmac., (1996), 27:593-597.
Thomas, et. al., "Light-Emitting Carbazole Derivatives: Potential Electroluminescent Materials," J. Am. Chem. Soc., (2001), 123:9404-9411.
Toste, et al., "A Versatile Procedure for the Preparation of Aryl Thiocyanates Using N-Thiocyanatosuccinimide (NTS)," Synth. Comm., (1995), 25(8):1277-1286.
Toyota, et al., "Expression of c-kit and kit Ligand in Human Colon Carcinoma Cells," Turn Biol., (1993), 14:295-302.
Trupp, et al., "Functional Receptor for GDNF Encoded by the c-ret Proto-Oncogene," Nature., (1996), 381:785-789.
Tsujimura, et al., "Ligand-Independent Activation of c-kit Receptor Tyrosine Kinase in a Murine Mastocytoma Cell Line P-815 Generated by a Point Mutation," Blood, (1994), 9:2619-2626.
Tsujimura, et al., "Substitution of an Aspartic Acid Results in Constitutive Activation of c-kit Receptor Tyrosine Kinase in a Rat Tumor Mast Cell Line RBL-2H3," Int. Arch. Aller. Immunol., (1995), 106:377-385.
Tsujimura, T., "Role of c-kit Receptor Tyrosine Kinase in the Development, Survival and Neoplastic Transformation of Mast Cells," Pathol Int., (1996), 46:933-938.
Turner, et al., "Nonhematopoeietic Tumor Cell Lines Express Stem Cell Factor and Display c-kit Receptors," Blood, (1992), 80:374-381.
Udenfriend, et al., "Scintillation Proximity Assay: A Sensitive and Continuous Isotopic Method for monitoring Ligand/Receptor and Antigen/Antibody Interactions," Anal. Biochem, (1987), 161:494-500.
Uritskaya, et al., STN Accession Number: 1974-27133; Document Number: 08:27133; Abstract of Khimiya Geterotsiklicheskikh Soedinenii (1973), 10:1370-1373.
US Notice of Allowance of U.S. Appl. No. 11/016,350 dated Dec. 26, 2007 (039363-1903).
US Notice of Allowance of U.S. Appl. No. 11/154,988 dated Jun. 6, 2008 (039363-2121).
US Notice of Allowance of U.S. Appl. No. 11/154,988 dated Jul. 23, 2008 (039363-2121).
US Notice of Allowance of U.S. Appl. No. 11/154,988 dated Sep. 8, 2008 (039363-2121).
US Notice of Allowance of U.S. Appl. No. 11/435,381 dated May 27, 2010 (039363-2192).
US Notice of Allowance of U.S. Appl. No. 11/435,381 dated Jul. 27, 2010 (039363-2192).
US Notice of Allowance of U.S. Appl. No. 11/473,347 dated Jun. 18, 2010 (039363-2803).
US Notice of Allowance of U.S. Appl. No. 11/473,347 dated Sep. 8, 2010 (039363-2803).
US Notice of Allowance of U.S. Appl. No. 11/960,590 dated Aug. 11, 2010 (039363-3502).
US Notice of Allowance of U.S. Appl. No. 11/961,901 dated May 17, 2012 (039363-3402).
US Notice of Allowance of U.S. Appl. No. 11/962,044 dated Aug. 13, 2010 (039363-3302).
US Notice of Allowance of U.S. Appl. No. 11/986,667 dated Aug. 6, 2010 (039363-4152).
US Notice of Allowance of U.S. Appl. No. 12/244,730 dated Jan. 6, 2011 (039363-2128).
US Notice of Allowance of U.S. Appl. No. 12/616,079 dated Oct. 25, 2012 (039363-2805).
US Notice of Allowance of U.S. Appl. No. 13/216,200 dated Dec. 8, 2011 (039363-2807).
US Office Action in U.S. Appl. No. 11/016,350 dated Jun. 6, 2007 (039363-1903).
US Office Action in U.S. Appl. No. 11/016,350 dated Aug. 2, 2007 (039363-1903).
US Office Action in U.S. Appl. No. 11/016,350 dated Oct. 26, 2007 (039363-1903).
US Office Action in U.S. Appl. No. 11/154,988 dated Jan. 4, 2008 (039363-2121).
US Office Action in U.S. Appl. No. 11/154,988 dated Oct. 19, 2007 (039363-2121).
US Office Action in U.S. Appl. No. 11/435,381 dated Feb. 19, 2010 (039363-2192).
US Office Action in U.S. Appl. No. 11/435,381 dated Mar. 4, 2009 (039363-2192).
US Office Action in U.S. Appl. No. 11/435,381 dated Jun. 1, 2009 (039363-2192).
US Office Action in U.S. Appl. No. 11/473,347 dated Dec. 18, 2009 (039363-2803).
US Office Action in U.S. Appl. No. 11/487,134 dated May 15, 2008 (039363-1915).
US Office Action in U.S. Appl. No. 11/487,134 dated Aug. 22, 2007 (039363-1915).
US Office Action in U.S. Appl. No. 11/962,044 dated Feb. 17, 2010 (039363-3302).
US Office Action in U.S. Appl. No. 11/962,044 dated Sep. 23, 2009 (039363-3302).
US Office Action in U.S. Appl. No. 11/986,667 dated Feb. 26, 2010 (039363-4152).
US Office Action in U.S. Appl. No. 11/986,667 dated Sep. 22, 2009 (039363-4152).
US Office Action in U.S. Appl. No. 12/082,665 dated Nov. 8, 2010 (039363-1917).
US Office Action in U.S. Appl. No. 12/244,730 dated Jul. 22, 2010 (039363-2128).
US Office Action in U.S. Appl. No. 12/616,079 dated Feb. 9, 2012 (039363-2805).
US Office Action in U.S. Appl. No. 12/616,079 dated Jun. 29, 2012 (039363-2805).
US Office Action in U.S. Appl. No. 12/669,450 dated Dec. 27, 2012 (039363-7851).
US Office Action in U.S. Appl. No. 12/752,035 dated Oct. 3, 2012 (039363-6903).
US Office Action in U.S. Appl. No. 12/906,980 dated Feb. 29, 2012 (039363-2806).
US Office Action in U.S. Appl. No. 12/906,980 dated Oct. 17, 2012 (039363-2806).
US Office Action in U.S. Appl. No. 12/958,376 dated Apr. 18, 2012 (039363-2196).
US Office Action in U.S. Appl. No. 12/958,379 dated Jul. 17, 2012 (039363-4153).
US Office Action in U.S. Appl. No. 12/958,379 dated Nov. 14, 2012 (039363-4153).
US Office Action in U.S. Appl. No. 12/981,427 dated Mar. 5, 2013 (039363-3504).
US Office Action in U.S. Appl. No. 13/546,923 dated Sep. 18, 2012 (039363-4155).
US Office Action in U.S. Appl. No. 12/752,035 dated Jun. 18, 2013 (039363-6903).
US Office Action in U.S. Appl. No. 13/243,748 dated Jun. 27, 2013 (039363-2808).

(56) References Cited

OTHER PUBLICATIONS

Vachon, et al., "The influence of microencapsulation using Eudragit RS100 on the hydrolysis kinetics of acetylsalicylic acid," J. Microencapsulation, (1997), 14(3):281-301.
Valent, P., "Biology, Classification and Treatment of Human Mastocytosis," Wein/Klin Wochenschr., (1996), 108:385-397.
Van Heyningen, V., "One Gene—Four Syndromes," Nature, (1994), 367:319-320.
Van Regenmortel, M.H.V., "Use of biosensors to characterize recombinant proteins," Developments in Biological Standardization, (1994), 83:143-151.
Vandelli, et al., "Analysis of release data in the evaluation of the physical state of progesterone in matrix systems," J. Microencapsulation, (1993), 10(1):55-65.
Vely, et al., "BIAcore Analysis to Test Phosphopeptide-SH2 Domain Interactions," Methods in Molecular Biology, (2000), 121:313-321.
Verfaillie, C.M., "Chronic myelogenous leukemia: too much or too little growth, or both?" Leukemia, (1998), 12:136-138.
Viskochil, D., "It Takes Two to Tango: Mast Cell and Schwann Cell Interactions in Neurofibromas," J Clin Invest., (2003), 112:1791-1793.
Vliagoftis, et al., "The protooncogene c-kit and c-kit ligand in human disease," Journ. Clin. Immunol, (1997), 100:435-440.
Weber, P., "Physical Principles of Protein Crystallization," Adv. Protein Chem., (1991), 41:1-36.
Wells, et al., "Targeting the RET Pathway in Thyroid Cancer," Clin Cancer Res., (2009), 15(23):7119-7123.
Wendt, et al., "Identification of novel binding interactions in the development of potent, selective 2-naphthamide inhibitors of urokinase, synthesis, structural analysis, and SAR of y-Phenyl amide 6-substitution," J. Med. Chem., (2004), 47(2):303-324.
Werness, et al., "Association of Human Papillomavirus Types 16 and 18 E6 Proteins with p53," Science, (1990), 248:76-79.
Wessjohann, L., "Synthesis of Natural-Product-Based Compound Libraries," Curr Opin Chem Biol., (2000), 4:303-309.
Wharam, et al., "Specific Detection of DNA and RNA Targets Using a Novel Isothermal Nucleic Acid Amplification Assay Based on the Formation of a Three-Way Junction Structure," Nucleic Acids Res., (2001), 29:1-8.
Wild, et al., "Antibodies to Nerve Growth Factor Reverse Established Tactile Allodynia in Rodent Models of Neuropathic Pain without Tolerance," J. Pharmacol. Exp. Ther., (2007), 322:282-287.
Williams, et al., "Dissection of the Extracellular Human Interferon γ Receptor a-Chain into two Production in an *Escherichia coli* Thioredoxin Gene Fusion Expression system and Recognition by Neutralizing Antibodies," Biochemistry, (1995), 34:1787-1797.
Woon, et al., "Construction and Characterization of a 10-Fold Genome Equivalent Rat P1-Derived Artificial Chromosome Library," Genomics, (1998), 50:306-316.
Wright, et al., "The STE20 Kinase KGK Is Broadly Expressed in Human tumor Cells and Can Modulate Cellular Transformation, Invasion, and Adhesion," Mol. Cell. Biol., (2003), 23:2068-2082.
Wuthrich, K., "Chapter 10: Three-Dimensional Protein Structures by NMR," NMR of Proteins and Nucleic Acids, (1986), 10:176-199.
Wyckoff, et al., "Direct visualization of macrophage-assisted tumor cell intravasation in mammary tumors," Cancer Research, (2007), 67(6):2649-2656.
Xing, et al., "BRAF Mutation Predicts a Poorer Clinical Prognosis for Papillary Thyroid Cancer," J. Clin. Endocrinol. Metab., (2005), 90(12):6373-6379.
Xing, M., "BRAF mutation in thyroid cancer," Endocrine-Related Cancer, (2005), 12:245-262.
Xu, et al., "Modulation of Endothelial Cell function by Normal Polyspecific Human Intraveneous immunoglobulins," Am. J. Path., (1998), 153:1257-1266.
Yakhontov, et al., "Derivatives of 7-azaindole. XV. Electrophilic substitution of 4-methyl-7-azaindole and its derivatives," Zhurnal Obshchei Khimii, (1965), 1(11):2032-2040 (English abstract only).
Yamaguchi, et al., "Calcium Restriction Allows cAMP Activation of the B-Raf/ERK Pathway, Switching Cells to a cAMP-dependent Growth-stimulated Phenotype*," The Journal of Biological Chemistry, (2004), 279:40419-40430.
Yamaguchi, et al., "Cyclic AMP activates B-Raf and ERK in cyst epithelial cells from autosomal-dominant polycystic kidneys," Kidney International, (2003), 63:1983-1994.
Yang, et al., "Identification of Brain-Derived Neurotrophic Factor as a Novel Functional Protein in Hepatocellular Carcinoma," Cancer Res., (2005), 65:219-225.
Yang, et al., "Neurofibromin-Deficient Schwann Cells Secrete a Potent Migratory Stimulus for NF1+/-Mast Cells," J Clin Invest., (2003), 112:1851-1861.
Yang, et al., "Nf1-Dependent tumors require a microenvironment containing Nf1+/- -and c-kitDependent bone marrow," Cell, (2008), 135:437-448.
Yang, et al., "Synthesis of some 5-substituted indoles," Heterocycles, (1992), 34:1169-1175.
Yao, et al., "A Novel Human STE20-related Protein Kinase, HGK, That Specifically Activates the c-Jun N-terminal Kinase Signaling Pathway," J. Biol. Chem., (1999), 274:2118-2125.
Yee, et al., "Role of kit-Ligand in Proliferation and Suppression of Apoptosis in Mast Cells: Basis for Radiosensitivity of White Spotting and Steel Mutant Mice," J. Exp. Med., (1994), 179:1777-1787.
Yeung, et al., "Friedel-Crafts acylation of indoles in acidic imidazolium chloroaluminate ionic liquid at room temperature," Tetrahedron Letters, (2002), 43(33), 5793-5795.
Yoshida et al., "Studies on anti-helicobacter pylori agents, Part 1: Benzyloxyisoquinoline derivatives," Bioorganic & Medicinal Chemistry, Elsevier Science Ltd, 7(11):2647-2666 (1999).
Yuan, et al., Human Peripheral Blood Eosinophils Express a Functional c-kit Receptor for Stem Cell Factor that Stimulates Very Late Antigen 4 (VLA-4)-Mediated Cell Adhesion to Fibronectin and Vascular Cell Adhesion Molecule 1 (VCAM-1), J. Exp. Med., (1997), 186:313-323.
Zanon, et. al., "Copper-Catalyzed Domino Halide Exchange-Cyanation of Aryl Bromides," J. Am. Chem. Soc., (2003), 125:2890-2891.
Zhang, et al., "An effective procedure for the acylation of azaindoles at C-3," Journal of Organic Chemistry, (2002), 67(17):6226-6227.
Office Action dated Jan. 23, 2012 in related U.S. Appl. No. 11/961,901.
Serajuddin, A. T. M., "Solid Dispersion of Poorly Water-Soluble Drugs: Early Promises, Subsequent Problems, and Recent Breakthroughs," Journal of Pharmaceutical Sciences, American Pharmaceutical Association, Washington, US, 88:(10) 1058-1066 (1999).
Supplementary European Search Report for European Patent Application No. EP 12 78 9648 dated Jun. 23, 2014.

\* cited by examiner

SOLID FORMS OF A PHARMACEUTICALLY ACTIVE SUBSTANCE

CROSS-REFERENCE TO RELATED PATENT APPLICATIONS

This application is a U.S. National Stage Application under 35 U.S.C. 371 of International Application No. PCT/US2012/025965, filed Feb. 21, 2012, which claims the benefit of U.S. Provisional Patent Application No. 61/444,866, filed Feb. 21, 2011, the complete disclosures of which are hereby incorporated by reference.

The present invention relates to various forms and formulations of compounds, for example, compounds that have use in pharmaceutical applications.

The compound Propane-1-sulfonic acid {3[5-(4-chloro-phenyl)-1H-pyrrolo[2,3-b]pyridine-3-carbonyl]-2,4-difluoro-phenyl}-amide (compound 1) is represented by formula 1:

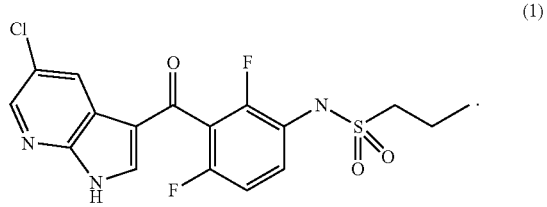 [SMILES: CCCS(=O)(=O)Nc1ccc(F)c(C(=O)c2c[nH]c3ncc(Cl)cc23)c1F]

(1)

The compound of formula 1 has been described in WO 2007002433 and WO 2007002325. The crystalline forms 1 and 2 (also I and II), the amorphous form, as well as the tosylate and mesylate salt of compound 1 are disclosed in International Application No. PCT/US 10/29489.

Active pharmaceutical ingredients (API's) may be prepared in a variety of different forms, such as for example salts, solvates, hydrates, co-crystals. API's may also be in their amorphous state or one or several crystalline forms (polymorphs). Depending on the form, the physicochemical properties of an API may change, leading to e.g. different solubility, thermodynamic stability, density or melting point of different forms. Such physicochemical properties therefore may have significant influence of the efficacy or bioavailability of a known API.

SUMMARY OF THE INVENTION

The present invention provides solid forms of the compound of formula 1 selected from the group consisting of:
a) a substantially amorphous form of compound 1, selected from form XVII, XVIII, XIX, XX, XXI, XXII, XXIII, XXIV, XXV, XXVI or combinations thereof, wherein compound 1 is molecularly dispersed;
b) a solvate of form III, IV, V, VI, VII, IX, X, XI, XII, XIII, XIV, or XV;
c) a polymorph of form VIII or XVI; and
d) the sulfuric acid-, hydrobromic acid- or hydrochloric acid salt of compound 1.

In one particular embodiment, said solid form is selected from a solvate of form III, IV, V, VI, VII, IX, X, XI, XII, XIII, XIV or XV.

In another particularly preferred embodiment, said solid form is selected from a polymorph of form VIII or XVI.

In yet another preferred embodiment, said solid form is selected from the sulfuric acid-, hydrobromic acid- or hydrochloric acid salt of compound 1.

In still another preferred embodiment, said solid form is a substantially amorphous form of compound 1, selected from form XVII, XVIII, XIX, XX, XXI, XXII, XXIII, XXIV, XXV or XXVI or combinations thereof, wherein compound 1 is molecularly dispersed.

In another embodiment, the invention provides a method for treating a disease or condition in a mammal in need thereof. The method includes administering to the mammal an effective amount of a composition comprising a solid form compound as described herein. In certain embodiments, the diseases or conditions are mediated by b-Raf mutants having V600E, V600M, V600R, V600K or V600G mutations. In other embodiments, the diseases or conditions include, but are not limited to melanoma, thyroid cancer and colorectal cancer.

The solid forms disclosed herein may be further processed into any type of solid pharmaceutical preparations or dosage forms, which are known to the person of skill in the art. Particularly preferred are oral dosage forms such as tablets, capsules, pills, powders, suspensions, pasts and the like. Detailed descriptions of suitable excipients as well as methods for making such pharmaceutical preparations can for example be found in: Raymond C. Rowe et al, *Handbook of Pharmaceutical Excipients, 6th edition,* 2009, Pharmaceutical Press (Publ.); ISBN-10: 0853697922.

Consequently, so obtained pharmaceutical preparations form further embodiments provided herein.

DETAILED DESCRIPTION OF THE INVENTION

Definitions

Figure 1:
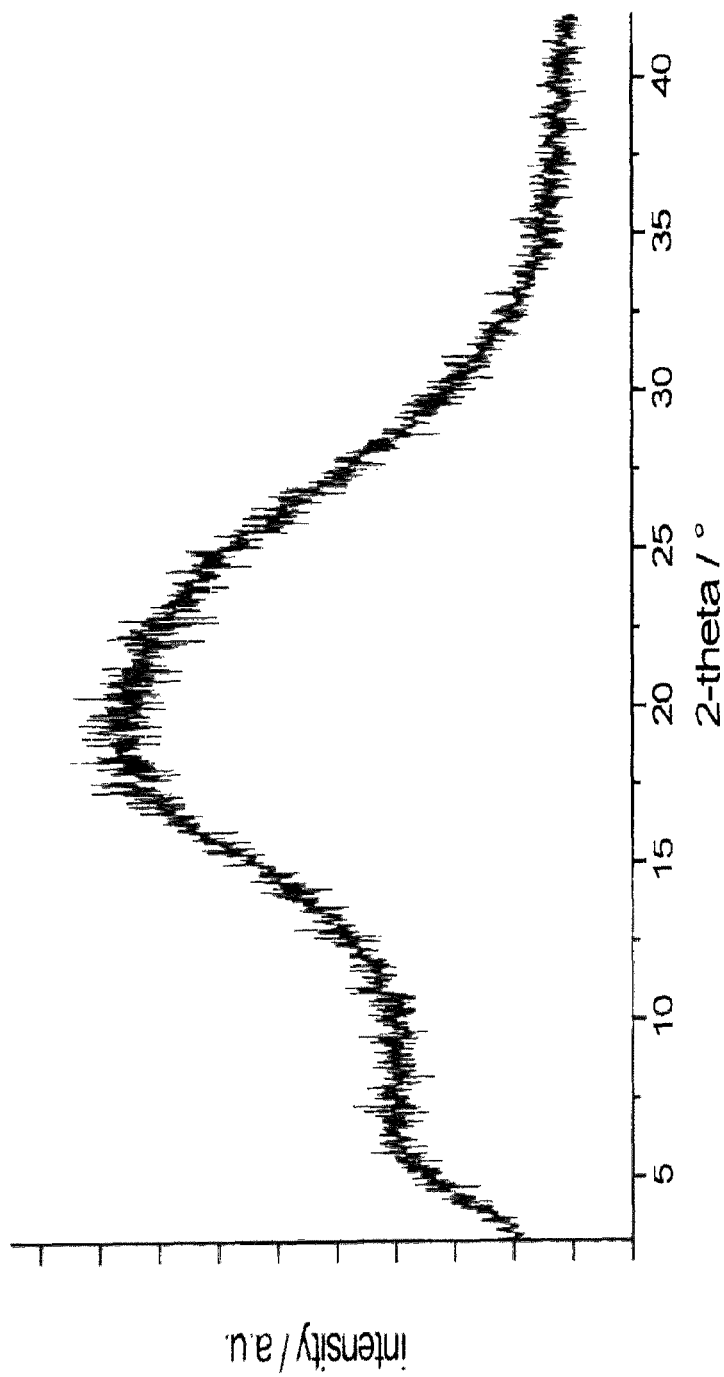
FIG. 1 shows XRPD patterns of the amorphous form of compound 1 as obtainable by the method disclosed in Example 1.

The term "compound 1" as used herein means Propane-1-sulfonic acid {3-[5-(4-chloro-phenyl)-1H-pyrrolo[2,3-b]pyridine-3-carbonyl]-2,4-difluoro-phenyl}-amide, which is sometimes also designated as PLX-4032.

As used herein, the general term "amorphous forms" denotes a material that lacks long range order and as such does not show sharp X-ray peaks. The X-Ray Powder Diffraction (XRPD) pattern of an amorphous material is characterized by one or more amorphous halos. More specifically, the term "amorphous form" as used herein refers to the amorphous form of Propane-1-sulfonic acid {3-[5-(4-chloro-phenyl)-1H-pyrrolo[2,3-b]pyridine-3-carbonyl]-2,4-difluoro-phenyl}-amide (compound 1) as such, provided said amorphous form does not form a one phase system, such as for example a solid dispersion or microprecipitated bulk powder (MBP) together with any type of supporting material such as polymers or the like.

The term "amorphous halo" means a broad diffraction maximum in the X-ray powder diffraction pattern of an amorphous substance, i.e. the amorphous form of compound 1. The FWHM (full width at half maximum) of an amorphous halo is usually bigger than two degrees in 2-theta.

The "Form II" of compound 1 as referred to herein means the thermodynamically stable form of Propane-1-sulfonic acid {3-[5-(4-chloro-phenyl)-1H-pyrrolo[2,3-b]pyridine-3-carbonyl]-2,4-difluoro-phenyl}-amide.

The term "molecularly dispersed", as used herein, refers to the random distribution of compound 1 within a polymer. More particularly, a compound (for example, compound 1) may be dispersed within a matrix formed by the polymer in its solid state such that the compound 1 and the matrix form a one phase system (solid dispersion) and compound 1 is immobilized in its amorphous form. An example of such solid dispersion is a micro-precipitated bulk powder (MBP). Whether a compound is molecularly dispersed in a polymer may be evidenced in a variety of ways, e.g., by the resulting solid molecular complex having a single glass transition temperature.

The term "flash cooling" as used herein means cooling with liquid nitrogen.

The term "approximately" in connection with the XRPD patterns as disclosed herein means that there is an uncertainty in the measurements of the degrees 2Theta of ±0.2 degrees (expressed in degrees 2Theta).

The term "polymorph" as used herein means one of the different crystal structures in which a compound can crystallize. Polymorphs are best characterized by their space group and unit-cell parameters. This term is reserved for materials with the same elemental analysis.

The term "solvate" as used herein means a crystal form that contains either stoichiometric or nonstoichiometric amounts of solvent.

The term "substantially amorphous" material embraces material which has no more than about 10% crystallinity; and "amorphous" material embraces material which has no more than about 2% crystallinity. In some embodiments, the "amorphous" material means material having no more than 1%, 0.5% or 0.1% crystallinity.

"Ambient temperature" means any temperature in the range of 18 to 28° C., preferably 20 to 24° C.

The term "composition" refers to a pharmaceutical preparation suitable for administration to an intended animal subject for therapeutic purposes that contains at least one pharmaceutically active compound, including any solid form thereof. The composition may include at least one additional pharmaceutically acceptable component to provide an improved formulation of the compound, such as a suitable carrier, additive or excipient.

The term "pharmaceutically acceptable" indicates that the indicated material does not have properties that would cause a reasonably prudent medical practitioner to avoid administration of the material to a patient, taking into consideration the disease or conditions to be treated and the respective route of administration. For example, it is commonly required that such a material be essentially sterile, e.g., for injectibles.

The term "therapeutically effective" or "effective amount" indicates that the materials or amount of material is effective to prevent, alleviate, or ameliorate one or more symptoms of a disease or medical condition, and/or to prolong the survival of the subject being treated. In certain embodiments, a "therapeutically-effective amount" of Compound I refers to such dosages and/or administration for such periods of time necessary to inhibit human b-Raf containing the V600E mutation. In some embodiments, the human b-Raf includes V600A, V600M, V600R, V600K or V600G mutations. Moreover, a therapeutically effective amount may be one in which the overall therapeutically-beneficial effects outweigh the toxic or undesirable side effects. A therapeutically-effective amount of Compound I may vary according to disease state, age and weight of the subject being treated. Thus, dosage regimens are typically adjusted to the individual requirements in each particular case and are within the skill in the art. In certain embodiments, an appropriate daily dose for administration of Compound 1 to an adult human may be from about 100 mg to about 3200 mg; or from about 250 mg to about 2000 mg, although the upper limit may be exceeded when indicated. A daily dosage of Compound 1 can be administered as a single dose, in divided doses, or, for parenteral administration, it may be given as subcutaneous injection.

In the spray dry dispersion process, Compound 1 and a polymer may be dissolved in a common solvent having a low boiling point, e.g., ethanol, methanol, acetone, etc. By means of spray drying or lyophilization, the solvent is evaporated by flash evaporation at the temperature close to boiling point or under a high vacuum (low vapor pressure), leaving the Compound 1 precipitated in a matrix formed by the polymer. In certain embodiments Compound 1 is in a mesylate or tosylate salt form, and thus preferably has improved solubility.

The term "methacrylic acid copolymers" as used herein in the spray dry dispersion process includes, but are not limited to, methacrylic acid copolymers, methacrylic acid—methacrylate copolymers, methacrylic acid—ethyl acrylate copolymers, ammonio methacrylate copolymers, aminoalkyl methacrylate copolymers and the like. In certain embodiments, a "methacrylic acid copolymer" may be EUDRAGIT® L 100 and EUDRAGIT® L 12,5 (also referred to as, or conforms with: "Methacrylic Acid Copolymer, Type A;" "Methacrylic Acid—Methyl Methacrylate Copolymer (1:1);" "Methacrylic Acid Copolymer L;" "DMF 1242" or "PR-MF 6918"); EUDRAGIT® S 100 and EUDRAGIT® S 12,5 (also referred to as, or conforms with: "Methacrylic Acid Copolymer, Type B;" "Methacrylic Acid—Methyl Methacrylate Copolymer (1:2);" "Methacrylic Acid Copolymer S;" "DMF 1242" or "PR-MF 6918"); EUDRAGIT® L 100-55 (also referred to as, or conforms with: "Methacrylic Acid Copolymer, Type C;" "Methacrylic Acid—Ethyl Acrylate Copolymer (1:1) Type A;" "Dried Methacrylic Acid Copolymer LD;" or "DMF 2584"); EUDRAGIT® L 30 D-55 (also referred to as, or conforms with: "Methacrylic Acid Copolymer Dispersion;" "Methacrylic Acid—Ethyl Acrylate Copolymer (1:1) Dispersion 30 Per Cent;" "Methacrylic Acid Copolymer LD;" JPE DMF 2584; PR-MF 8216); EUDRAGIT® FS 30 D (also referred to as DMF 13941 or DMF 2006-176); EUDRAGIT® RL 100 (also referred to as, or conforms with: "Ammonio Methacrylate Copolymer, Type A;" "Ammonio Methacrylate Copolymer (Type A);" "Aminoalkyl Methacrylate Copolymer RS;" "DMF 1242" or "PR-MF 6918"); EUDRAGIT® RL PO (also referred to as, or conforms with: "Ammonio Methacrylate Copolymer, Type A;" "Ammonio Methacrylate Copolymer (Type A);" "Aminoalkyl Methacrylate Copolymer RS;" "DMF 1242"); EUDRAGIT® RL 12,5 (also referred to as, or conforms with "Ammonio Methacrylate Copolymer, Type A;" "Ammonio Methacrylate Copolymer (Type A);" "DMF 1242" or "PR-MF 6918"); EUDRAGIT® L 100-55 (also referred to as, or conforms with: "Methacrylic Acid Copolymer, Type C;" "Methacrylic Acid—Ethyl Acrylate Copolymer (1:1) Type A;" "Dried Methacrylic Acid Copolymer LD;" "DMF 2584"); EUDRAGIT® L 30 D-55 (also referred to as, or conforms with: "Methacrylic Acid Copolymer Dispersion" NF "Methacrylic Acid—Ethyl Acrylate Copolymer (1:1) Dispersion 30 Per Cent;" "Methacrylic Acid Copolymer LD;" "DMF 2584" or "PR-MF 8216"); EUDRAGIT® FS 30 D (also referred to as, or conforms with: "DMF 13941" or "DMF 2006-176"); EUDRAGIT® RL 100 (also referred to as, or conforms with: "Ammonio Methacrylate Copolymer, Type A;" "Ammonio Methacrylate Copolymer (Type A);" "Aminoalkyl Methacrylate Copolymer RS;" "DMF 1242;" or "PR-MF 6918"); EUDRAGIT® RL PO (also referred to as, or conforms with: "Ammonio Methacrylate Copolymer, Type A;" "Ammonio Methacrylate Copolymer (Type A);" "Aminoalkyl Methacrylate Copolymer RS;" or "DMF 1242"); EUDRAGIT® RL 12,5 (also referred to as, or conforms with: polymer conforms to "Ammonio Methacrylate Copolymer, Type A;" "Ammonio Methacrylate Copolymer (Type A);" "DMF 1242" or "PR-MF 6918"); EUDRAGIT® RL 30 D (also referred to as, or conforms with: "Ammonio Methacrylate Copolymer Dispersion, Type A;" "Ammonio Methacrylate Copolymer (Type A);" or "DMF 1242"); EUDRAGIT® RS 100 (also referred to as, or conforms with: "Ammonio Methacrylate Copolymer, Type B;" NF "Ammonio Methacrylate Copolymer (Type B);" "Aminoalkyl Methacrylate Copolymer RS;" "DMF 1242" or "PR-MF 6918"); EUDRAGIT® RS PO (also referred to as, or conforms with: "Ammonio Methacrylate Copolymer, Type B;" "Ammonio Methacrylate Copolymer (Type B);" "Aminoalkyl Methacrylate Copolymer RS;" or "DMF 1242"); EUDRAGIT® RS 12,5 (also referred to as, or conforms with: "Ammonio Methacrylate Copolymer, Type B;" NF polymer conforms to "Ammonio Methacrylate Copolymer (Type B);" "DMF 1242" or "PR-MF 6918"); EUDRAGIT® RS 30 D (also referred to as, or conforms with: "Ammonio Methacrylate Copolymer Dispersion, Type B;" NF polymer conforms to "Ammonio Methacrylate Copolymer (Type B);" or "DMF 1242"); EUDRAGIT® E 100 (also referred to as, or conforms with: "Amino Methacrylate Copolymer;" NF "Basic Butylated Methacrylate Copolymer;" "Aminoalkyl Methacrylate Copolymer E;" "DMF 1242" or "PR-MF 6918"); EUDRAGIT® E PO (also referred to as, or conforms with: "Basic Butylated Methacrylate Copolymer;" "Aminoalkyl Methacrylate Copolymer E;" "Amino Methacrylate Copolymer;" "DMF 1242"); EUDRAGIT® E 12,5 (also referred to as, or conforms with: "Amino Methacrylate Copolymer;" "Basic Butylated Methacrylate Copolymer;" "DMF 1242" or "PR-MF 6918"); EUDRAGIT® E 30 D (also referred to as, or conforms with: "Ethyl Acrylate and Methyl Methacrylate Copolymer Dispersion;" "Polyacrylate Dispersion 30 Per Cent;" ("Poly(ethylacrylat-methylmethacrylat)-Dispersion 30%"); "Ethyl Acrylate Methyl Methacrylate Copolymer Dispersion;" "DMF 2822" or "PR-MF 6918"); EUDRAGIT® NE 40 D (also referred to as, or conforms with: DMF 2822); EUDRAGIT® NM 30 D (also referred to as "Polyacrylate Dispersion 30 Per Cent;" "(Poly(ethylacrylat-methylmethacrylat)-Dispersion 30%);" or "DMF 2822"; PLASTOID® B (also referred to as, or conforms with: "DMF 12102"), or the like.

The term "API" as used herein means active pharmaceutical ingredient.

The term "DSC" as used herein means Differential Scanning calorimetry.

The term "DVS" as used herein means Dynamic Vapor Sorption.

The term "IR" as used herein means Infra Red spectroscopy.

The term "Raman" as used herein means Raman spectroscopy.

The term "XRPD" as used herein means X-Ray Powder Diffraction.

The term "TGA" as used herein means ThermoGravimetric Analysis.

Characterization Methods

DSC curves were recorded using a Mettler-Toledo™ differential scanning calorimeter DSC820, DSC821 or DSC 1 with a FRS05 sensor. System suitability tests were performed with Indium as reference substance and calibrations were carried out using Indium, Benzoic acid, Biphenyl and Zinc as reference substances.

For the measurements, approximately 2-6 mg of sample were placed in aluminum pans, accurately weighed and hermetically closed with perforation lids. Prior to measurement, the lids were automatically pierced resulting in approx. 1.5 mm pin holes. The samples were then heated under a flow of nitrogen of about 100 mL/min using heating rates of usually 10 K/min.

TGA analysis was performed on a Mettler-Toledo™ thermogravimetric analyzer (TGA850 or TGA851). System suitability tests were performed with Hydranal as reference substance and calibrations using Aluminum and Indium as reference substances.

For the thermogravimetric analyses, approx. 5 10 mg of sample were placed in aluminum pans, accurately weighed and hermetically closed with perforation lids. Prior to measurement, the lids were automatically pierced resulting in approx. 1.5 mm pin holes. The samples were then heated under a flow of nitrogen of about 50 mL/min using a heating rate of 5 K/min.

DVS isotherms were collected on a DVS-1 (SMS Surface Measurements Systems) moisture balance system. The sorption/desorption isotherms were measured stepwise in a range of 0% RH to 90% RH at 25° C. A weight change of <0.002 mg/min was chosen as criterion to switch to the next level of relative humidity (with a maximum equilibration time of six hours, if the weight criterion was not met). The data were corrected for the initial moisture content of the samples; that is, the weight after drying the sample at 0% relative humidity was taken as the zero point.

IR spectra were recorded as film of a Nujol suspension of approximately 5 mg of sample and few Nujol between two sodium chloride plates, with an FTIR spectrometer in transmittance. The Spectrometer is a Nicolet™ 20SXB or equivalent (resolution 2 cm-1, 32 or more coadded scans, MCT detector).

Raman spectra were recorded in the range of 150-1800 $cm^{-1}$ at excitation of 785 nm with an ARAMIS (HoribaJobin-Yvon) Raman microscope equipped with a Peltier cooled CCD detector, and a 1200 l/mm grating.

X-ray powder diffraction patterns were recorded at ambient conditions in transmission geometry with a STOE STADIP diffractometer (Cu K$\alpha$ radiation, primary monochromator, position sensitive detector, angular range 3' to 42' 2Theta, approximately 60 minutes total measurement time). Approximately 25 mg of sample were prepared and analyzed without further processing (e.g. grinding or sieving) of the substance. Alternatively, X-ray diffraction patterns were measured on a Scintag X1 powder X-ray diffractometer equipped with a sealed copper K$\alpha$1 radiation source. The samples were scanned from 2° to 36° 2θ at a rate of 1° per minute with incident beam slit widths of 2 and 4 mm and diffracted beam slit widths of 0.3 and 0.2 mm.

The amorphous form of compound I according to the present invention is preferentially substantially pure, meaning the amorphous form includes less than about 15%, preferably less than about 10%, preferably less than about 5%, preferably less than about 1%, even more preferably less than 0.1% by weight of impurities, including other polymorph forms of compound 1. In some embodiments, at least about 30-99% by weight of the total of compound 1 in the composition is present as the amorphous form. In further embodiments, at least about 70%, at least about 80%, at least about 90%, at least about 99% or at least about 99.9% by weight of the total of compound 1 in the composition is present as the amorphous form. Also provided by the invention are compositions consisting essentially of compound 1 wherein at least about 97-99% by weight of the compound 1 is present in the composition as an amorphous form, a polymorph form, a solvate form as described herein or combinations thereof.

The polymorph, solvate or amorphous form of compound I according to the present invention can also be present in mixtures. In some embodiments, amorphous form XVII can be present in mixtures with one or more other amorphous forms selected from XVIII, XIX, XX, XXI, XXII, XXIII, XXIV, XXV or XXVI. Solvate form III can be present in mixtures with one or more solvate forms selected from IV, V, VI, VII, IX, X, XI, XII, XIII, XIV or XV. Polymorph form VIII can be present in a mixture with polymorph form XVI.

Suitable solvents for preparation of spray dry dispersion amorphous forms of compound 1 include, but are not limited to acetone, water, alcohols, mixtures thereof, and the like. The alcohols include, but are not limited to, ethanol, methanol, isopropanol and mixtures thereof.

The solid forms of compound 1 as disclosed herein can be used in a wide variety of preparations for administration of drugs, and in particular for oral dosage forms. Exemplary dosage forms include powders or granules that can be taken orally either dry or reconstituted by addition of water to form a paste, slurry, suspension or solution; tablets, capsules, or pills. Various additives can be mixed, ground or granulated with the solid dispersion as described herein to form a material suitable for the above dosage forms. Potentially beneficial additives may fall generally into the following classes: other matrix materials or diluents, surface active agents, drug complexing agents or solubilizers, fillers, disintegrants, binders and lubricants. With respect to the solvates and polymorphs as disclosed herein, pH modifiers (e.g., acids, bases, or buffers) may also be added. Examples of other matrix materials, fillers, or diluents include lactose, mannitol, xylitol, microcrystalline cellulose, calcium diphosphate, and starch. Examples of surface active agents include sodium lauryl sulfate and polysorbate 80. Examples of drug complexing agents or solubilizers include the polyethylene glycols, caffeine, xanthene, gentisic acid and cylodextrins. Examples of disintegrants include sodium starch gycolate, sodium alginate, carboxymethyl cellulose sodium, methyl cellulose, and croscarmellose sodium. Examples of binders include methyl cellulose, microcrystalline cellulose, starch, and gums such as guar gum, and tragacanth. Examples of lubricants include magnesium stearate and calcium stearate. Examples of pH modifiers include acids such as citric acid, acetic acid, ascorbic acid, lactic acid, aspartic acid, succinic acid, phosphoric acid, and the like; bases such as sodium acetate, potassium acetate, calcium oxide, magnesium oxide, trisodium phosphate, sodium hydroxide, calcium hydroxide, aluminum hydroxide, and the like, and buffers generally comprising mixtures of acids and the salts of said acids. At least one function of inclusion of such pH modifiers is to control the dissolution rate of the drug, matrix polymer, or both, thereby controlling the local drug concentration during dissolution.

In addition to the above additives or excipients, use of any conventional materials and procedures for formulation and preparation of oral dosage forms using the compositions disclosed herein known by those skilled in the art are potentially useful. For example, the skilled artisans may formulate the compositions in an appropriate manner, and in accordance with accepted practices, such as those described in Remington's Pharmaceutical Sciences (Gennaro, Ed., Mack Publishing Co., Pa. 1990).

Consequently, a further embodiment includes a pharmaceutical preparation containing the solid dispersion as obtained by a method as described herein.

In certain embodiments, the present invention provides a method for preparing a substantially amorphous form of compound (1), the amorphous form is selected from form XVII, XVIII, XIX, XX, XXI, XXII, XXIII, XXIV, XXV or XXVI or combinations thereof. The method includes preparing a spray dry dispersion solution of compound (1) and drying the dispersion solution of compound (1) under conditions sufficient to obtain the amorphous form XVII, XVIII, XIX, XX, XXI, XXII, XXIII, XXIV, XXV or XXVI or combinations thereof. In one embodiment, the spray dry dispersion solution is dried under vacuum. In one embodiment, a spray dry dispersion solution is prepared by dispersing a solution of compound (1) into a polymer solution under conditions sufficient to obtain the spray dry dispersion solution. Any solvents or a mixture of solvents that are suitable to dissolve compound (1) can be used. Exemplary solvents for dissolving compound (1) include, but are not limited to, tetrahydrofuran (THF), acetone, acetonitrile, benzene, ethanol, toluene, ether, ethyl acetate, dimethylformamide (DMF), dimethyl sulfoxide (DMSO) or a mixture of any two or more thereof. In certain instances, an acid, such as hydrochloric acid, sulfuric acid or nitric acid is added into an organic solvent system in a ratio sufficient to assist the dissolution of compound (1). The polymer solution can be prepared by dissolving a polymer in an organic solvent or a mixture of solvents with a suitable ratio. In certain instances, the polymer is dissolved in a solvent or a mixture of solvents at a temperature ranging from 20-100° C., 30-50° C. or 40-100° C. Any polymers as described herein can be used for the preparation of the polymer solution. Exemplary solvents for preparing the polymer solution include, but are not limited to THF, acetone, acetonitrile, benzene, ethanol, toluene, ether, ethyl acetate, DMF, DMSO, $H_2O$ or a mixture threof.

In certain embodiments, the invention provides a method for treating a disease or condition in a mammal in need thereof, said method comprising administering to said mammal an effective amount of a composition comprising at least one solid form of compound I selected from the group consisting of:

a) a substantially amorphous form of compound 1, selected from form XVII, XVIII, XIX, XX, XXI, XXII, XXIII, XXIV, XXV, XXVI or combinations thereof, wherein compound 1 is molecularly dispersed;

b) a solvate of form III, IV, V, VI, VII, IX, X, XI, XII, XIII, XIV, or XV;

c) a polymorph of form VIII or XVI; and d) the sulfuric acid-, hydrobromic acid- or hydrochloric acid salt of compound 1.

In certain embodiments, the disease or condition for which the above-described method is employed is melanoma, thyroid cancer or colon cancer.

In certain embodiments, the invention provides a method for treating a disease or condition in a mammal in need thereof, said method comprising administering to said mammal an effective amount of a composition comprising at least one solid form of compound I as described herein.

In certain embodiments, the disease or condition for which the above-described method is employed is melanoma, thyroid cancer or colon cancer.

EXAMPLES

Example 1

Reference Example

Preparation of Amorphous Form of propane-1-sulfonic acid {3-[5-(4-chlorophenyl)-1H-pyrrolo[2,3-b]pyridine-3-carbonyl-2,4-difluoro-phenyl]-amide} (Compound 1)

Amorphous material can be generally obtained by flash cooling of a melt and spray drying. Other processes such as for example lyophilization may also be used.

a) Preparation of Amorphous Material by Spray Drying 5.0 g of compound 1 were dissolved in 150 g of tetrahydrofuran (THF) at ambient temperature. The solution was filtered via a 5 μm filter. The clear solution was spray dried using a Buechi spray-dryer (model B290) using the following parameters:

| | |
|---|---|
| Air flow inlet [m3/h] | 40 |
| Air inlet temperature [° C.] | 100 |
| Solvent flow [%] | 20 |
| Spray drying flow [%] | 100 |
| Condensator [° C.] | −10 |

Yield: 2.8 g (56%) amorphous compound 1.

b) Preparation of Amorphous Material by Flash Cooling of a Melt 2 g of propane-1-sulfonic acid {3-[5-(4-chlorophenyl)-1H-pyrrolo[2,3-b]pyridine-3-carbonyl-2,4-difluoro-phenyl]-amide} were heated to 300° C. in a stainless steel pan on a heating plate. Additionally, the material was heated using a heat gun. After obtaining a complete melt the pan was submerged into liquid nitrogen. After 10 min. the pan was removed and put into a desiccator for 48 h. For better handling, the glassy material was crushed using a mortar.

c) Characterization of the Amorphous Form

The amorphous form can be characterized by the lack of sharp X-ray diffraction peaks in its XRPD pattern, as well as a glass transition temperature as obtainable via DSC measurement in the range of about 100° C. to 110° C. The exact glass transition temperature is largely dependent on the water/solvent content. FIG. 1 shows XRPD patterns of the amorphous form of compound 1 as obtainable by the method disclosed in this example.

Example 2

Reference Example

Preparation of Form I of propane-1-sulfonic acid {3-[5-(4-chlorophenyl)-1H-pyrrolo[2,3-b]pyridine-3-carbonyl-2,4-difluoro-phenyl]-amide}

Polymorphic form I can generally be obtained by drying of the hemi-acetone solvate (Form IX) at >70° C.

Example 3

Preparation of Form III of propane-1-sulfonic acid {3-[5-(4-chlorophenyl)-1H-pyrrolo[2,3-b]pyridine-3-carbonyl-2,4-difluoro-phenyl]-amide} a) Preparation of Form III by Equilibration in Acetonitrile 221.3 mg of amorphous material were digested in 500 µL of acetonitrile at ambient temperature for 2 days. The material was then isolated by filtration and dried at 22° C./5 mbar for 48 h.

b) Characterization of Form III

Figure 2:
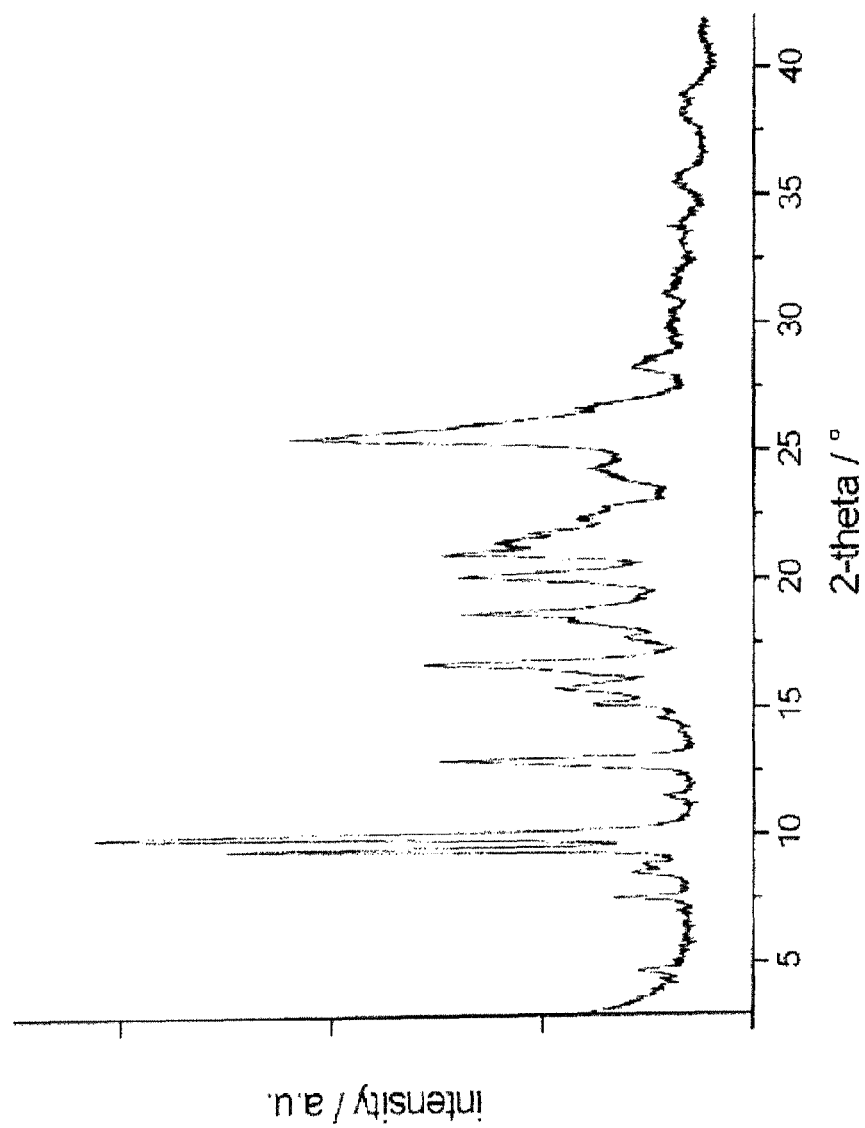
FIG. 2 shows the XRPD patterns of form III of compound 1 as obtained by the method disclosed in Example 3.

Form III can be characterized by XRPD patterns obtained with Cu Kα radiation having characteristic peaks expressed in degrees 2Theta at approximately 9.5, 10.0, 13.0, 16.7, 18.7, 20.1, 21.0, 25.6. The XRPD (X-Ray Powder Diffraction) pattern of a typical lot of form III of propane-1-sulfonic acid {3-[5-(4-chlorophenyl)-1H-pyrrolo[2,3-b]pyridine-3-carbonyl-2,4-difluoro-phenyl]-amide} is shown in FIG. 2.

Example 4

Preparation of Form IV of propane-1-sulfonic acid {3-[5-(4-chlorophenyl)-1H-pyrrolo[2,3-b]pyridine-3-carbonyl-2,4-difluoro-phenyl]-amide}

Form IV is a THF 0.75-solvate and can be generally obtained by processes comprising compound 1 and THF as solvent.

a) Preparation of Form IV by Evaporative Crystallization from THF 254.3 mg of compound 1 (form II) were dissolved in 6 mL of THF at 65° C. After 12 h the clear solution was cooled to 5° C. The crystals were isolated by filtration and dried at ambient conditions.

b) Characterization of Form IV

Figure 3:
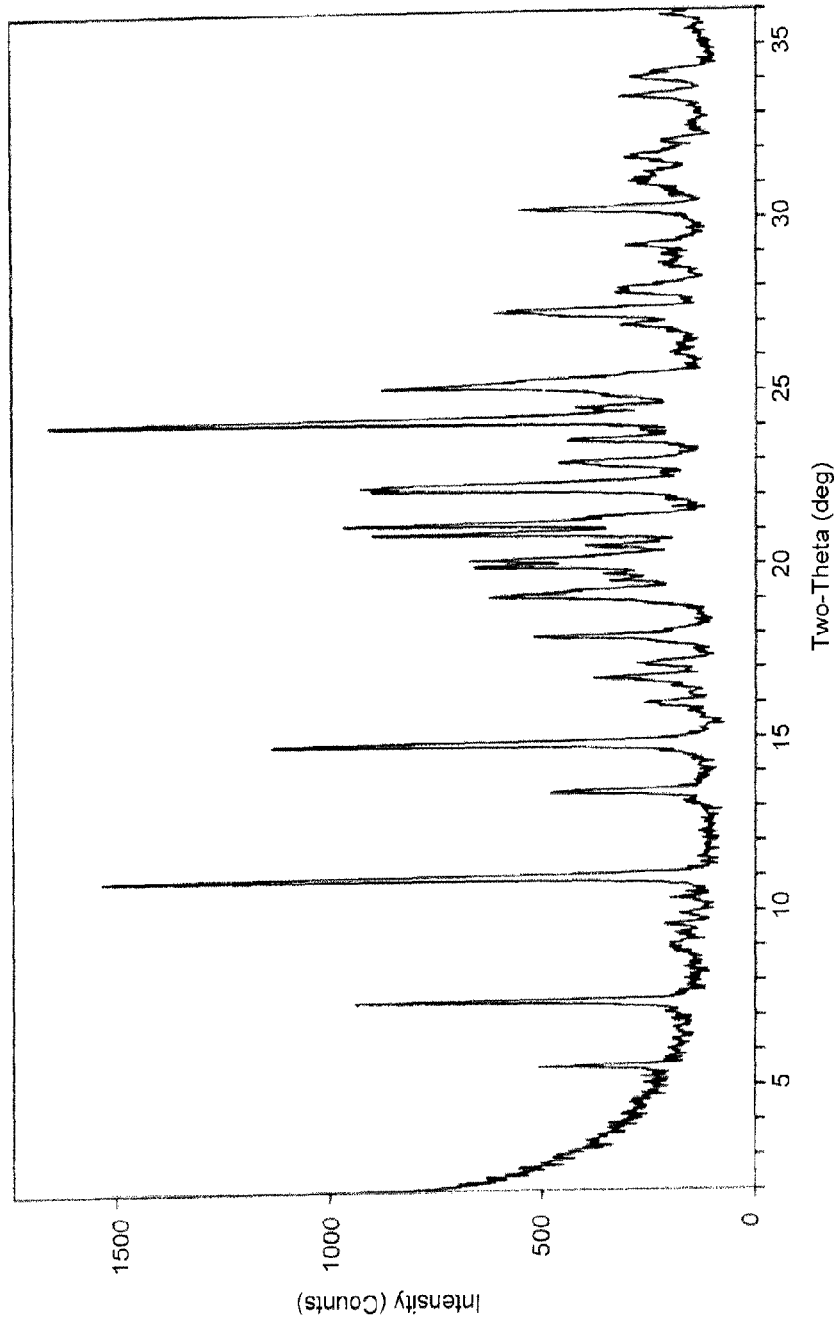
FIG. 3 shows the XRPD patterns of form IV of compound 1 as obtained by the method disclosed in Example 4.

Form IV can be characterized by its XRPD patterns obtained with Cu Kα radiation having characteristic peaks expressed in degrees 2Theta at approximately: 5.5, 7.4, 11.0, 13.4, 14.8, 16.0, 16.7, 17.1, 17.9, 19.1, 19.5, 20.1, 20.5, 20.9, 21.2, 22.2, 23.0, 23.6, 24.2, 24.5, 25.1. FIG. 3 shows the XRPD pattern of a typical lot of form IV of compound 1.

Example 5

Preparation of Form V of propane-1-sulfonic acid {3-[5-(4-chlorophenyl)-1H-pyrrolo[2,3-b]pyridine-3-carbonyl-2,4-difluoro-phenyl]-amide}

Form V is a dioxane mono-solvate and can be obtained by processes comprising compound 1 and dioxane as solvent.

a) Preparation of Form V by Equilibration in Dioxane 110.3 mg of amorphous material of compound 1 were suspended in 500 µL of dioxane. The wet material was digested at ambient temperature for 2 days. The material was then isolated by filtration and dried at 22° C./5 mbar for 48 h.

b) Characterization of Form V

Figure 4:
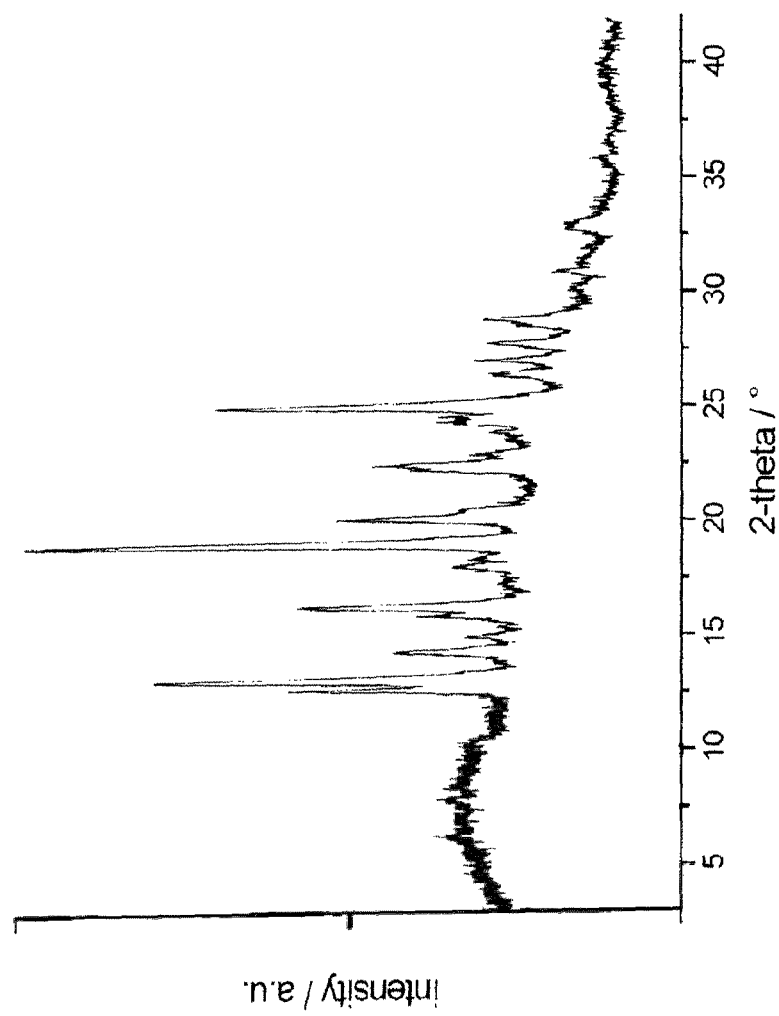
FIG. 4 shows the XRPD patterns of form V of compound 1 as obtained by the method disclosed in Example 5.

Form V can be characterized by its XRPD pattern obtained with Cu Kα radiation having characteristic peaks expressed in degrees 2Theta at approximately: 12.7, 13.1, 14.3, 16.3, 19.0, 20.1, 22.4, 25.1, 27.1, 28.9. FIG. 4 shows the XRPD pattern of a typical lot of form V of compound 1.

Example 6

Preparation of Form VI of propane-1-sulfonic acid {3-[5-(4-chlorophenyl)-1H-pyrrolo[2,3-b]pyridine-3-carbonyl-2,4-difluoro-phenyl]-amide}

Form VI is a DMF mono-solvate and can be obtained by procedures comprising compound 1 and DMF as solvent.

a) Preparation of Form VI by Equilibration in DMF 120.3 mg of amorphous material were slurried in 500 µL of DMF at ambient temperature for 2 days. The brownish material was isolated by filtration and dried at 30° C./5 mbar 48 h.

b) Characterization of Form VI

Figure 5:
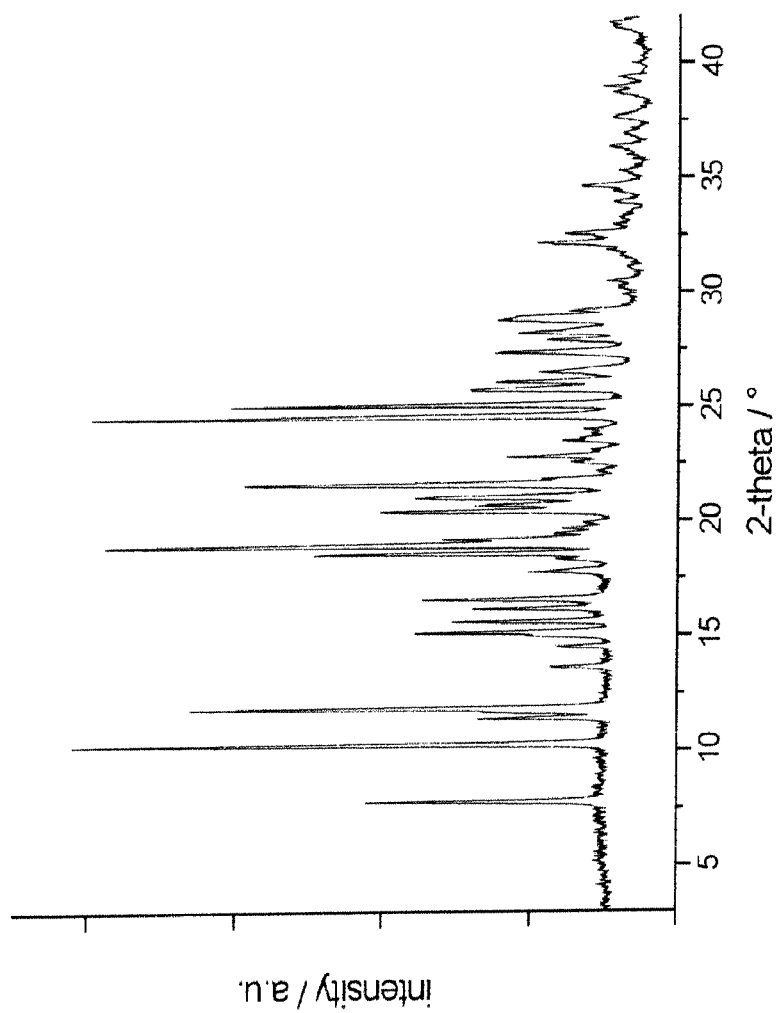
FIG. 5 shows the XRPD patterns of form VI of compound 1 as obtained by the method disclosed in Example 6.

Form VI can be characterized by its XRPD pattern obtained with Cu Kα radiation having characteristic peaks expressed in degrees 2Theta at approximately: 7.8, 10.3, 11.4, 11.8, 15.1, 15.6, 16.1, 16.6, 18.6, 18.9, 19.2, 20.4, 21.0, 21.6, 22.8, 24.6, 25.1, 25.8, 26.1, 27.4, 28.8. FIG. 5 shows the XRPD pattern of a typical lot of form VI of compound 1.

Example 7

Preparation of Form VII of propane-1-sulfonic acid {3-[5-(4-chlorophenyl)-1H-pyrrolo[2,3-b]pyridine-3-carbonyl-2,4-difluoro-phenyl]-amide}

Form VII is a THF hemi-solvate and can be obtained by processes comprising compound 1 and THF as solvent.

a) Preparation of Form VII by Equilibration in THF 196.3 mg of amorphous material were digested in 500 µL of THF for 3 days at ambient temperature. The brownish material was then isolated by filtration and dried at 22° C./5 mbar for 24 h.

b) Characterization of Form VII

Figure 6:
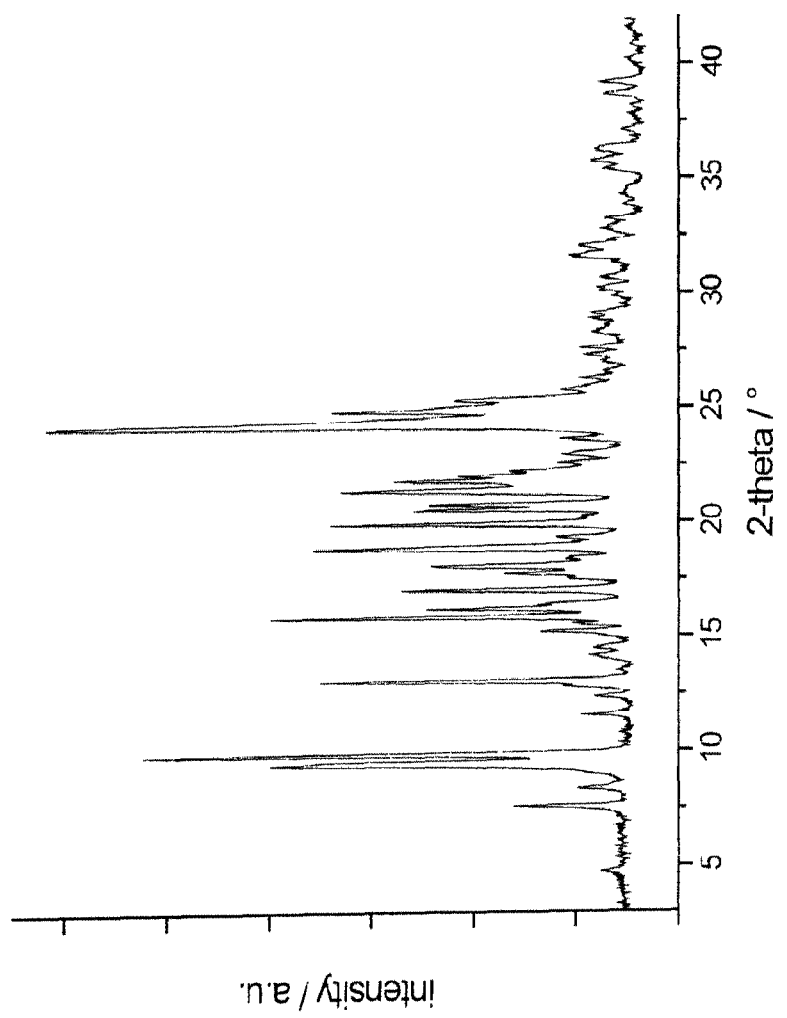
FIG. 6 shows the XRPD patterns of form VII of compound 1 as obtained by the method disclosed in Example 7.

Form VII can be characterized by its XRPD pattern obtained with Cu Kα radiation having characteristic peaks expressed in degrees 2Theta at approximately: 7.6, 9.4, 9.9, 13.1, 15.9, 16.2, 17.0, 18.1, 18.8, 19.9, 20.5, 20.7, 21.4, 21.8, 24.3, 24.9, 25.3. FIG. 6 shows the XRPD pattern of a typical lot of form VII of compound 1.

Example 8

Preparation of Form VIII of propane-1-sulfonic acid {3-[5-(4-chlorophenyl)-1H-pyrrolo[2,3-b]pyridine-3-carbonyl-2,4-difluoro-phenyl]-amide} a) Preparation of Form VIII by Incubation of Amorphous Material 210 mg of amorphous material of compound 1 were tempered at 130° C. for 24 h using a ball tube furnace. Then the brownish material was cooled to ambient temperature.

b) Characterization of Form VIII

Figure 7:
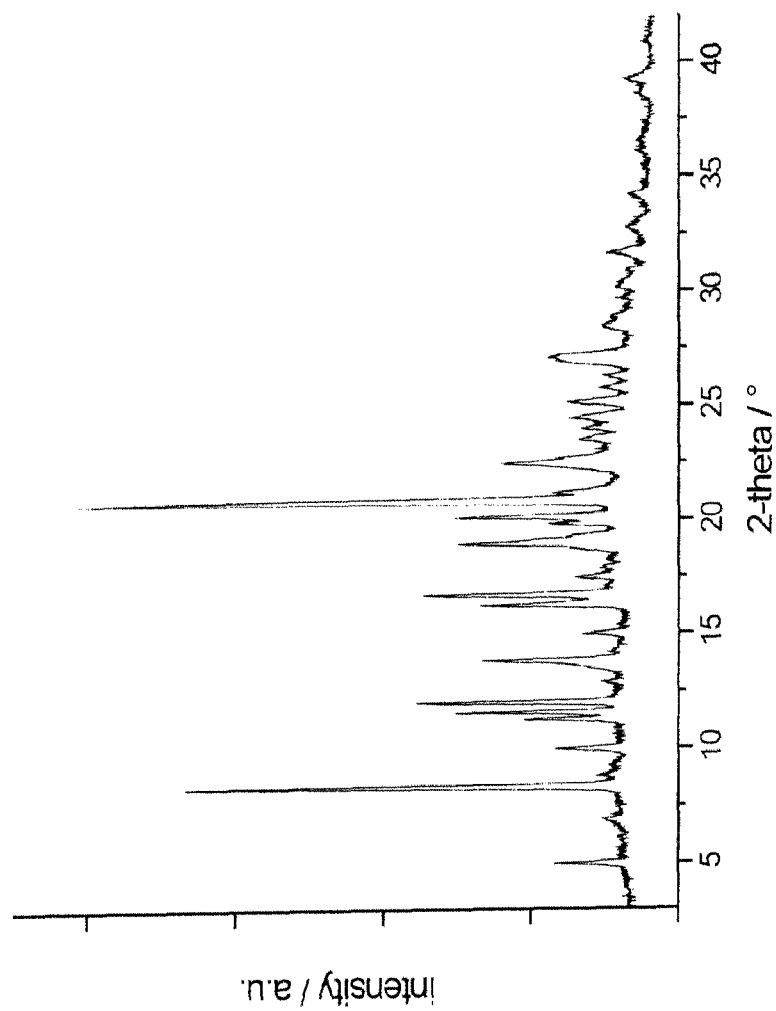
FIG. 7 shows the XRPD patterns of form VIII of compound 1 as obtained by the method disclosed in Example 8.

Form VIII can be characterized by its XRPD pattern obtained with Cu Kα radiation having characteristic peaks expressed in degrees 2Theta at approximately: 5.0, 11.3, 11.6, 12.0, 13.8, 16.2, 16.7, 19.0, 20.1, 20.8, 22.5, 27.1. FIG. 7 shows the XRPD pattern of a typical lot of form VIII of compound 1.

Example 9

Preparation of Form IX of propane-1-sulfonic acid {3-[5-(4-chlorophenyl)-1H-pyrrolo[2,3-b]pyridine-3-carbonyl-2,4-difluoro-phenyl]-amide}

Form IX is an acetone hemi-solvate and can be obtained by processes comprising compound 1 and acetone as solvent.

a) Preparation of Form IX by Equilibration in Acetone 180.5 mg of amorphous material of compound 1 were digested in 500 µL of acetone for 3 days at ambient temperature. Then the brownish material was isolated by filtration and dried at ambient temperature for 24 h.

b) Characterization of Form IX

Figure 8:
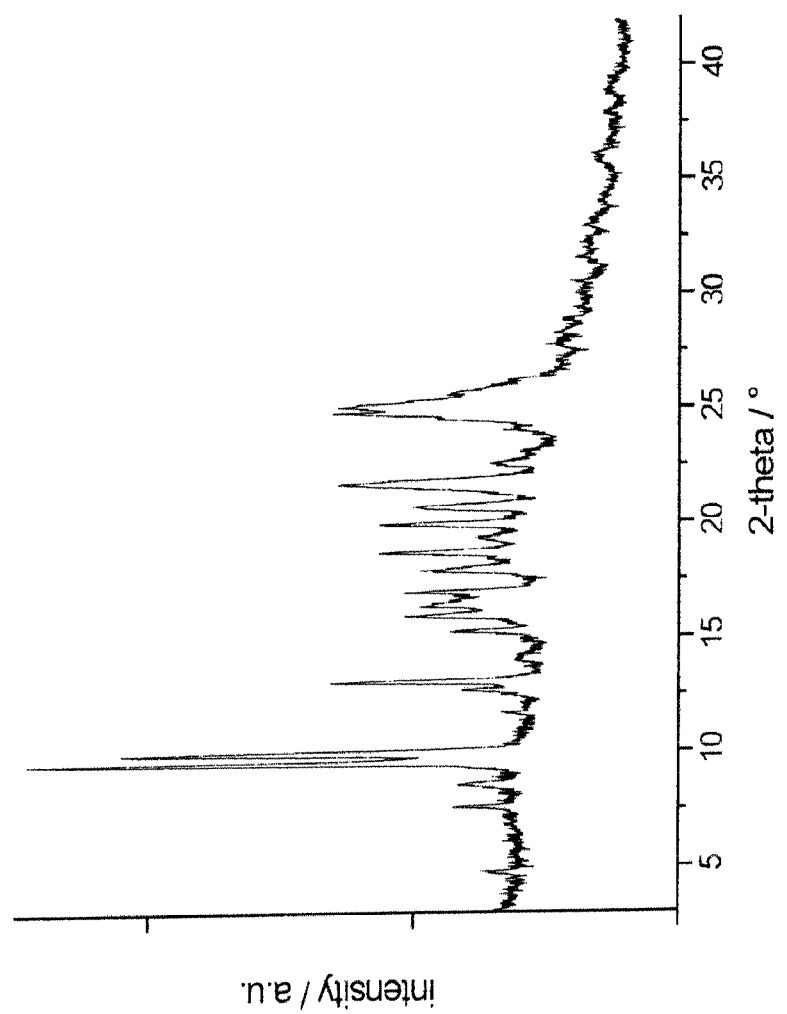
FIG. 8 shows the XRPD patterns of form IX of compound 1 as obtained by the method disclosed in Example 9.

Form IX can be characterized by its XRPD pattern obtained with Cu Kα radiation having characteristic peaks expressed in degrees 2Theta at approximately: 9.5, 9.9, 13.0, 15.9, 16.4, 17.0, 17.9, 18.7, 19.9, 20.7, 21.7, 24.8, 25.1. FIG. 8 shows the XRPD pattern of a typical lot of form IX of compound 1.

Example 10

Preparation of Form X of propane-1-sulfonic acid {3-[5-(4-chlorophenyl)-1H-pyrrolo[2,3-b]pyridine-3-carbonyl-2,4-difluoro-phenyl]-amide}

Form X is a pyridine mono-solvate and can be generally obtained by processes comprising compound 1 and pyridine as solvent.

a) Preparation of Form X by Equilibration in Pyridine 150.0 mg of compound 1 (Form II) were digested in 200 µL of pyridine at ambient temperature for 10 days. Then the brownish material was isolated by filtration and dried at 22° C. at 5 mbar for 48 h.

b) Characterization of Form X

Figure 9:
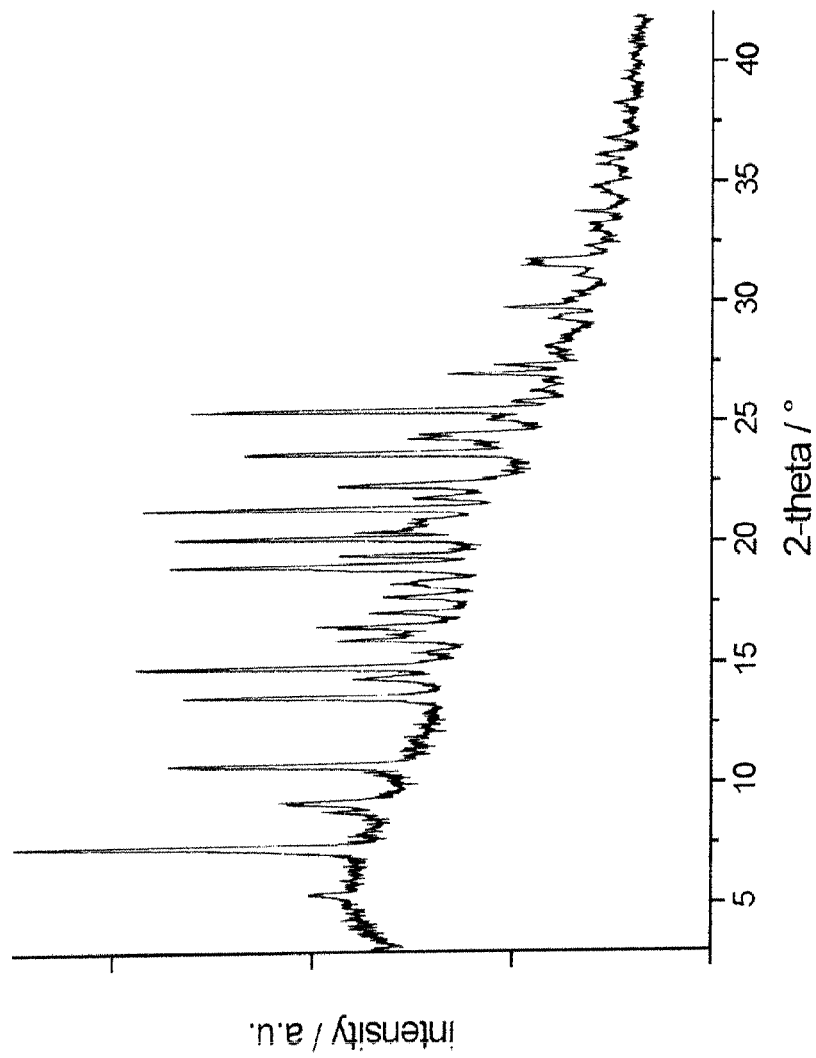
FIG. 9 shows the XRPD patterns of form X of compound 1 as obtained by the method disclosed in Example 10.

Form X can be characterized by its XRPD pattern obtained with Cu Kα radiation having characteristic peaks expressed in degrees 2Theta at approximately: 7.4, 9.2, 10.8, 13.6, 14.9, 19.0, 20.2, 21.4, 22.4, 23.7, 25.5, 27.0, 29. FIG. 9 shows the XRPD pattern of a typical lot of form X of compound 1.

Example 11

Preparation of Form XI of propane-1-sulfonic acid {3-[5-(4-chlorophenyl)-1H-pyrrolo[2,3-b]pyridine-3-carbonyl-2,4-difluoro-phenyl]-amide}

Form XI is a 2-methylpyridine mono-solvate and can be generally obtained by processes comprising compound 1 and 2-methylpyridine as solvent.

a) Preparation of Form XI by Evaporative Crystallization from 2-methylpyridine 150.0 mg of compound 1 (e.g. in its amorphous form or form II) were dissolved in 4 mL of 2-methylpyridine. The solution was allowed to evaporate passively at ambient temperature. After 10 d the material was further dried at 22° C./5 mbar for 48 h.

b) Characterization of Form XI

Figure 10:
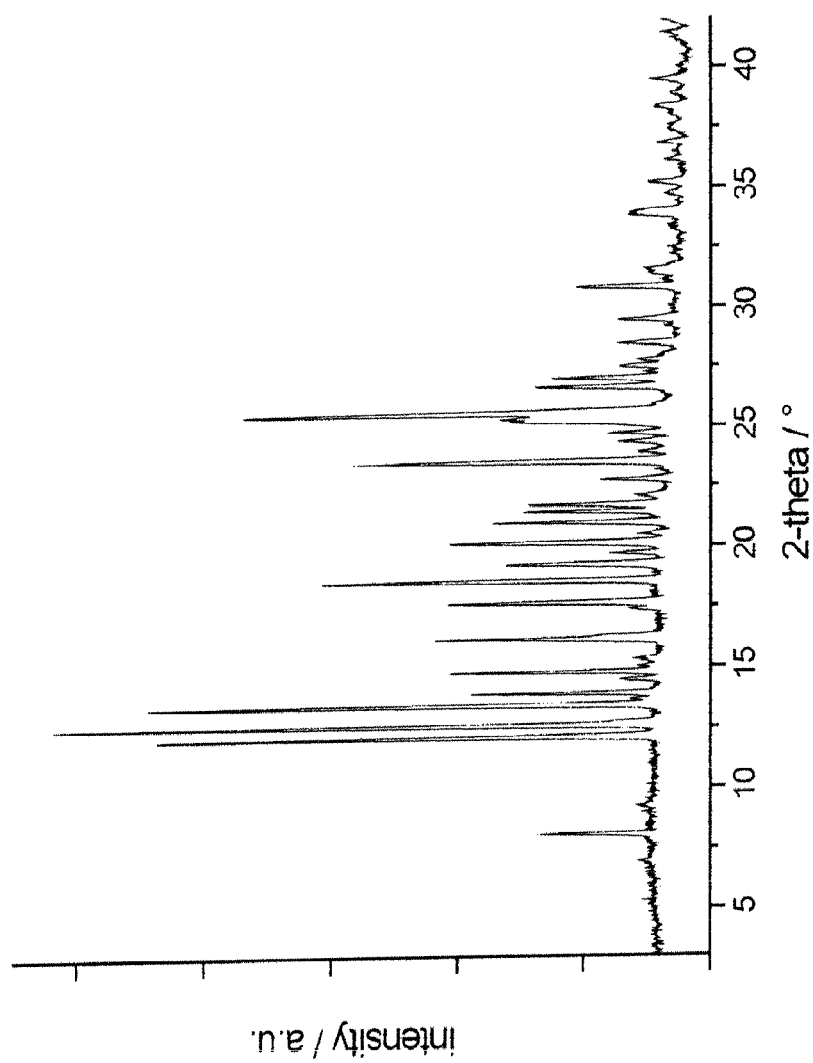
FIG. 10 shows the XRPD patterns of form XI of compound 1 as obtained by the method disclosed in Example 11.

Form XI can be characterized by its XRPD pattern obtained with Cu Kα radiation having characteristic peaks expressed in degrees 2Theta at approximately 8.0, 12.1, 12.6, 13.4, 13.9, 14.8, 16.2, 17.6, 18.5, 19.2, 20.1, 21.0, 21.4, 21.7, 23.5, 25.3, 25.5, 26.6, 27.0, 30.8. FIG. 10 shows the XRPD pattern of a typical lot of form XI of compound 1.

Example 12

Preparation of Form XII of propane-1-sulfonic acid {3-[5-(4-chlorophenyl)-1H-pyrrolo[2,3-b]pyridine-3-carbonyl-2,4-difluoro-phenyl]-amide}

Form XII is a diisopropylamine mono-solvate and can generally be obtained by processes comprising compound 1 and diisopropylamine as solvent.

a) Preparation of Form XII by Evaporative Crystallization from 2-methylpyridine 243.0 mg of compound 1 (form II) were slurried in 500 µL of diisopropylamine at 60° C. for 9 days. Then, the brownish material was isolated by filtration and dried at 22° C./5 mbar for 48 h.

b) Characterization of Form XII

Figure 11:
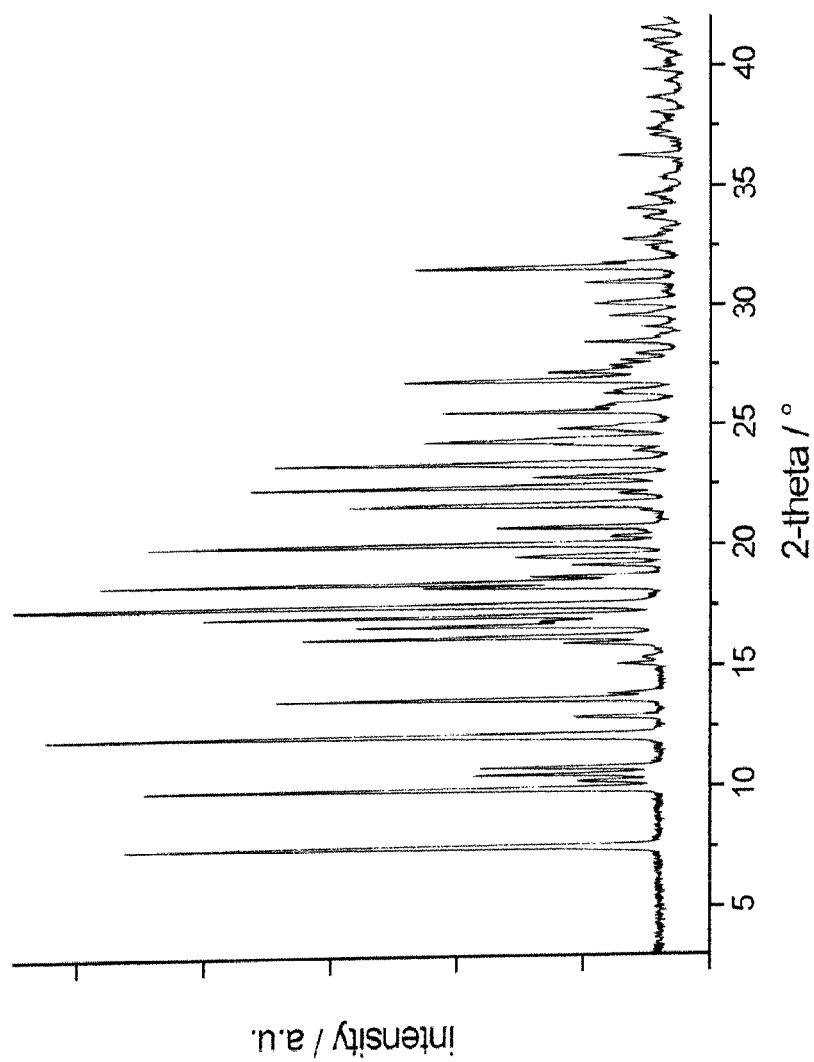
FIG. 11 shows the XRPD patterns of form XII of compound 1 as obtained by the method disclosed in Example 12.

Form XII can be characterized by an X-ray powder diffraction pattern obtained with Cu K α radiation having characteristic peaks expressed in degrees 2Theta at approximately: 7.5, 9.9, 12.1, 13.6, 16.2, 16.7, 17.1, 17.5, 18.3, 18.5, 20.1, 21.7, 22.4, 23.4, 24.3, 25.6, 26.9, 31.6. FIG. 11 shows the XRPD pattern of a typical lot of form XII of compound 1.

Example 13

Preparation of Form XIII of propane-1-sulfonic acid {3-[5-(4-chlorophenyl)-1H-pyrrolo[2,3-b]pyridine-3-carbonyl-2,4-difluoro-phenyl]-amide}

Form XIII is a morpholine mono-solvate and can generally be obtained by processes comprising compound 1 and morpholine as solvent.

a) Preparation of from XIII by Incubation with Morpholine Vapor 250.3 mg of amorphous material were incubated with morpholine vapor for 44 d at ambient temperature.

b) Characterization of Form XIII

Figure 12:
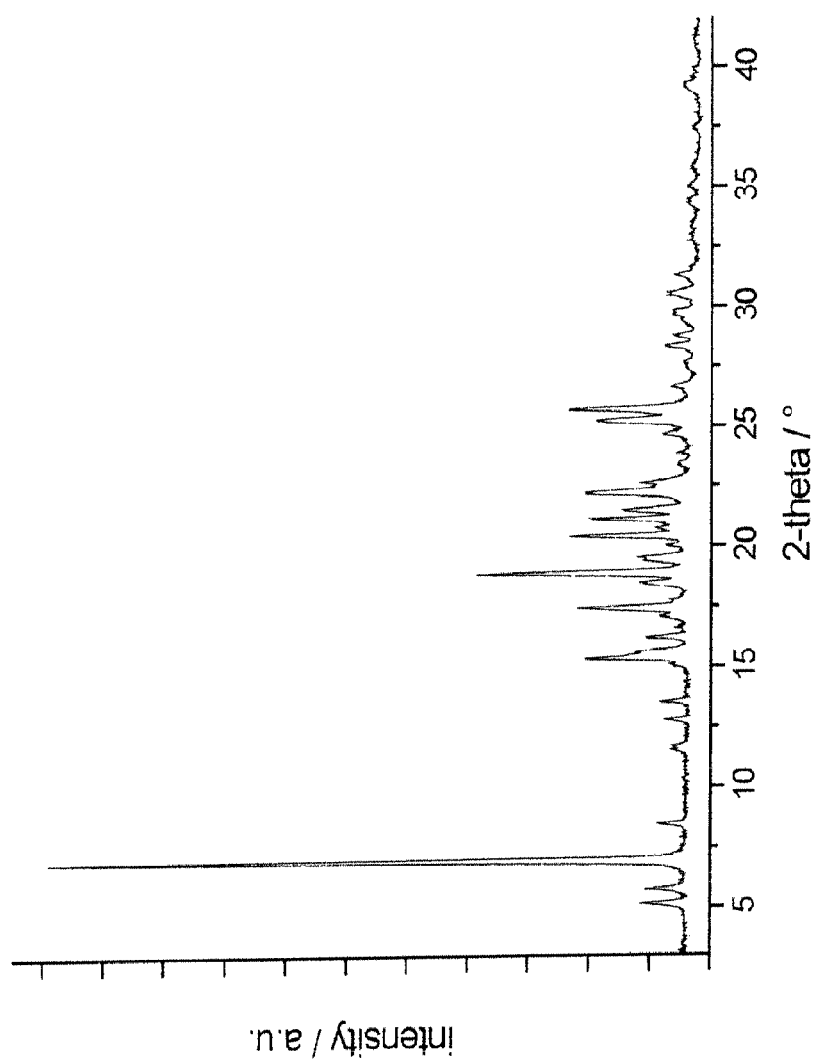
FIG. 12 shows the XRPD patterns of form XIII of compound 1 as obtained by the method disclosed in Example 13.

From XIII can be characterized by an X-ray powder diffraction pattern obtained with Cu Kα radiation having characteristic peaks expressed in degrees 2Theta at approximately 5.1, 5.8, 6.9, 15.3, 16.2, 17.4, 18.4, 18.9, 19.5, 20.4, 21.1, 21.5, 22.2, 22.6, 25.2, 25.7. FIG. 12 shows the XRPD pattern of a typical lot of form XIII of compound 1.

Example 14

Preparation of Form XIV of propane-1-sulfonic acid {3-[5-(4-chlorophenyl)-1H-pyrrolo[2,3-b]pyridine-3-carbonyl-2,4-difluoro-phenyl]-amide}

Form XIV is a DMSO mono-solvate and can be generally obtained by processes comprising compound 1 and DMSO as solvent.

a) Preparation of Form XIV by Evaporative Crystallization from DMSO 1.2 g compound 1 (form II) were dissolved in 5 mL of DMSO at ambient temperature. The clear solution was concentrated in a vacuum tray dryer at 40° C./20 mbar for 2 days. The crystals were isolated by filtration and dried at ambient conditions for 4 days.

b) Characterization of Form XIV

Figure 13:
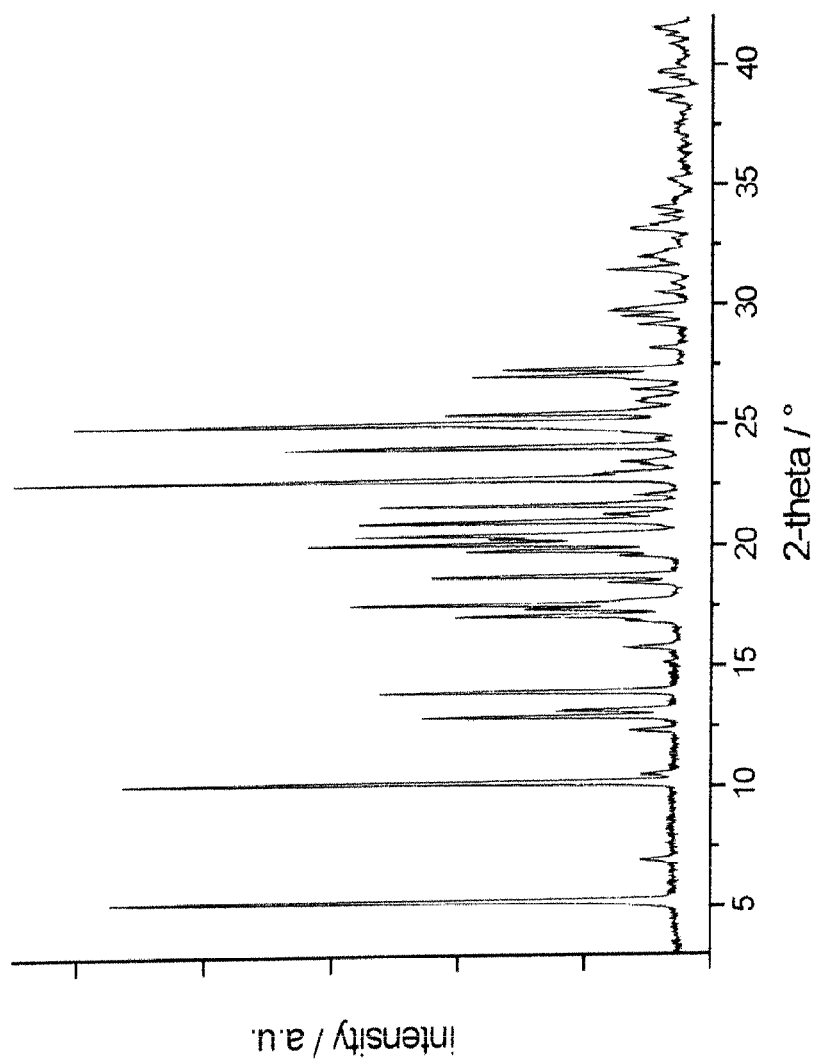
FIG. 13 shows the XRPD patterns of form XIV of compound 1 as obtained by the method disclosed in Example 14.

Form XIV can be characterized by an X-ray powder diffraction pattern obtained with Cu Kα radiation having characteristic peaks expressed in degrees 2Theta at approximately 5.2, 10.2, 12.9, 13.9, 17.1, 17.6, 18.7, 19.8, 20.1, 20.5, 21.0, 21.7, 22.8, 24.1, 25.1, 25.5, 27.1, 27.4. FIG. 13 shows the XRPD pattern of a typical lot of form XIV of compound 1.

Example 15

Preparation of Form XV of propane-1-sulfonic acid {3-[5-(4-chlorophenyl)-1H-pyrrolo[2,3-b]pyridine-3-carbonyl-2,4-difluoro-phenyl]-amide}

Figure 14:
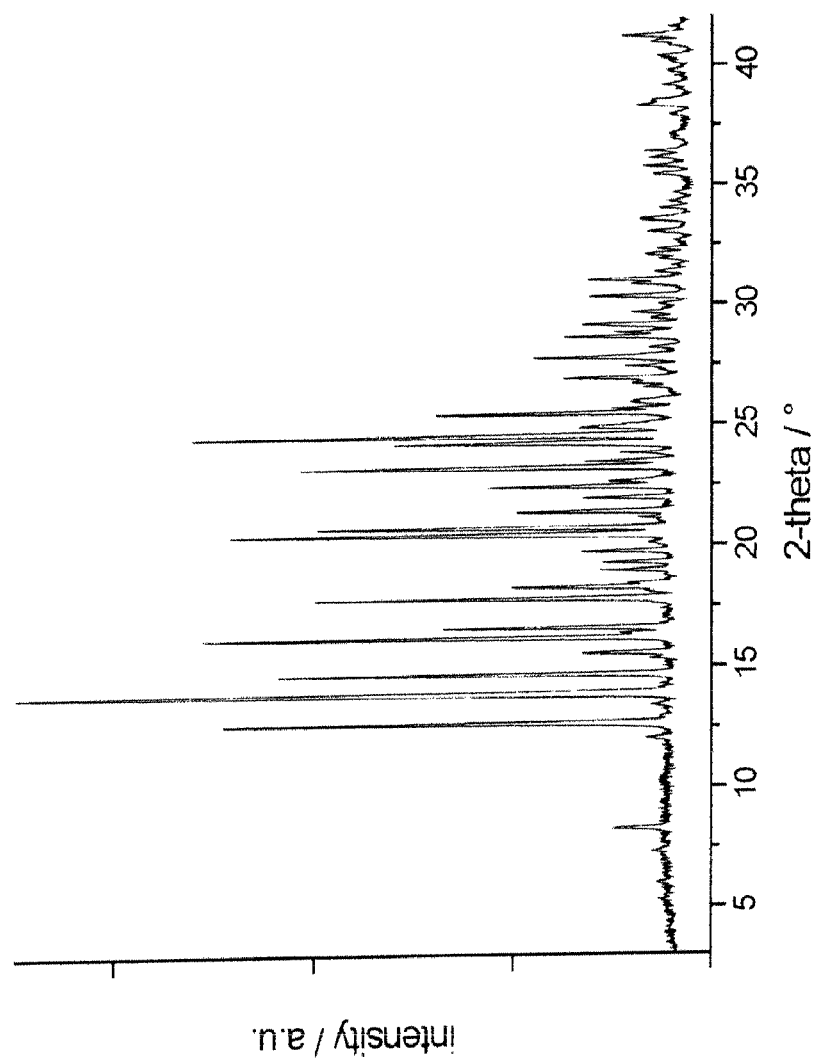
FIG. 14 shows the XRPD patterns of form XV of compound 1 as obtained by the method disclosed in Example 15.

Form XV is a DMSO mono-solvate and can generally be obtained by processes comprising compound 1 in DMSO as solvent.
a) Preparation of Form XV by Incubation with DMSO Vapor
Drops of a solution of 100 mg compound 1 in 500 µL of DMSO were placed on a glass slide. After evaporation of the solvent small crystals were observed. In 3 out of 9 drops form XV was observed. The other crystallization trials yielded form XIV.
b) Characterization of Form XV
Form XV can be characterized by an X-ray powder diffraction pattern obtained with Cu Kα radiation having characteristic peaks expressed in degrees 2Theta at approximately 12.6, 13.8, 14.6, 16.2, 16.6, 17.8, 18.3, 20.4, 20.7, 21.4, 22.4, 23.2, 24.2, 24.5, 25.5, 26.9, 27.8, 28.7. FIG. 14 shows the XRPD pattern of form XV of compound 1.

Example 16

Preparation of Form XVI of propane-1-sulfonic acid {3-[5-(4-chlorophenyl)-1H-pyrrolo[2,3-b]pyridine-3-carbonyl-2,4-difluoro-phenyl]-amide}

Figure 15:
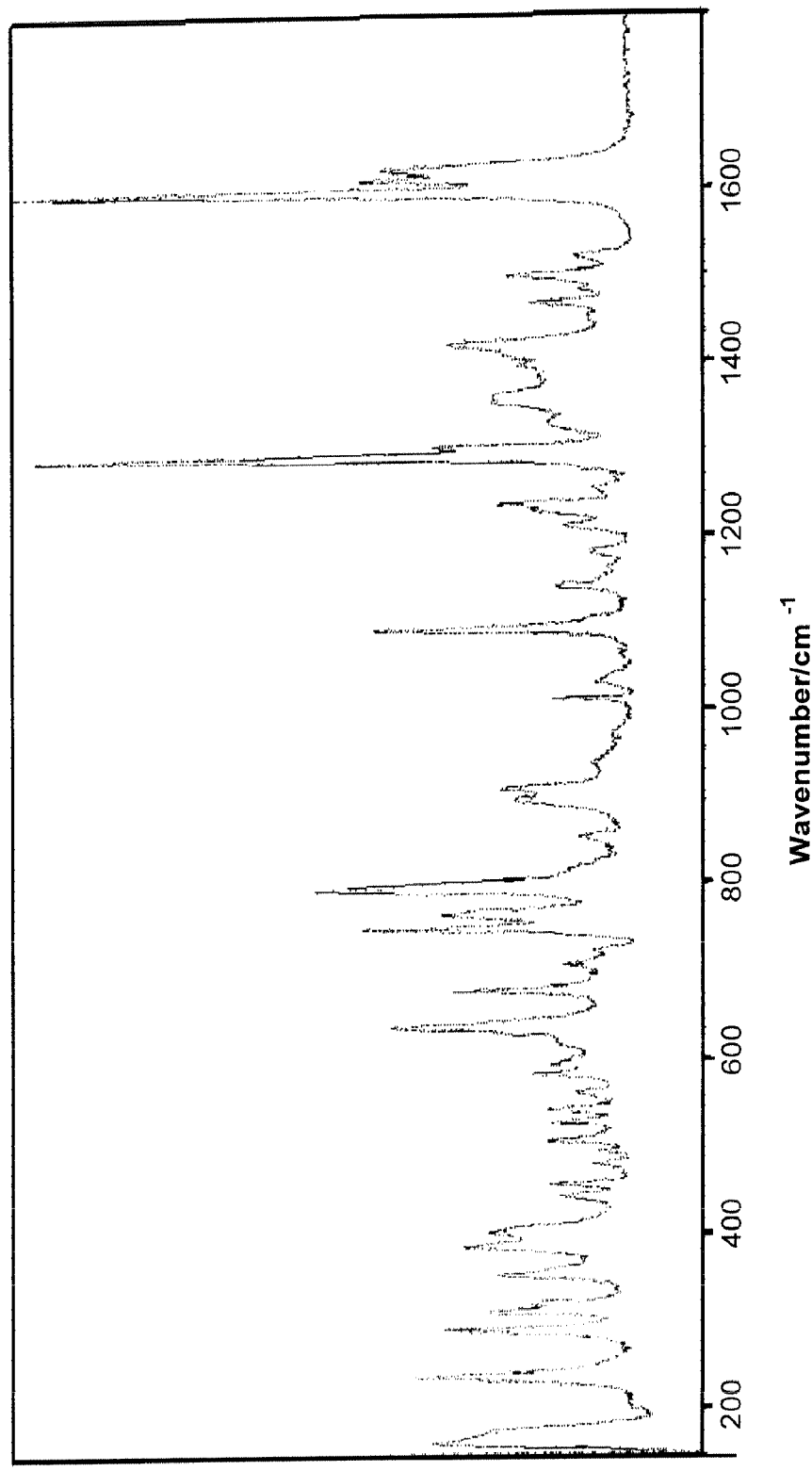
FIG. 15 shows the Raman spectrum of form XVI of compound 1 as obtained by the method disclosed in Example 16.

Polymorphic form XVI can be obtained by heating amorphous melt films on glass slides. Form XVI could not be crystallized pure, but with form VIII.
a) Preparation of Form XVI
Small amounts of compound 1 (form II) were heated between a microscopic glass slide and cover glass to about 280° C. The melt was then cooled to low temperatures by transferring the slide directly onto a cold metal block (e.g. cooled to −18 or −196° C.). The transfer should be as quick as possible. The obtained amorphous melt film is then placed on a heating stage on a microscope and observed under cross-polarized light. Upon heating with heating rates between 1 and 10° C./min crystallization can be observed in the range from 140-150° C. During this process, form VIII and form XVI crystallize side by side.
b) Characterization of Form XVI
Form XVI can be characterized by a Raman spectrum as shown in FIG. 15.

Example 17

Preparation of "Pattern 6"

Figure 16:
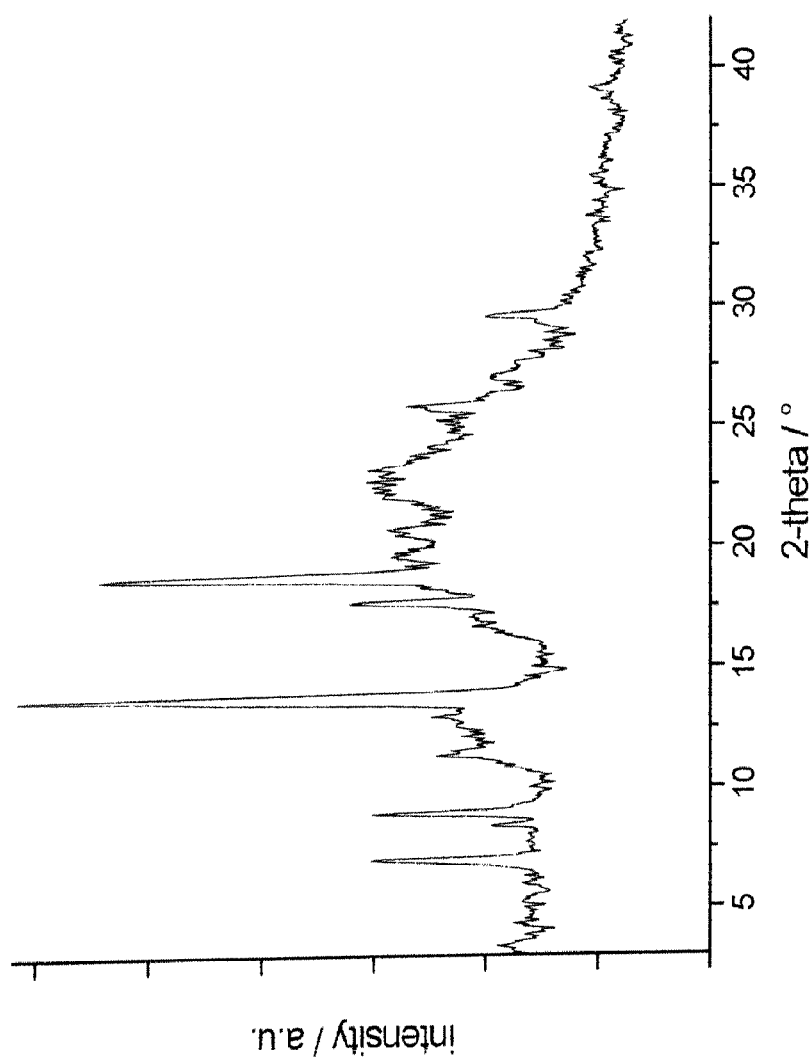
FIG. 16 shows the XRPD patterns of pattern 6 of compound 1 as obtained by the method disclosed in Example 17.

Small amount of the amorphous material was prepared in 1 mm diameter glass capillary and heated to 150° C. in a hot stage attached to a STOE Stadi P diffractometer. Subsequently the sample was analyzed at 150° C.
b) Characterization of Pattern 6
Pattern 6 can be characterized by an X-ray powder diffraction pattern obtained with Cu Kα radiation having characteristic peaks expressed in degrees 2Theta at approximately 7.0, 8.4, 8.9, 13.0, 13.8, 17.7, 18.8, 20.7, 25.8, 29.7. FIG. 16 shows the XRPD pattern of Pattern 6 of compound 1.

Example 18

Figure 17:
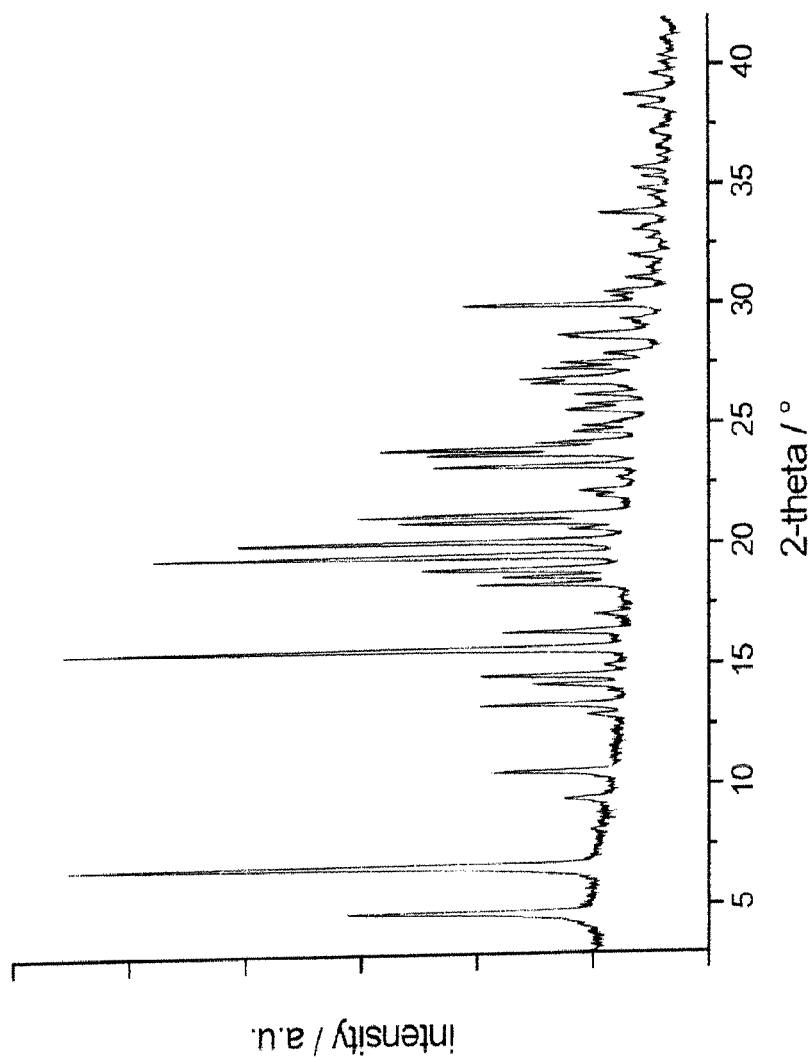
FIG. 17 shows the XRPD patterns of sulfuric acid salt of compound 1 as obtained by the method disclosed in Example 18.

Preparation of propane-1-sulfonic acid {3-[5-(4-chlorophenyl)-1H-pyrrolo[2,3-b]pyridine-3-carbonyl-2,4-difluoro-phenyl]-amide} sulfuric acid salt The sulfuric acid salt can be obtained by processes, comprising compound 1 and sulfuric acid.

a) Preparation of the Sulfuric Acid Salt in Tetrahydrofuran 6.15 g of compound 1 are slurried in 168.7 g of tetrahydrofuran. The suspension is heated to 55° C. A clear solution is obtained. At 30° C. a solution of 1.4 g sulfuric acid in 5 g 2-propanol is added. At 40° C. and 20 mbar 80 mL of the solvent are removed by distillation. Subsequently 22.3 g tert.-butylmethylether are added. The solution is stirred for 12 hours at 20° C. and starts to crystallize. The solid is isolated by filtration and rinsed by 17.8 g of tetrahydrofurane.
The product is dried at 40° C./2 mbar for 12 h. Yield: 4.2 g (57.5%).
b) Characterization of the Sulfuric Acid Salt
The sulfuric acid salt can be characterized by an X-ray powder diffraction pattern obtained with Cu Kα radiation having characteristic peaks expressed in degrees 2Theta at approximately 4.7, 6.7, 10.6, 13.3, 14.5, 15.7, 16.4, 18.3, 18.6, 18.9, 19.5, 20.1, 20.9, 21.2, 23.2, 23.7, 24.0, 26.9, 30.0. FIG. 17 shows the XRPD pattern of a typical lot of sulfuric acid salt of compound 1. The sulfuric acid salt of compound 1 can be further characterized by a melting point with onset temperature (DSC) of about 221° C. to 228° C.

Example 19

Preparation of propane-1-sulfonic acid {3-[5-(4-chlorophenyl)-1H-pyrrolo[2,3-b]pyridine-3-carbonyl-2,4-difluoro-phenyl]-amide}hydrobromic acid salt (bromide salt)

Figure 18:
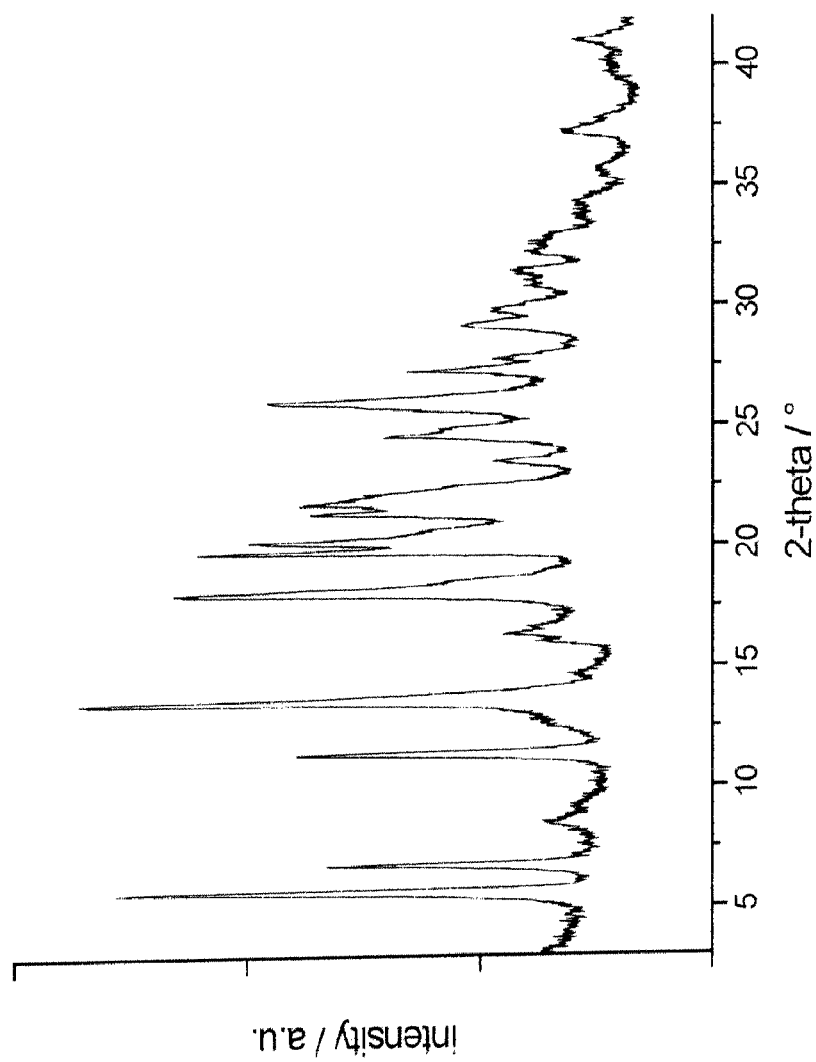
FIG. 18 shows the XRPD patterns of hydrobromic acid salt of compound 1 as obtained by the method disclosed in Example 19.

The hydrobromic acid salt can be obtained by processes comprising compound 1 and hydrogen bromide.
a) Preparation of the Hydrobromic Acid Salt in Tetrahydrofuran
6.15 g of compound 1 are slurried in 168.7 g of tetrahydrofuran. The suspension is heated to 55° C. A clear solution is obtained. At 30° C. a solution of 3.4 g hydrobromic acid solution (33% HBr in acetic acid) is added and a white solid is precipitating. The suspension is stirred for 2 hours at 20° C. The solid is isolated by filtration and rinsed by 17.8 g of tetrahydrofuran.
The product is dried at 40° C./2 mbar for 12 h. Yield: 4.6 g (61.7%).
b) Characterization of the Bromide Salt
The bromide salt can be characterized by an X-ray powder diffraction pattern obtained with Cu Kα radiation having characteristic peaks expressed in degrees 2Theta at approximately 5.7, 6.8, 11.4, 13.6, 18.1, 19.8, 20.2, 21.4, 21.8, 24.6, 26.1, 27.3, 29.2. FIG. 18 shows a XRPD pattern of a typical lot of bromide salt of compound 1. This salt can be further characterized by a melting point with onset temperature (DSC) in the range of about 240° C. to 246° C. Melting occurs under decomposition and can vary substantially.

Example 20

Preparation of propane-1-sulfonic acid {3-[5-(4-chlorophenyl)-1H-pyrrolo[2,3-b]pyridine-3-carbonyl-2,4-difluoro-phenyl]-amide}hydrochloric acid salt The hydrochloric acid salt can be obtained by processes comprising compound 1 and hydrogen chloride.

a) Preparation of the Hydrochloric Acid Salt in Tetrahydrofuran 10.0 g of compound 1 are slurried in 176 g of tetrahydrofuran. The suspension is stirred at 20° C. 4.8 g of a hydrochloric acid solution (4 M in dioxane) is added within 30 minutes. A white solid is precipitated. The suspension is stirred for additional 3 hour at 40° C. and subsequently cooled down to 20° C. The solid is isolated by filtration and rinsed by 17.8 g of tetrahydrofuran.

The product is dried at 40° C./2 mbar for 12 h. Yield: 8.9 g (83.7%)

b) Characterization of the Chloride Salt

Figure 19:
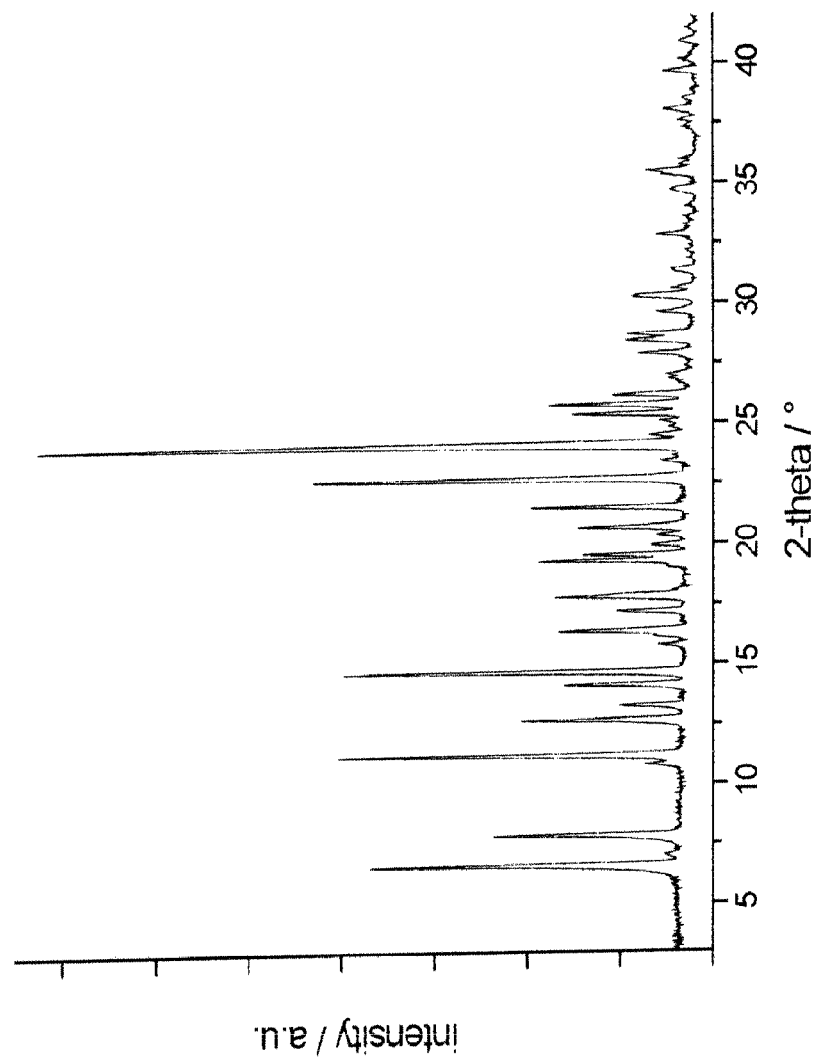
FIG. 19 shows the XRPD patterns of hydrochloric acid salt of compound 1 as obtained by the method disclosed in Example 20.

The chloride salt can be characterized by an X-ray powder diffraction pattern obtained with Cu Kα radiation having characteristic peaks expressed in degrees 2Theta at approximately 6.6, 7.8, 11.2, 12.6, 14.1, 14.7, 16.3, 17.8, 19.3, 19.6, 20.7, 21.5, 22.7, 24.1, 25.4, 25.8. FIG. 19 shows the XRPD pattern of a typical lot of hydrochloric acid salt of compound 1.

Example 21

Spray Dry Dispersion Solution Preparation

Compound (1) was dispersed in acetone or a mix of THF/acetone, an excess of 1 mol equivalent of 2M hydrochloric acid was dispensed into the vessel and stirred until dissolved. Isopropanol was dispensed into the vessel and allowed to stir. Excess hydrochloric acid was sufficient in maintaining solution stability for spray drying.

Polymer solutions of hydroxypropyl methyl cellulose acetate succinate (HPMCAS), copolymers of methacrylic acid and ethylacrylate (L100-55) or copolymer of vinylpyrrolidone-vinyl acetate (PVPVA) were prepared respectively by dissolving polymers into ethanol, adding an appropriate amount of acetone to the dissolved polymer solution, dispensing compound (1) into the polymer solution, and heating the solution to approximately 45° C. until all components were fully dissolved. The solutions were cooled back to room temperature prior to spray drying.

Example 22

Spray Dry Dispersion Solution Preparation and Manufacturing

Each formula was spray dried using a target inlet temperature of 100-105° C., an outlet temperature of 55° C., and an atomizing gas pressure of 0.5 bar. The feed material was atomized using a 0.5 mm two-fluid Schlick nozzle for all runs. Collection of the product is at the cyclone. A variable speed peristaltic pump, Master Flex, equipped with #14 Tygon Chemical tubing, was used to deliver the feed material.

Spray dried dispersions were vacuum oven dried overnight for 65 hours at 37° C. under a reduced pressure between −25 to −30 in Hg (Stage 1). These samples were further vacuum oven dried for an additional 65 hours at 45° C. under a reduced pressure between −25 to −30 in Hg (Stage 2). Spray dried dispersions were vacuum oven dried for 65 hours at 45° C. under a reduced pressure between −25 to −30 in Hg. Residual solvent are below 5000 PPM.

Spray dry dispersion solutions for amorphous forms XVII, XVIII, XIX, XX, XXI, XXII, XXIII, XXIV, XXV or XXVI were prepared according to the procedure set forth in Example 21. Spray dry dispersion formulas of amorphous forms XVII, XVIII, XIX, XX, XXI, XXII, XXIII, XXIV, XXV or XXVI were prepared according to the procedure set forth in Example 22.

Table 1 illustrates the spray dry dispersion of formulations of amorphous forms XVII, XVIII, XIX, XX, XXI, XXII, XXIII, XXIV, XXV and XXVI.

TABLE 1

| Compound No. | Polymer | Formulation | Solvent |
|---|---|---|---|
| XVII | HPMCAS | Compound (1)-30% HPMCAS - 70% | THF:Acetone - 20%:80% |
| XVIII | | Compound (1)-30% HPMCAS - 70% | THF:Acetone - 20%:80% |
| XIX | | Compound (1)-30% HPMCAS - 70% | THF:Acetone - 20%:80% |
| XX | | Compound (1)-30% HPMCAS - 70% HCl salt | Acetone 100% |
| XXI | | Compound (1)-50% HPMCAS - 50% HCl salt | Acetone 100% |
| XXII | | Compound (1)-33% HPMCAS - 67% HCl Salt | Acetone:IPA:water - 95%:3.8%:1.2% |
| XXIII | | Compound (1)-40% HPMCAS - 60% HCl Salt | Acetone:IPA:water - 95%:3.8%:1.2% |
| XXIV | L100-55 | Compound (1)-50% L100-55 - 50% HCl salt | THF:Acetone - 20%:80% |
| XXV | PVPVA | Compound (1)-33.3% PVPVA - 33.3% PVPK30 - 33.3% | Acetone:Ethanol - 20%:80% |
| XXVI | PVPVA | Compound (1)-33% PVPVA - 67% | Acetone:Ethanol - 20%:80% |

Example 23

Characterization of the Compounds a) Characterization of Solid Form XVII

Figure 20:
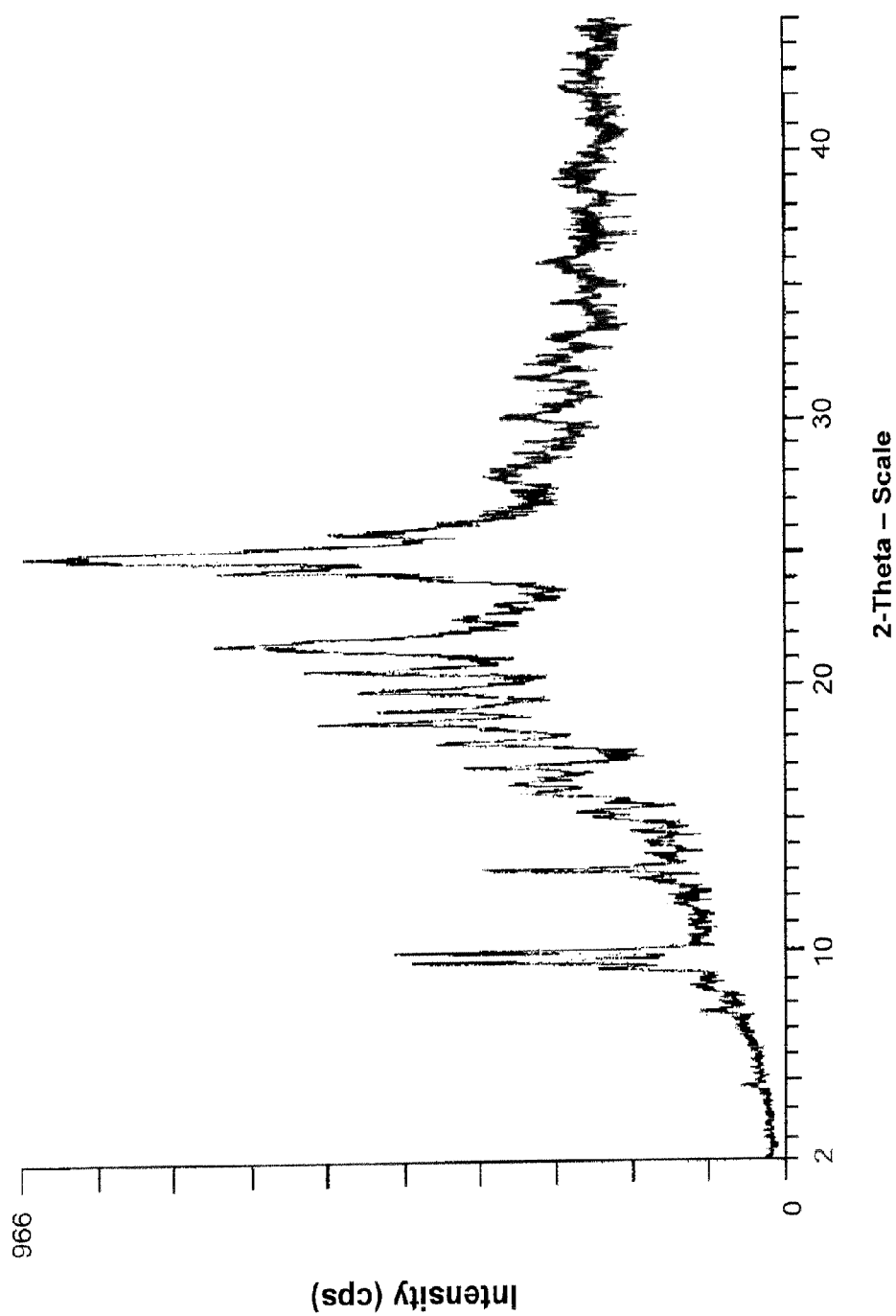
FIG. 20 shows the XRPD patterns of form XVII of compound 1 as obtained by the method disclosed in Examples 21 and 22.

Solid form XVII was characterized by X-ray powder diffraction analysis obtained with Cu Kα radiation. The X-ray powder diffraction pattern consists of a broad halo peak with minor sharp peaks expressed in degrees 2Theta. The locations of the minor sharp peaks are shown in the table below. FIG. 20 shows a XRPD pattern of a typical lot of a substantially amorphous solid state form XVII.

| Angle 2-Theta° | d value Angstrom | Intensity Count | Intensity % % |
|---|---|---|---|
| 3.276 | 26.94524 | 8.42 | 1.2 |
| 4.747 | 18.59877 | 32.6 | 4.8 |
| 5.683 | 15.53955 | 5.75 | 0.8 |
| 7.591 | 11.6373 | 57.9 | 8.5 |
| 8.44 | 10.46849 | 48.7 | 7.2 |
| 9.224 | 9.57963 | 169 | 24.9 |
| 9.505 | 9.29756 | 403 | 59.3 |
| 9.882 | 8.9438 | 421 | 62 |
| 11.651 | 7.58897 | 72.9 | 10.7 |
| 11.93 | 7.41246 | 21.5 | 3.2 |
| 12.645 | 6.99485 | 89.4 | 13.1 |

-continued

| Angle 2-Theta° | d value Angstrom | Intensity Count | Intensity % |
|---|---|---|---|
| 13.015 | 6.79687 | 277 | 40.8 |
| 13.528 | 6.54031 | 47.5 | 7 |
| 14.037 | 6.30422 | 53.9 | 7.9 |
| 14.451 | 6.12451 | 57.5 | 8.5 |
| 14.986 | 5.90686 | 88.8 | 13.1 |
| 15.226 | 5.81445 | 105 | 15.5 |
| 15.6 | 5.67585 | 59.8 | 8.8 |
| 15.929 | 5.55933 | 159 | 23.3 |
| 16.281 | 5.43993 | 167 | 24.6 |
| 16.922 | 5.23544 | 205 | 30.1 |
| 17.36 | 5.10417 | 13.9 | 2 |
| 17.842 | 4.9673 | 204 | 29.9 |
| 18.377 | 4.8238 | 108 | 15.8 |
| 18.635 | 4.75784 | 307 | 45.2 |
| 19.074 | 4.64921 | 216 | 31.8 |
| 19.83 | 4.47353 | 211 | 31.1 |
| 20.596 | 4.30896 | 269 | 39.6 |
| 21.4 | 4.14883 | 272 | 40 |
| 21.627 | 4.10574 | 379 | 55.7 |
| 22.521 | 3.94481 | 93.2 | 13.7 |
| 23.038 | 3.85742 | 56.8 | 8.4 |
| 23.44 | 3.79217 | 35.1 | 5.2 |
| 24.06 | 3.69583 | 200 | 29.4 |
| 24.347 | 3.65298 | 417 | 61.3 |
| 24.959 | 3.56467 | 680 | 100 |
| 25.713 | 3.46183 | 277 | 40.7 |
| 26.099 | 3.4115 | 162 | 23.8 |
| 26.515 | 3.35901 | 90.4 | 13.3 |
| 27.052 | 3.29348 | 55.7 | 8.2 |
| 27.753 | 3.21192 | 111 | 16.3 |
| 28.041 | 3.17956 | 110 | 16.1 |
| 28.742 | 3.10358 | 88.4 | 13 |
| 29.18 | 3.05796 | 74.8 | 11 |
| 30.077 | 2.96872 | 113 | 16.6 |
| 30.5 | 2.92855 | 61 | 9 |
| 31.089 | 2.87436 | 48.2 | 7.1 |
| 31.572 | 2.8315 | 106 | 15.6 |
| 32.076 | 2.78817 | 97.1 | 14.3 |
| 32.387 | 2.76212 | 85 | 12.5 |
| 32.84 | 2.72502 | 44.8 | 6.6 |
| 32.963 | 2.71514 | 65.4 | 9.6 |
| 33.065 | 2.70701 | 61 | 9 |
| 33.201 | 2.69622 | 63.5 | 9.3 |
| 33.64 | 2.66201 | 17.7 | 2.6 |
| 33.924 | 2.6404 | 28 | 4.1 |
| 34.462 | 2.6004 | 64.3 | 9.5 |
| 35.359 | 2.53645 | 44 | 6.5 |
| 35.378 | 2.53515 | 44 | 6.5 |
| 35.712 | 2.51218 | 72.6 | 10.7 |
| 35.952 | 2.49597 | 83.8 | 12.3 |
| 36.736 | 2.44447 | 42.5 | 6.3 |
| 37.149 | 2.41824 | 63 | 9.3 |
| 37.764 | 2.38023 | 55.7 | 8.2 |
| 37.873 | 2.37368 | 50.7 | 7.5 |
| 38.322 | 2.3469 | 17.3 | 2.5 |
| 38.6 | 2.33061 | 32.6 | 4.8 |
| 38.79 | 2.31961 | 70.8 | 10.4 |
| 39.147 | 2.29927 | 45.2 | 6.6 |
| 39.397 | 2.2853 | 70.5 | 10.4 |
| 40.035 | 2.25029 | 47.3 | 7 |
| 40.277 | 2.23737 | 36.6 | 5.4 |
| 41.1 | 2.19443 | 42.6 | 6.3 |
| 41.218 | 2.18844 | 37.8 | 5.6 |
| 41.62 | 2.16821 | 40.3 | 5.9 |
| 42.496 | 2.12551 | 77.5 | 11.4 |
| 42.972 | 2.10308 | 52.1 | 7.7 |
| 43.1 | 2.09714 | 72.3 | 10.6 |
| 43.72 | 2.06881 | 65.1 | 9.6 |
| 44.24 | 2.04569 | 32.9 | 4.8 |
| 44.535 | 2.03284 | 36.3 | 5.3 | b) Characterization of Solid Form XVIII

Figure 21:
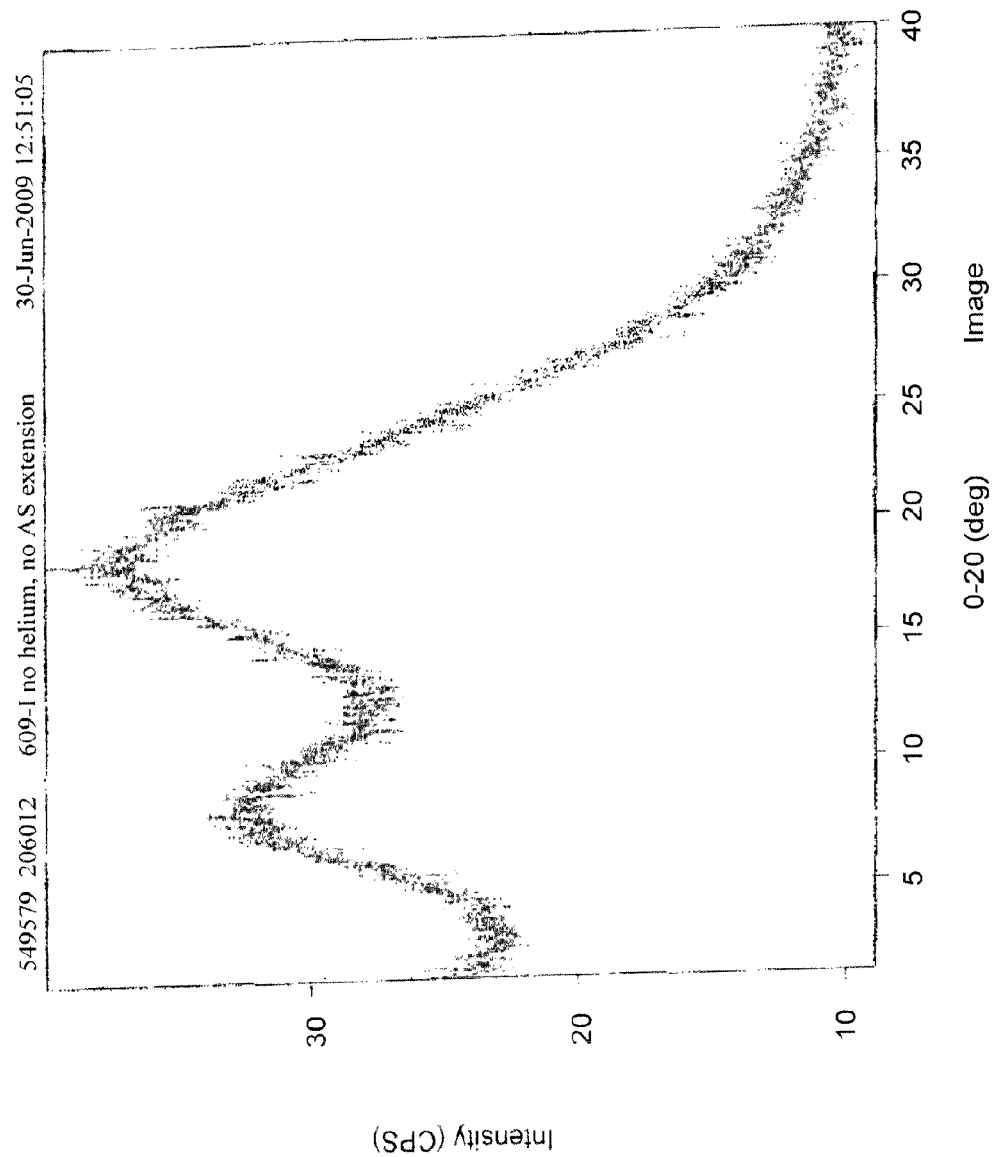
FIG. 21 shows the XRPD patterns of form XVIII of compound 1 as obtained by the method disclosed in Examples 21 and 22.

Solid form XVIII was characterized by X-ray powder diffraction analysis obtained with Cu Kα radiation. The X-ray powder diffraction pattern exhibits two broad halo peaks expressed in degrees 2Theta as shown in FIG. 21.

c) Characterization of Solid Form XIX

Figure 22:
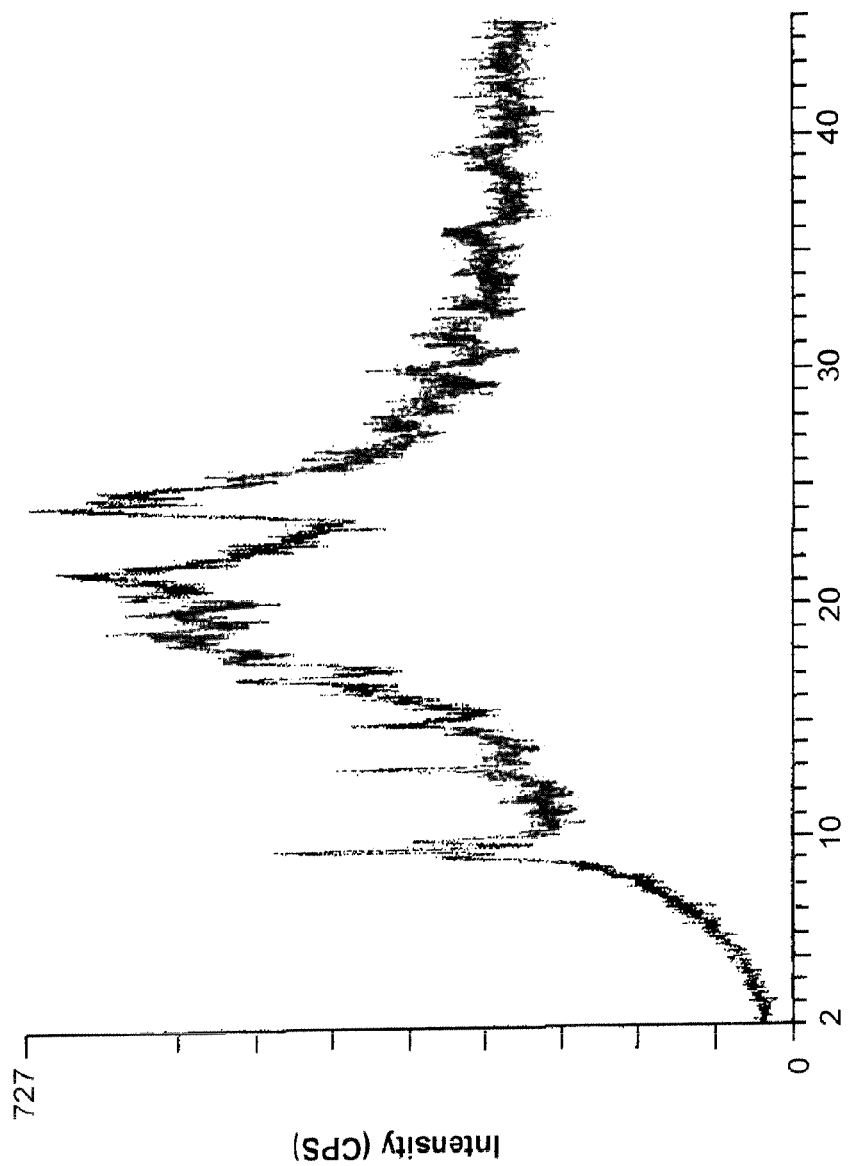
FIG. 22 shows the XRPD patterns of form XIX of compound 1 as obtained by the method disclosed in Examples 21 and 22.

Solid form XIX was characterized by X-ray powder diffraction analysis obtained with Cu Kα radiation. The X-ray powder diffraction pattern consists of a broad halo peak with minor sharp peaks expressed in degrees 2Theta. FIG. 22 shows a XRPD pattern of a typical lot of a substantially amorphous solid state form XIX.

d) Characterization of Solid Form XX

Figure 23:
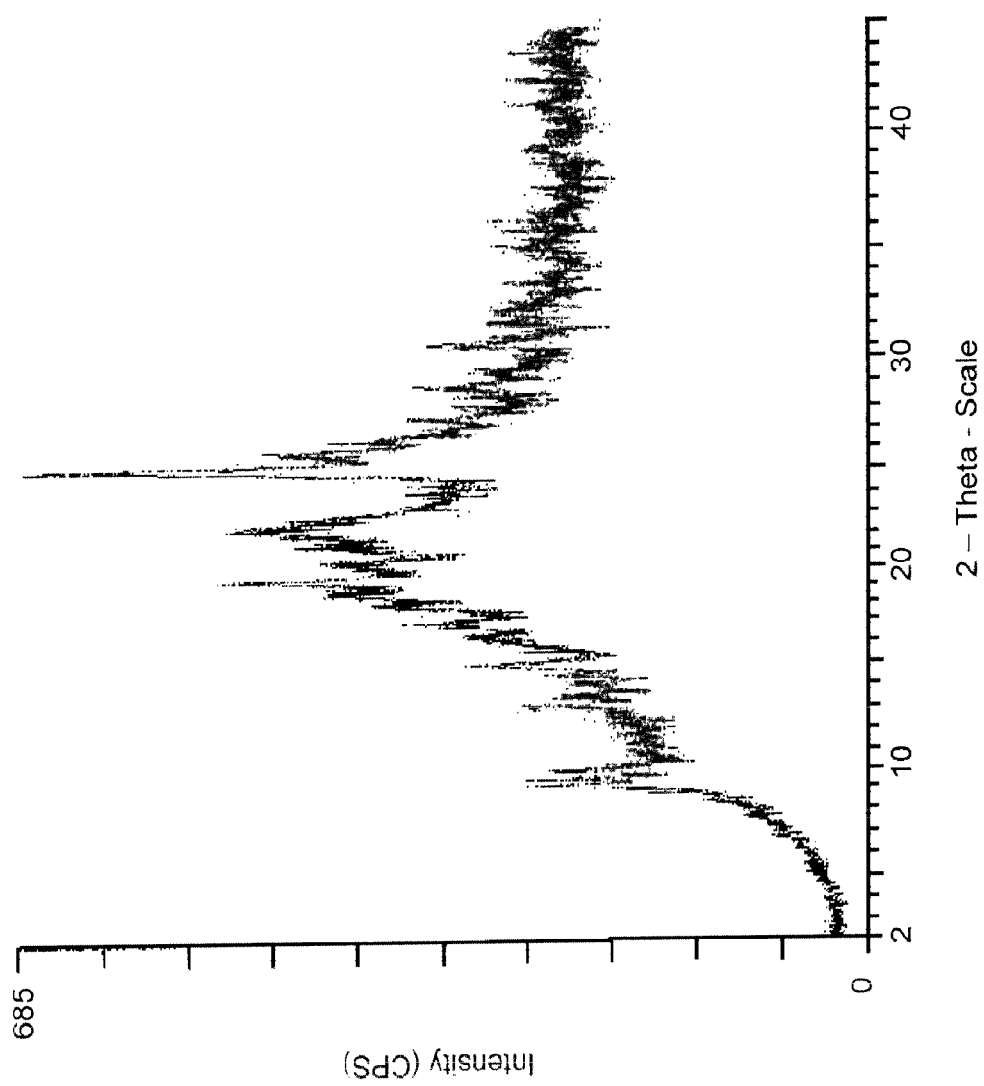
FIG. 23 shows the XRPD patterns of form XX of compound 1 as obtained by the method disclosed in Examples 21 and 22.

Solid form XX was characterized by X-ray powder diffraction analysis obtained with Cu Kα radiation. The X-ray powder diffraction pattern consists of a broad halo peak with minor sharp peaks expressed in degrees 2Theta. FIG. 23 shows a XRPD pattern of a typical lot of a substantially amorphous solid state form XX.

e) Characterization of Solid Form XXI

Figure 24:
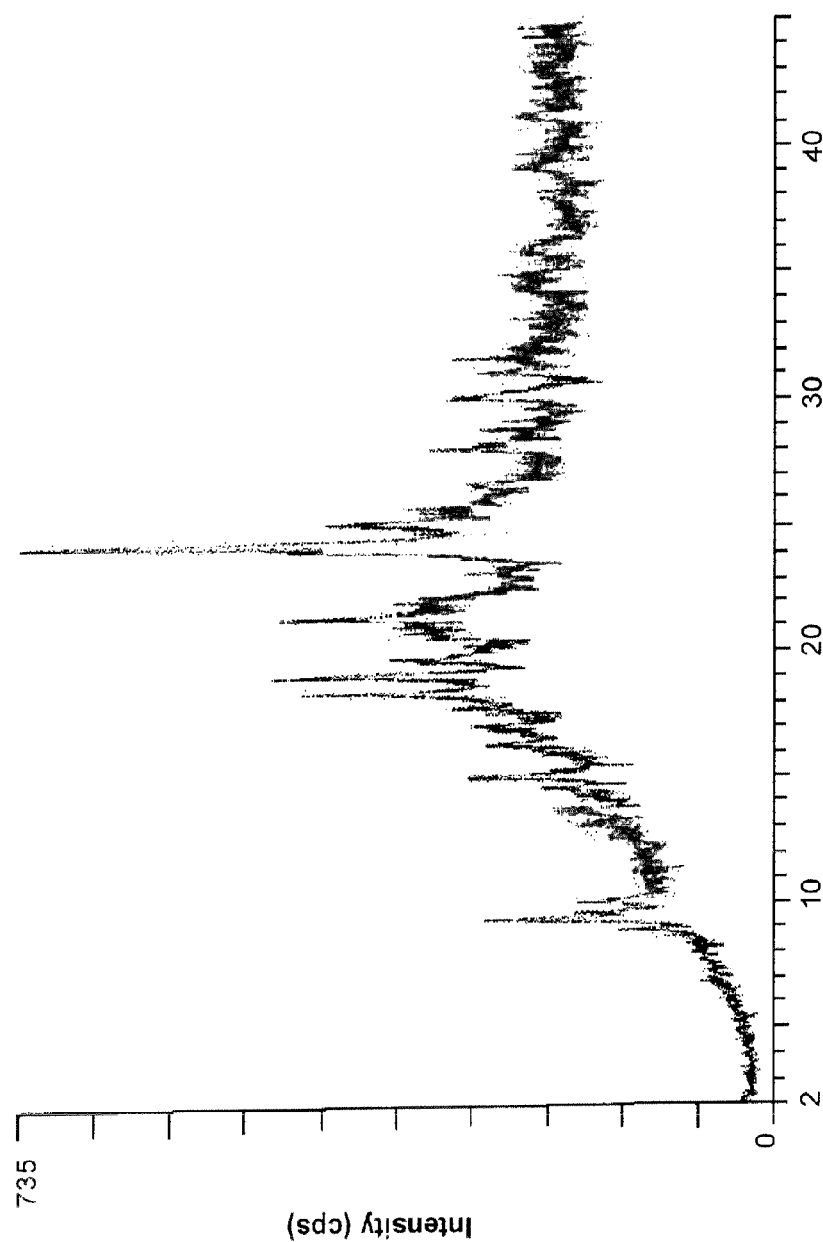
FIG. 24 shows the XRPD patterns of form XXI of compound 1 as obtained by the method disclosed in Examples 21 and 22.

Solid form XXI was characterized by X-ray powder diffraction analysis obtained with Cu Kα radiation. The X-ray powder diffraction pattern consists of a broad halo peak with minor sharp peaks expressed in degrees 2Theta. FIG. 24 shows a XRPD pattern of a typical lot of a substantially amorphous solid state form XXI.

J) Characterization of Solid Form XXII

Figure 25:
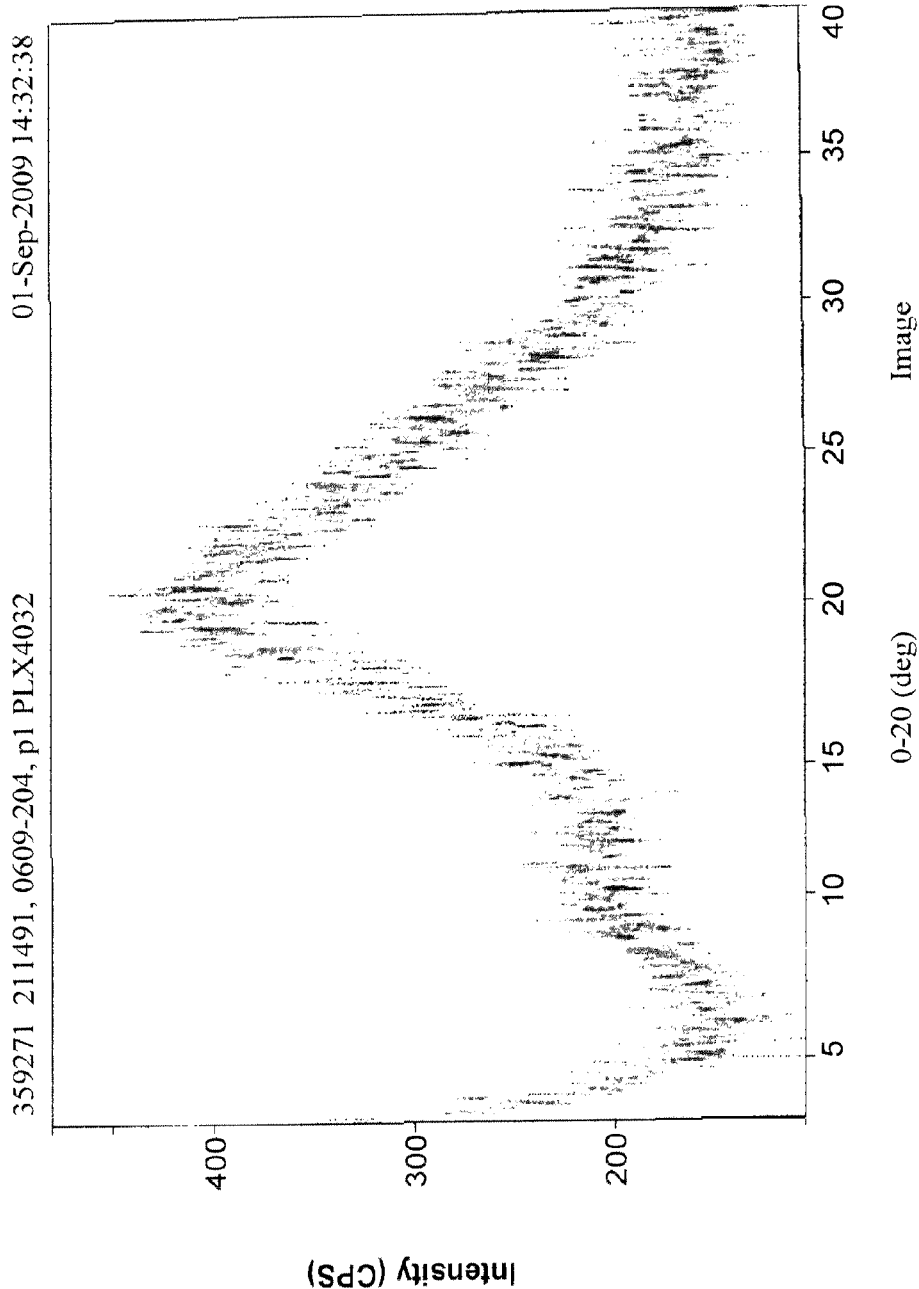
FIG. 25 shows the XRPD patterns of form XXII of compound 1 as obtained by the method disclosed in Examples 21 and 22.

Solid form XXII was characterized by X-ray powder diffraction analysis obtained with Cu Kα radiation. The X-ray powder diffraction pattern consists of a broad halo peak expressed in degrees 2Theta. FIG. 25 shows a XRPD pattern of a typical lot of a substantially amorphous solid state form XXII.

g) Characterization of Solid Form XXIII

Figure 26:
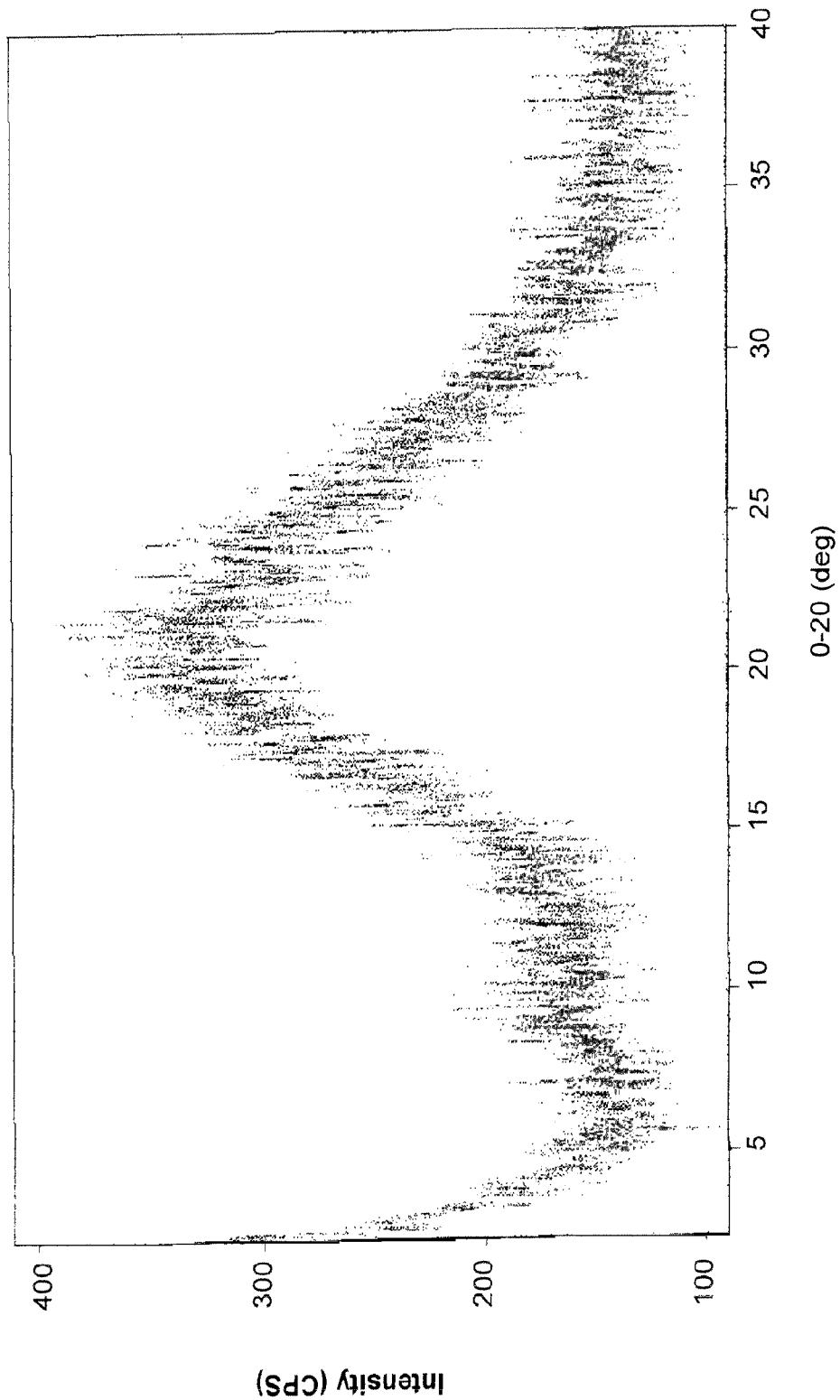
FIG. 26 shows the XRPD patterns of form XXIII of compound 1 as obtained by the method disclosed in Examples 21 and 22.

Solid form XXIII was characterized by X-ray powder diffraction analysis obtained with Cu Kα radiation. The X-ray powder diffraction pattern consists of a broad halo peak expressed in degrees 2Theta. FIG. 26 shows a XRPD pattern of a typical lot of a substantially amorphous solid state form XXIII.

h) Characterization of Solid Form XXIV

Figure 27:
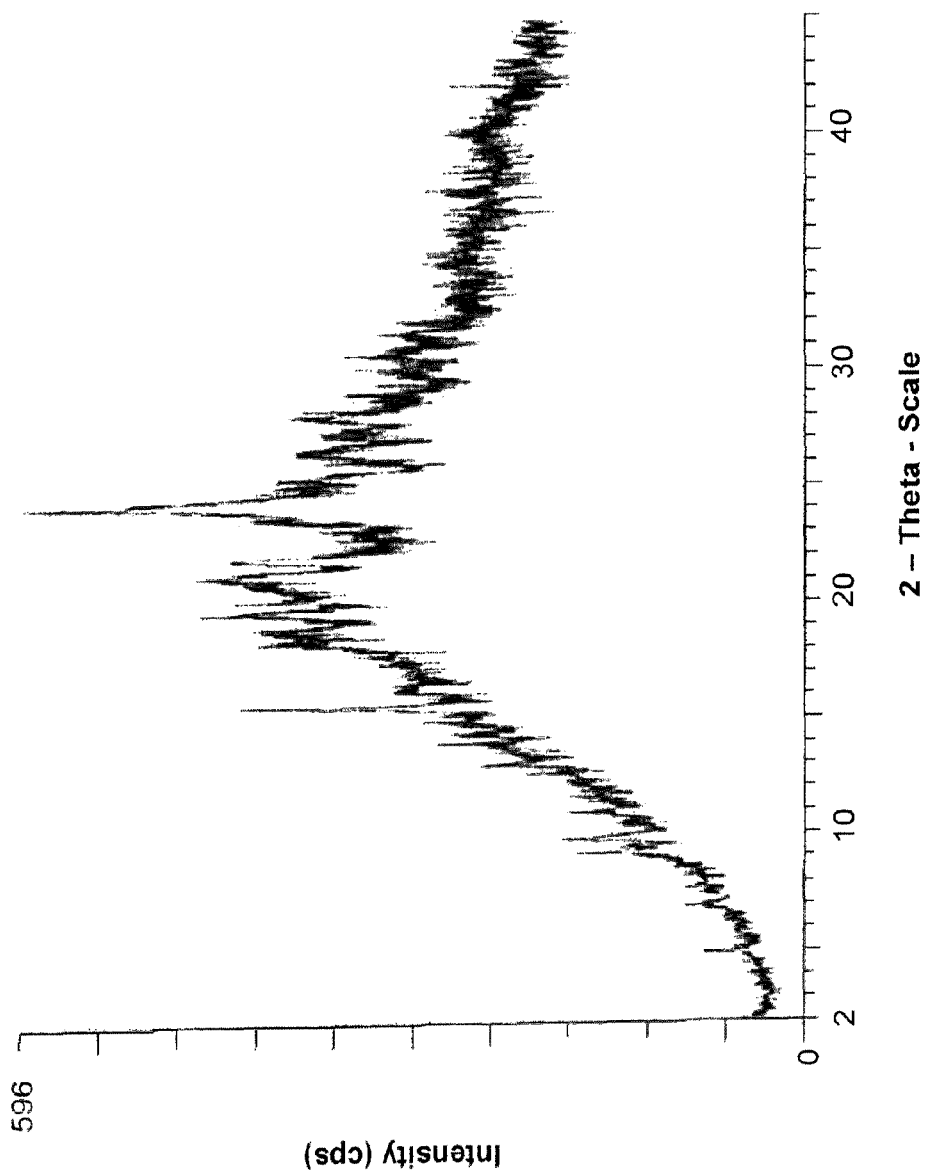
FIG. 27 shows the XRPD patterns of form XXIV of compound 1 as obtained by the method disclosed in Examples 21 and 22.

Solid form XXIV was characterized by X-ray powder diffraction analysis obtained with Cu Kα radiation. The X-ray powder diffraction pattern consists of a broad halo peak with minor sharp peaks expressed in degrees 2Theta. FIG. 27 shows a XRPD pattern of a typical lot of a substantially amorphous solid state form XXIV.

i) Characterization of Solid Form XXV

Figure 28:
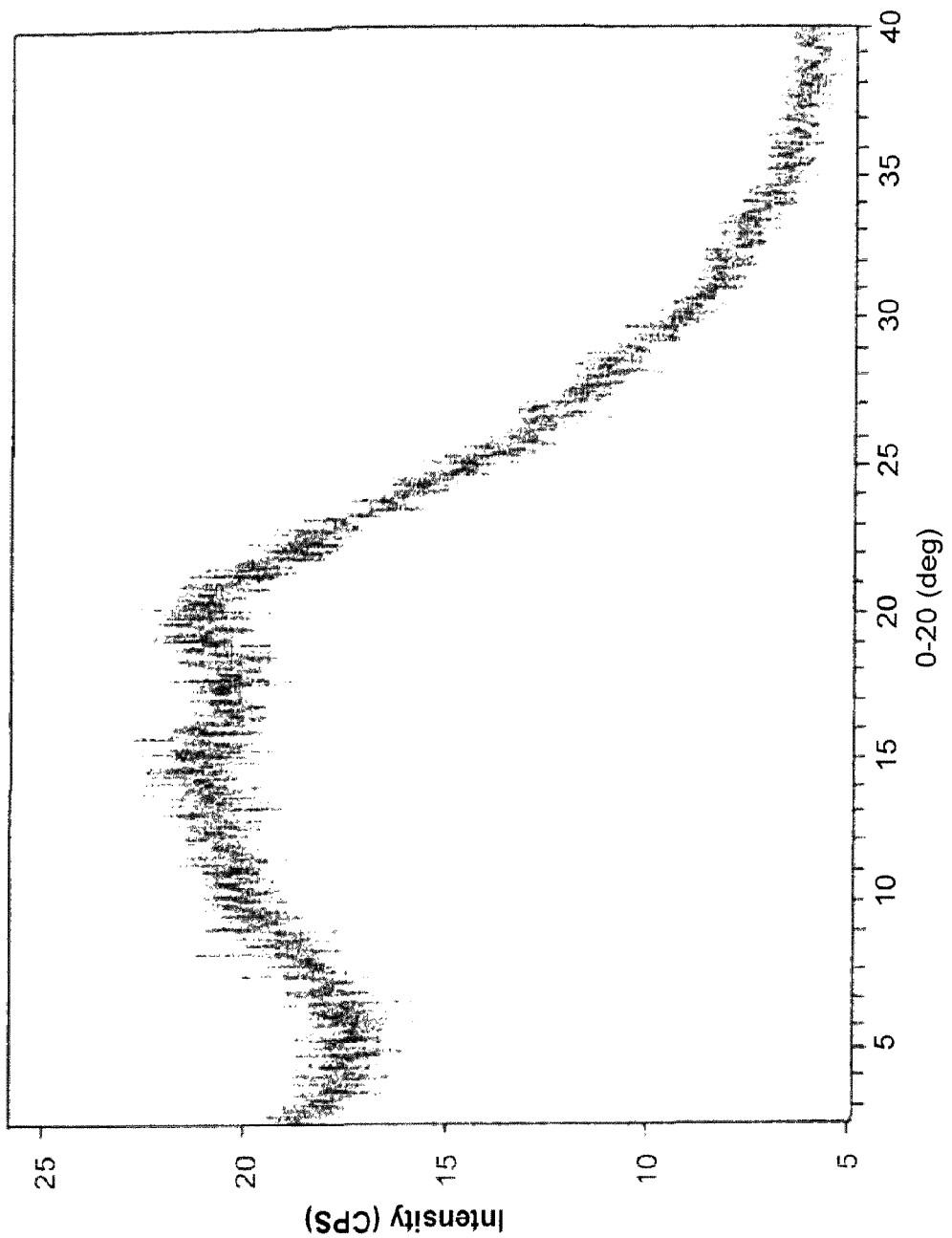
FIG. 28 shows the XRPD patterns of form XXV of compound 1 as obtained by the method disclosed in Examples 21 and 22.

Solid form XXV was characterized by X-ray powder diffraction analysis obtained with Cu Kα radiation. The X-ray powder diffraction pattern consists of a broad halo peak expressed in degrees 2Theta. FIG. 28 shows a XRPD pattern of a typical lot of a substantially amorphous solid state form XXV.

j) Characterization of Solid Form XXVI

Figure 29:
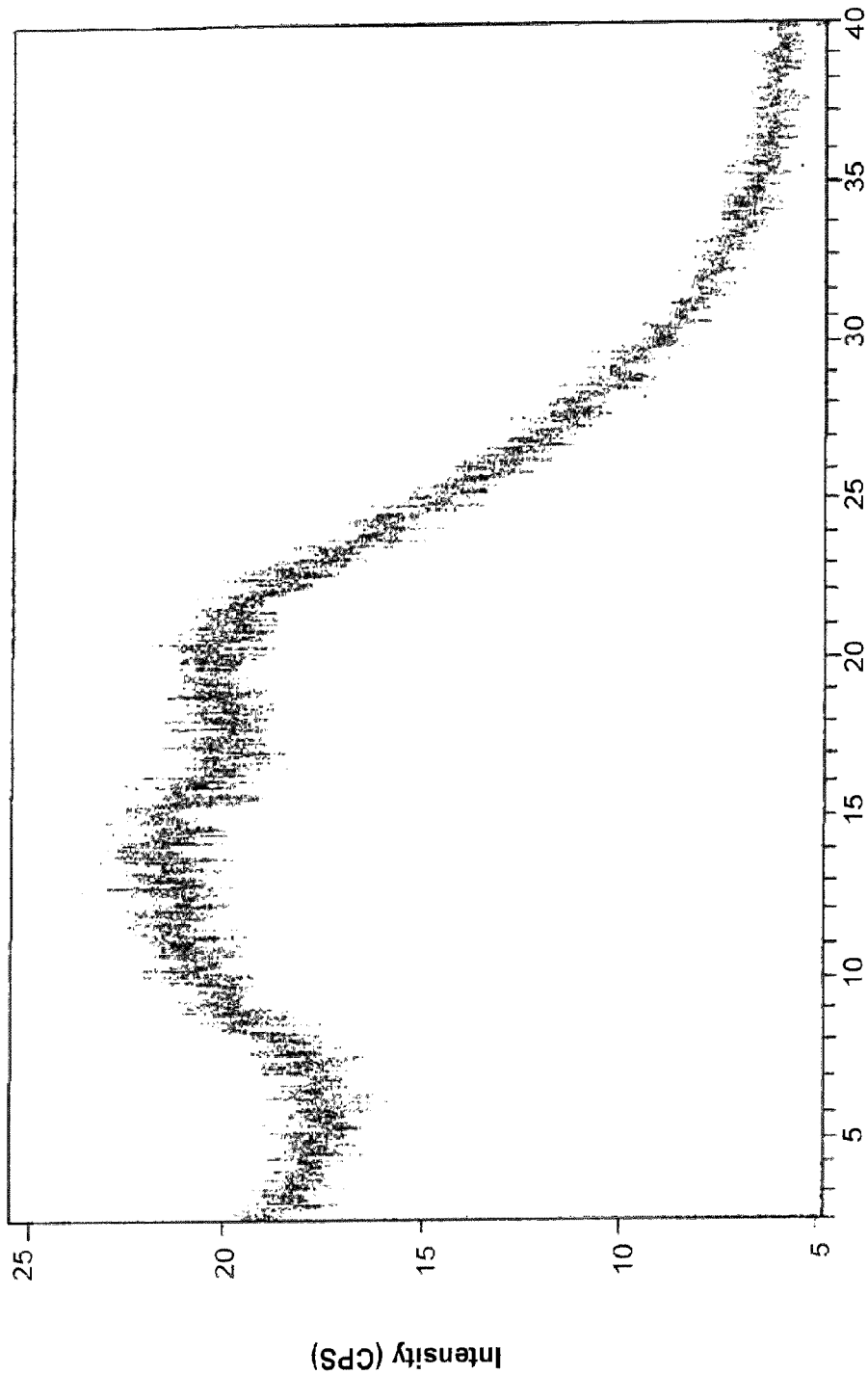
FIG. 29 shows the XRPD patterns of form XXVI of compound 1 as obtained by the method disclosed in Examples 21 and 22.

Solid form XXVI was characterized by X-ray powder diffraction analysis obtained with Cu Kα radiation. The X-ray powder diffraction pattern consists of a broad halo peak expressed in degrees 2Theta. FIG. 29 shows a XRPD pattern of a typical lot of a substantially amorphous solid state form XXVI.

The invention claimed is:

1. A solid form of the compound of formula 1,

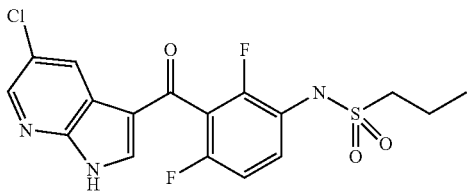

wherein said solid form is selected from the group consisting of
   a) a substantially amorphous form of compound 1 selected from form XXIV, XXV, XXVI or combinations thereof, wherein the compound 1 is molecularly dispersed;
   b) a solvate selected from form III, IV, V, VI, VII, IX, X, XI, XII, XIII, XIV or XV;
   c) a polymorph selected from form VIII or XVI; and
   d) the sulfuric acid-, hydrobromic acid- or hydrochloric acid salt of compound 1.

2. The solid form of claim 1, selected from a substantially amorphous form of compound 1 selected from form XXIV, XXV, XXVI or combinations thereof, wherein compound 1 is molecularly dispersed within a polymer matrix.

3. The solid form (XXIV) of claim 2, characterized by an X-ray powder diffraction pattern substantially as shown in FIG. 27.

4. The solid form (XXV) of claim 2, characterized by an X-ray powder diffraction pattern substantially as shown in FIG. 28.

5. The solid form (XXVI) of claim 2, characterized by an X-ray powder diffraction pattern substantially as shown in FIG. 29.

6. The solid form of claim 2, wherein the solid form is prepared by a spray dispersion process.

7. The solid form of claim 2, wherein the polymer is selected from methacrylic acid copolymers, polyvinylpyrrolidone (povidone), 4-vinylpyrrolidone-vinyl acetate copolymer (copovidone) or copolymers of methacrylic acid and ethylacrylate (EUDRAGIT® L100-55).

8. A pharmaceutical composition comprising at least one solid form according to claim 2, or a pharmaceutically acceptable salt thereof, and a pharmaceutically acceptable carrier, additives or excipients.

9. The solid form of claim 1, selected from a solvate of form III, IV, V, VI, VII, IX, X, XI, XII, XIII, XIV or XV.

10. The solid form of claim 1, selected from a polymorph of form VIII or XVI.

11. The solid form of claim 1, selected from the sulfuric acid-, hydrobromic acid- or hydrochloric acid salt of compound 1.

12. A solid form (form III) according to claim 9, characterized by an X-ray powder diffraction pattern comprising characteristic peaks at approximately 9.5, 10.0, 13.0, 16.7, 18.7, 20.1, 21.0 and 25.6 degrees 2Theta (±0.2 degrees 2Theta).

13. A solid form (form IV) according to claim 9, characterized by an X-ray powder diffraction pattern comprising characteristic peaks at approximately 5.5, 7.4, 11.0, 13.4, 14.8, 16.0, 16.7, 17.1, 17.9, 19.1, 19.5, 20.1, 20.5, 20.9, 21.2, 22.2, 23.0, 23.6, 24.2, 24.5 and 25.1 degrees 2Theta (±0.2 degrees 2Theta).

14. A solid form (form V) according to claim 9, characterized by an X-ray powder diffraction pattern comprising characteristic peaks at approximately 12.7, 13.1, 14.3, 16.3, 19.0, 20.1, 22.4, 25.1, 27.1 and 28.9 degrees 2Theta (±0.2 degrees 2Theta).

15. A solid form (form VI) according to claim 1, characterized by an X-ray powder diffraction pattern comprising characteristic peaks at approximately 7.8, 10.3, 11.4, 11.8, 15.1, 15.6, 16.1, 16.6, 18.6, 18.9, 19.2, 20.4, 21.0, 21.6, 22.8, 24.6, 25.1, 25.8, 26.1, 27.4 and 28.8 degrees 2Theta (±0.2 degrees 2Theta).

16. A solid form (form VII) according to claim 9, characterized by an X-ray powder diffraction pattern comprising characteristic peaks at approximately 7.6, 9.4, 9.9, 13.1, 15.9, 16.2, 17.0, 18.1, 18.8, 19.9, 20.5, 20.7, 21.4, 21.8, 24.3, 24.9 and 25.3 degrees 2Theta (±0.2 degrees 2Theta).

17. A solid form (form IX) according to claim 9, characterized by an X-ray powder diffraction pattern comprising characteristic peaks at approximately 9.5, 9.9, 13.0, 15.9, 16.4, 17.0, 17.9, 18.7, 19.9, 20.7, 21.7, 24.8 and 25.1 degrees 2Theta (±0.2 degrees 2Theta).

18. A solid form (form X) according to claim 9, characterized by an X-ray powder diffraction pattern comprising characteristic peaks at approximately 7.4, 9.2, 10.8, 13.6, 14.9, 19.0, 20.2, 21.4, 22.4, 23.7, 25.5, 27.0 and 29.8 degrees 2Theta (±0.2 degrees 2Theta).

19. A solid form (form XI) according to claim 9, characterized by an X-ray powder diffraction pattern comprising characteristic peaks at approximately 8.0, 12.1, 12.6, 13.4, 13.9, 14.8, 16.2, 17.6, 18.5, 19.2, 20.1, 21.0, 21.4, 21.7, 23.5, 25.3, 25.5, 26.6, 27.0 and 30.8 degrees 2Theta (±0.2 degrees 2Theta).

20. A solid form (form XII) according to claim 9, characterized by an X-ray powder diffraction pattern comprising characteristic peaks at approximately 7.5, 9.9, 12.1, 13.6, 16.2, 16.7, 17.1, 17.5, 18.3, 18.5, 20.1, 21.7, 22.4, 23.4, 24.3, 25.6, 26.9 and 31.6 degrees 2Theta (±0.2 degrees 2Theta).

21. A solid form (form XIII) according to claim 9, characterized by an X-ray powder diffraction pattern comprising characteristic peaks at approximately 5.1, 5.8, 6.9, 15.3, 16.2, 17.4, 18.4, 18.9, 19.5, 20.4, 21.1, 21.5, 22.2, 22.6, 25.2 and 25.7 degrees 2Theta (±0.2 degrees 2Theta).

22. A solid form (form XIV) according to claim 9, characterized by an X-ray powder diffraction pattern comprising characteristic peaks at approximately 5.2, 10.2, 12.9, 13.9, 17.1, 17.6, 18.7, 19.8, 20.1, 20.5, 21.0, 21.7, 22.8, 24.1, 25.1, 25.5, 27.1 and 27.4 degrees 2Theta (±0.2 degrees 2Theta).

23. A solid form (form XV) according to claim 9, characterized by an X-ray powder diffraction pattern comprising characteristic peaks at approximately 12.6, 13.8, 14.6, 16.2, 16.6, 17.8, 18.3, 20.4, 20.7, 21.4, 22.4, 23.2, 24.2, 24.5, 25.5, 26.9, 27.8 and 28.7 degrees 2Theta (±0.2 degrees 2Theta).

24. A solid form designated "pattern 6" according to claim 9, characterized in that it comprises signals in its X-ray powder diffraction curve at positions 7.0, 8.4, 8.9, 13.0, 13.8, 17.7, 18.8, 20.7, 25.8 and 29.7 degrees 2Theta (±0.2 degrees 2Theta).

25. A solid form (form VIII) according to claim 10, characterized in that it comprises signals in its X-ray powder diffraction curve at positions 5.0, 11.3, 11.6, 12.0, 13.8, 16.2, 16.7, 19.0, 20.1, 20.8, 22.5 and 27.1 degrees 2Theta (±0.2 degrees 2Theta).

26. A solid form (form XVI) according to claim 10, characterized by its Raman spectrum as presented in FIG. 15.

27. The sulfuric acid salt according to claim 11, characterized by an X-ray powder diffraction pattern comprising characteristic peaks at approximately 4.7, 6.7, 10.6, 13.3, 14.5, 15.7, 16.4, 18.3, 18.6, 18.9, 19.5, 20.1, 20.9, 21.2, 23.2, 23.7, 24.0, 26.9 and 30.0 degrees 2Theta (±0.2 degrees 2Theta).

28. The hydrobromic acid salt according to claim 11, characterized by an X-ray powder diffraction pattern comprising characteristic peas at approximately 5.7, 6.8, 11.4, 13.6, 18.1, 19.8, 20.2, 21.4, 21.8, 24.6, 26.1, 27.3 and 29.2 degrees 2Theta (±0.2 degrees 2Theta).

29. The hydrochloric acid salt according to claim 11, characterized by an X-ray powder diffraction pattern comprising characteristic peaks at approximately 6.6, 7.8, 11.2, 12.6, 14.1, 14.7, 16.3, 17.8, 19.3, 19.6, 20.7, 21.5, 22.7, 24.1, 25.4 and 25.8 degrees 2Theta (±0.2 degrees 2Theta).

30. A pharmaceutical composition comprising at least one of the solid forms according to claim 9, together with pharmaceutically acceptable additives, carriers or excipients.

* * * * *

UNITED STATES PATENT AND TRADEMARK OFFICE
CERTIFICATE OF CORRECTION

PATENT NO. : 8,865,735 B2
APPLICATION NO. : 13/817124
DATED : October 21, 2014
INVENTOR(S) : Prabha N. Ibrahim et al.

It is certified that error appears in the above-identified patent and that said Letters Patent is hereby corrected as shown below:

ON THE TITLE PAGE

In Item (57), Abstract, 1, please replace:

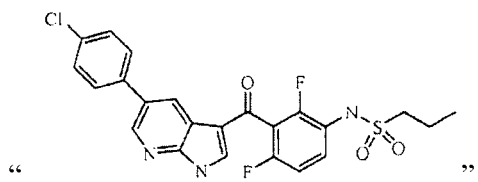

with the following:

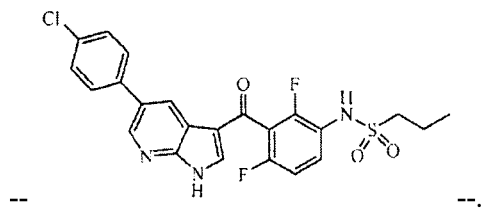

IN THE SPECIFICATION

In Column 1, Lines 20-29, please replace:

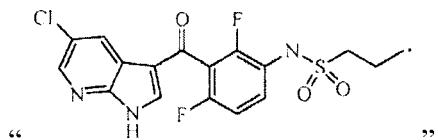

with the following:

Signed and Sealed this
Sixth Day of October, 2015

Michelle K. Lee
*Director of the United States Patent and Trademark Office*

CERTIFICATE OF CORRECTION (continued)
U.S. Pat. No. 8,865,735 B2

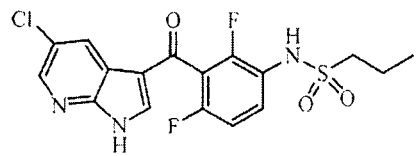

-- --.

IN THE CLAIMS

In Claim 1, Column 21, Lines 5-12, please replace:

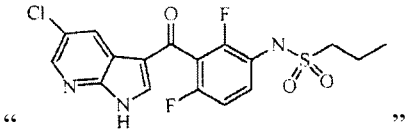

" "

with the following:

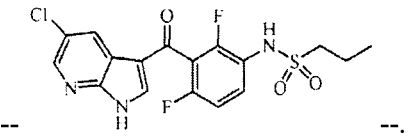

-- --.

In Claim 15, Column 22, Line 6, please replace "claim 1" with --claim 9--.

In Claim 28, Column 23, Line 5, please replace "characteristic peas" with --characteristic peaks--.